US012747443B2

(12) United States Patent
Walton et al.

(10) Patent No.: US 12,747,443 B2
(45) Date of Patent: Sep. 29, 2026

(54) IMMUNE CELLS WITH ENHANCED CYTOTOXICITY AND METHODS OF USE THEREOF

(71) Applicants: Ludwig Institute for Cancer Research Ltd, Zurich (CH); The Wistar Institute, Philadelphia, PA (US)

(72) Inventors: Zandra Walton, Philadelphia, PA (US); Zachary Stine, Philadelphia, PA (US); Yaoyu Gong, Philadelphia, PA (US); Chi V. Dang, Philadelphia, PA (US)

(73) Assignees: Ludwig Institute for Cancer Research Ltd, New York, NY (US); The Wistar Institute, Philadelphia, PA (US)

( * ) Notice: Subject to any disclaimer, the term of this patent is extended or adjusted under 35 U.S.C. 154(b) by 1175 days.

(21) Appl. No.: 17/630,068

(22) PCT Filed: Jul. 24, 2020

(86) PCT No.: PCT/US2020/043505
§ 371 (c)(1),
(2) Date: Jan. 25, 2022

(87) PCT Pub. No.: WO2021/021631
PCT Pub. Date: Feb. 4, 2021

(65) Prior Publication Data

US 2022/0267781 A1 Aug. 25, 2022

Related U.S. Application Data

(60) Provisional application No. 62/879,220, filed on Jul. 26, 2019.

(51) Int. Cl.
*C12N 15/62* (2006.01)
*A61K 40/15* (2025.01)
(Continued)

(52) U.S. Cl.
CPC .............. *C12N 15/62* (2013.01); *A61K 40/15* (2025.01); *A61K 40/30* (2025.01);
(Continued)

(58) Field of Classification Search
CPC .... C12N 15/62; C12N 5/0646; C12N 9/1205; C12N 9/88; C12N 2510/00;
(Continued)

(56) References Cited

U.S. PATENT DOCUMENTS 7,638,288 B2 * 12/2009 Van Rompaey ........ A61P 19/10 435/7.1
8,236,320 B2 * 8/2012 Kim ........................ A61P 37/00 424/193.1
2003/0059771 A1 3/2003 Clark et al.

FOREIGN PATENT DOCUMENTS

WO WO-2005103716 A2 * 11/2005 ................ A61P 5/14

OTHER PUBLICATIONS

Addgene (Plasmid #34611, LAMP1-mRFP-FLAG)/Zoncu et al. mTORC1 senses lysosomal amino acids through an inside-out mechanism that requires the vacuolar H-ATPase. Science (2011) 334: 6056, p. 678-683.*

(Continued)

*Primary Examiner* — Joanne Hama
*Assistant Examiner* — Jami Michelle Gurley
(74) *Attorney, Agent, or Firm* — Fox Rothschild LLP

(57) ABSTRACT

This disclosure provides methods for enhancing antitumor cytotoxicity of immune cells by introducing to the immune cells a genetic modification that comprises overexpression of RHEB or a functional fragment thereof, overexpression of LAMP 1-RHEB or a functional fragment thereof, overexpression of CA9 or a functional fragment thereof, overex-
(Continued)

pression of NHE1 or a functional fragment thereof, or combination thereof.

20 Claims, 13 Drawing Sheets

Specification includes a Sequence Listing.

(51) Int. Cl.
*A61K 40/30* (2025.01)
*A61K 40/42* (2025.01)
*C07K 14/47* (2006.01)
*C07K 14/705* (2006.01)
*C12N 5/0783* (2010.01)
*C12N 9/12* (2006.01)
*C12N 9/88* (2006.01)

(52) U.S. Cl.
CPC .......... *A61K 40/4271* (2025.01); *C07K 14/47* (2013.01); *C07K 14/705* (2013.01); *C12N 5/0646* (2013.01); *C12N 9/1205* (2013.01); *C12N 9/88* (2013.01); *A61K 2239/31* (2023.05); *A61K 2239/38* (2023.05); *A61K 2239/57* (2023.05); *C12N 2510/00* (2013.01); *C12N 2740/16043* (2013.01)

(58) Field of Classification Search
CPC .... C12N 2740/16043; A61K 39/46449; A61K 39/4613; A61K 2239/57; A61K 39/4637; A61K 2239/31; A61K 2239/38; A61K 48/005; C07K 14/47; C07K 14/705
See application file for complete search history.

(56) References Cited

OTHER PUBLICATIONS

McDonald, et al. Overcoming Hypoxia-Mediated Tumor Progression: Combinatorial Approaches Targeting pH Regulation, Angiogenesis and Immune Dysfunction. Front.Cell Dev. Biol. (2016), 4:27, p. 1-16.*

Angarola and Ferguson. Coordination of Rheb lysosomal membrane interactions with mTORC1 activation. F1000Research (2020), 9:450, p. 1-12.*

Fukuda, et al. Cloning of cDNAs Encoding Human Lysosomal Membrane Glycoproteins, h-lamp-1 and h-lamp-2. JBC (1988), 263: 35, p. 18920-18928.*

Zot, et al. Structure of a Gene for a Lysosomal Membrane Glycoprotein (LEPI 00). JBC (1990), 263:34, p. 20988-20995.*

Recombinant Human Serum Albumin/Granulocyte Colony Stimulating Factor Fusion Protein for Breast Cancer Patients. ClinicalTrials.gov Identifier: NCT03251768. Sponsor: Tianjin SinoBiotech Ltd.. Study Completion Date: Apr. 2019.*

Shi, et al. The role of Na+/H+ exchanger isoform 1 in inflammatory responses: Maintaining H+ homeostasis of immune cells. *Annunziato*, L. (eds) Sodium Calcium Exchange: A Growing Spectrum of Pathophysiological Implications. Adv. in Exp. Med. and Biol., vol. 961. Springer, Boston, MA; p. 411-418.*

Milone et al. Clinical use of lentiviral vectors. Leukemia (2018), 32, p. 1529-1541.*

Velica et al. Genetic Regulation of Fate Decisions in Therapeutic T Cells to Enhance Tumor Protection and Memory Formation. Cancer Research (2015), 75:13, p. 2641-2652.*

Singh, et al. Alkaline cytosolic pH and high sodium hydrogen exchanger 1 (NHE1) activity in Th9 cells. JBC (2016), 291:45, p. 23662-23671.*

Li and Eastman. Apoptosis in an interleukin-2-dependent cytotoxic t lymphocyte cell line is associated with intracellular acidification. JBC (1995), 270:7, p. 3203-3211.*

Wilkie, et al. Selective expansion of chimeric antigen receptor-targeted T-cells with potent effector function using interleukin-4. JBC (2010), 285:33, p. 25538-25544.*

CART19 to Treat B-Cell Leukemia or Lymphoma That Are Resistant or Refractory to Chemotherapy. ClinicalTrials.gov Identifier: NCT01029366. Sponsor: University of Pennsylvania. Study Completion Date: May 2016.*

Besser et al. Modifying interleukin-2 concentrations during culture improves function of T cells for adoptive immunotherapy. Cytotherapy (2009), 11:2, p. 206-217.*

Slepkov, et al. Structural and functional analysis of the Na+/H+ exchanger. Biochem. J. 2007, 401, 623-633.*

Zandra E Walton et al: "mTOR Senses Intracellular pH through Lysosome Dispersion from RHEB", Bioessays, John Wiley & Sons Ltd, GB, vol. 41, No. 7, Jun. 3, 2019.

Extended European Search Report for European patent application 20847645.7 dated Oct. 26, 2023, 16 pages.

Singh Yogesh et al: "Alkaline Cytosolic pH and High Sodium Hydrogen Exchanger 1 (NHEI) Activity in Th9 Cells", Journal of Biological Chemistry, vol. 291, No. 45, Sep. 14, 2016 (Sep. 14, 2016), pp. 23662-23671.

Muller B et al: "An acidic microenvirorunent impairs the generation of non-major histocompatibility complex-restricted killer cells", Cancer Research, Wiley-Blackwell Publishing Ltd, GB, vol. 99, No. 3, Dec. 25, 2001 (Dec. 25, 2001), pp. 375-384.

Database Uniprot [Online] Uniprot; Feb. 1, 1991 (Feb. 1, 1991), Sardet C.: "RecName: Full=Sodium/hydrogen exchanger 1;", XP093064818, retrieved from EBI accession No. P19634 Database accession No. P19634.

Gong Yao-Yu et al: "Na+/H+-exchanger 1 Enhances Antitumor Activity of Engineered NK-92 Natural Killer Cells", 6Ludwig Institute for Cancer Research, New York, New York., vol. 2, No. 8, Aug. 22, 2022 (Aug. 22, 2022) , pp. 842-856.

Partial Supplemental European Search Report for European Patent Application No. 20847645.7, dated Jul. 26, 2023, 18 pages.

Velica et al., Genetic Regulation of Fate Decisions in Therapeutic T Cells to Enhance Tumor Protection and Memory Formation. Cancer Research. Jul. 1, 2015, vol. 75, No. 13, pp. 3641-2652.

Wal Ton et al., Acid Suspends the Circadian Clock in Hypoxia through Inhibition of mTOR. Cell. Jun. 28, 2018, vol. 174, pp. 72-87.

International Search Report and Written Opinion mailed Jan. 7, 2021, for International Application No. PCT/US20/43505, 12 pages.

* cited by examiner

C

A

C

D

B

C

IMMUNE CELLS WITH ENHANCED CYTOTOXICITY AND METHODS OF USE THEREOF

CROSS-REFERENCE TO RELATED APPLICATIONS

The present application is a National Stage Application under 35 U.S.C. § 371 of International Application No. PCT/US2020/043505 filed Jul. 24, 2020, which claims priority under 35 U.S.C. § 119(e) to U.S. Provisional Patent Application No. 62/879,220, filed Jul. 26, 2019, the disclosures of all of which are hereby incorporated by reference in their entireties.

FIELD OF THE INVENTION

This invention relates generally to methods for enhancing antitumor cytotoxicity of immune cells, such as natural killer cells or T-cells.

BACKGROUND OF THE INVENTION

Melanoma is an aggressive form of skin cancer with increasing incidence and nearly 100,000 new cases per year in the United States. While early-stage melanoma can be managed by surgical resection, unresectable or metastatic melanoma is challenging to treat. Although about 50% of the melanoma patients with BRAF V600 mutations can be treated with inhibitors against BRAF and/or MEK, the majority of them rapidly develop resistance, leading to a median progression-free survival of less than 12 months in these patients. In parallel, immunotherapeutic approaches have been developed for advanced melanoma in the past decade. These include checkpoint blockade immunotherapy, which targets inhibitory immune signals such as CTLA-4 and PD-1 to activate the patients' own antitumor immunity. Although checkpoint blockade has achieved long-lasting effects in a subset of patients, more than 60% of patients fail to respond. Another example of melanoma immunotherapy is adoptive cell transfer (ACT), which utilizes ex vivo expanded cytotoxic T cells to kill tumor cells. Despite improvements made by engineering the T cells to express tumor antigen-specific T cell receptors, clinical trials of ACT reported less than 50% response rates. Resistance to both checkpoint blockade and ACT is thought to be in part mediated by suppressed effector immune cell function in the tumor microenvironment (TME) and/or immune evasion by tumor cells. Melanoma cells frequently downregulate major histocompatibility complex (MHC) class I molecules involved in antigen presentation (Kageshita, T., et al., Am J Pathol, 1999. 154(3): p. 745-54; Ericsson, C., et al., Invest Ophthalmol Vis Sci, 2001. 42(10): p. 2153-6; Mendez, R., et al., Cancer Immunol Immunother, 2009. 58(9): p. 1507-15), rendering them undetectable by cytotoxic T cells. Particularly in this scenario, natural killer (NK) cells are potential alternatives because of their ability to recognize and kill tumor cells without MHC class I-mediated antigen presentation.

NK cells are innate lymphocytes showing cytotoxicity to tumor and virus-infected cells. NK-mediated killing of target cells is tightly regulated by the balance of signals from activating and inhibitory NK receptors. Activating NK receptors such as NKp30 and NKG2D recognize stress-related cell surface proteins typically induced by viral infection or malignant transformation (referred to as the "induced self" theory). Inhibitory NK receptors such as members of the killer cell immunoglobulin-like receptor (KIR) family recognize MHC class I molecules, therefore cells with missing or aberrantly-expressed MHC class I molecules are recognized by NK cells (the "missing self" theory). These theories are supported by studies showing that NK cells preferentially kill MHC class I-deficient tumor cells. While downregulation of MHC class I molecules in melanomas helps them evade cytotoxic T cells, it makes them more susceptible to NK cell-mediated killing. Moreover, melanoma cells frequently express MICA/B, ligands of the activating NK receptor NKG2D. Indeed, cytotoxicity of NK cells against melanoma cells, particularly ones with low MHC class I molecule expression, has been shown in multiple in vitro studies (Bakker, A. B., et al., J Immunol, 1998. 160(11): p. 5239-45; Carrega, P., et al. PLoS One, 2009. 4(12): p. e8132; Lakshmikanth, T., et al. J Clin Invest, 2009. 119(5): p. 1251-63). These findings led to attempts of ACT for melanoma using NK cells. However, early clinical trials of ACT using autologous NK cells or the human NK cell line NK-92 reported low response rates in melanoma patients (Arai, S., et al., Cytotherapy, 2008. 10(6): p. 625-32; Parkhurst, M. R., et al. Clin Cancer Res, 2011. 17(19): p. 6287-97). Meanwhile, melanoma-infiltrating NK cells show decreased cytotoxicity and diminished expression of cytotoxic effectors and activating NK receptors (Mirjacic Martinovic, K. M., et al., Melanoma Res, 2014. 24(4): p. 295-304). It is therefore hypothesized that certain conditions in melanoma TME inhibit the antitumor activity of NK cells.

Thus, there remains a strong need for methods for enhancing antitumor cytotoxicity of immune cells, such as NK cells or T-cells.

SUMMARY OF THE INVENTION

This disclosure addresses the need mentioned above in a number of aspects. In one aspect, this disclosure provides a method for enhancing antitumor cytotoxicity of immune cells. The method comprises introducing to the immune cells a genetic modification that comprises overexpression of RHEB or a functional fragment thereof, overexpression of LAMP1-RHEB or a functional fragment thereof, overexpression of CA9 or a functional fragment thereof, overexpression of NHE1 or a functional fragment thereof, or a combination thereof. In some embodiments, the immune cells are natural killer cells or T-cells.

In some embodiments, RHEB has an amino acid sequence at least 85% identical to SEQ ID NO: 1, LAMP1-RHEB has an amino acid sequence at least 85% identical to SEQ ID NO: 3, CA9 has an amino acid sequence at least 85% identical to SEQ ID NO: 4, and NHE1 has an amino acid sequence at least 85% identical to SEQ ID NO: 5. In some embodiments, RHEB has an amino acid sequence of SEQ ID NO: 1 or 2, LAMP1-RHEB has an amino acid sequence of SEQ ID NO: 3, CA9 has an amino acid sequence of SEQ ID NO: 4, and NHE1 has an amino acid sequence of SEQ ID NO: 5 or 6.

In some embodiments, the genetic modification is introduced by transfecting the immune cell with a vector (e.g., lentiviral vector) encoding one or more of RHEB or a functional fragment thereof, LAMP1-RHEB or a functional fragment thereof, CA9 or a functional fragment thereof, and NHE1 or a functional fragment thereof.

In another aspect, this disclosure provides a method for enhancing antitumor cytotoxicity of immune cells, comprising introducing to the immune cells a genetic modification that increases a level or activity of mTORC1. In some embodiments, the genetic modification increases the mTOR activity by increasing intracellular pH levels. In some embodiments, the increase in intracellular pH levels is achieved by overexpression of CA9 or a functional fragment thereof. In some embodiments, CA9 has an amino acid sequence at least 85% identical to SEQ ID NO: 4 or has an amino acid sequence of SEQ ID NO: 4.

In another aspect, this disclosure additionally provides a modified immune cell comprising a genetic modification that comprises overexpression of RHEB or a functional fragment thereof, overexpression of LAMP1-RHEB or a functional fragment thereof, overexpression of CA9 or a functional fragment thereof, overexpression of NHE1 or a functional fragment thereof, or combination thereof.

In some embodiments, RHEB has an amino acid sequence at least 85% identical to SEQ ID NO: 1, LAMP1-RHEB has an amino acid sequence at least 85% identical to SEQ ID NO: 3, CA9 has an amino acid sequence at least 85% identical to SEQ ID NO: 4, and NHE1 has an amino acid sequence at least 85% identical to SEQ ID NO: 5. In some embodiments, RHEB has an amino acid sequence of SEQ ID NO: 1 or 2, LAMP1-RHEB has an amino acid sequence of SEQ ID NO: 3, CA9 has an amino acid sequence of SEQ ID NO: 4, and NHE1 has an amino acid sequence of SEQ ID NO: 5 or 6.

Also within the scope of this disclosure is a composition comprising the modified immune cell as described above (e.g., NK killer cells, T-cells).

In yet another aspect, this disclosure further provides a method of treating a cancer or tumor. The method comprises administering a therapeutically effective amount of the immune cells or the composition as described above to a subject in need thereof. In some embodiments, the subject is a mammal, such as a human.

In some embodiments, the immune cell is autologous to the subject. The method may further comprise, before the step of administrating the modified immune cell, obtaining from the subject a sample comprising the immune cell and transfecting the immune cell with a vector encoding one or more of RHEB or a functional fragment thereof, LAMP1-RHEB or a functional fragment thereof, CA9 or a functional fragment thereof, and NHE1 or a functional fragment thereof.

In some embodiments, the method may further comprise, before or after the step of transfecting the immune cell, culturing the immune cell in a medium. In some embodiments, the medium comprises a cytokine (e.g., interleukin-2) to promote the growth of the immune cell.

In some embodiments, the cancer or tumor is a solid tumor. In some embodiments, the cancer or tumor is a hematologic tumor. In some embodiments, the cancer is selected from the group consisting of melanoma, leukemia, lymphoma, multiple myeloma, prostate cancer, neuroblastoma, small cell lung cancer, and breast cancer.

In some embodiments, the immune cell or the composition, as described above, is administered by intravenous infusion, intraperitoneal injection, subcutaneous injection, or intratumoral injection.

In some embodiments, the method further comprises administering to the subject a second therapeutic agent, such as an antitumor agent.

In another aspect, this disclosure additional provides a polypeptide comprising a RHEB polypeptide linked (e.g., covalently linked) to a LAMP1 polypeptide, wherein the RHEB polypeptide is directly linked to the LAMP1 polypeptide or through a linker. In some embodiments, the polypeptide comprises an amino acid sequence at least 85% identical to SEQ ID NO: 3 or an amino acid sequence of SEQ ID NO: 3.

Also provided is a polynucleotide comprising a polynucleotide sequence that encodes the polypeptide described above. In some embodiments, the polynucleotide comprises a polynucleotide sequence having at least 85% sequence identity to the polynucleotide sequence of SEQ ID NO: 9 or a polynucleotide sequence of SEQ ID NO: 9.

Also within the scope of this disclosure is (a) a vector comprising the polynucleotide as described above; (b) a host cell comprising the vector; and (c) a composition comprising the polypeptide, the polynucleotide, the vector or the host cell, as described above.

The foregoing summary is not intended to define every aspect of the disclosure, and additional aspects are described in other sections, such as the following detailed description. The entire document is intended to be related as a unified disclosure, and it should be understood that all combinations of features described herein are contemplated, even if the combination of features are not found together in the same sentence, or paragraph, or section of this document. Other features and advantages of the invention will become apparent from the following detailed description. It should be understood, however, that the detailed description and the specific examples, while indicating specific embodiments of the disclosure, are given by way of illustration only, because various changes and modifications within the spirit and scope of the disclosure will become apparent to those skilled in the art from this detailed description.

BRIEF DESCRIPTION OF THE DRAWINGS

FIG. 1A shows different sensitivities exhibited by human melanoma cell lines, WM1727A, WM3211, WM3629, and WM3681, to NK-92-mediated killing. NK-92 cells were added at effector-target (E:T) ratios of 0.5:1 and 1:1. FIG. 1B shows cytotoxicity of NK-92 cells against human melanoma cell lines WM4237, WM3854, WM852, WM4231, and WM3629 at indicated effector-target (E-T) ratio in a 24-hour in vitro killing assay (N=3). Human melanoma cell lines WM4237, WM3854, WM852, WM4231, and WM3629 were labeled with the fluorescent dye CELLTRACE Yellow before seeded into 24-well plates. NK-92 cells were added at 0.5:1, 1:1, or 3:1 ratio to the melanoma cells. Cells were incubated for 24 hours before being analyzed with a Guava easyCyte flow cytometer. The number of live target cells (CELLTRACE Yellow-positive) was assessed, and percent killing was calculated by comparing the number of live target cells in NK-92-containing wells to that in NK-92-free (control) wells. FIG. 1C shows that NK-92-mediated killing of WM3629 melanoma cells is extracellular pH ($pH_e$)-dependent. Empty vector (EV) or SERPINB9 (PI9) lentivirus-transduced WM3629 melanoma cells (both express EGFP) were co-cultured with NK-92 cells at effector-target ratios of 0.5:1, 1:1, and 2:1 for 24 hours. SERPINB9 serves as a negative control for NK-92-mediated killing by blocking the cytolytic granzyme B released by NK-92 cells.

FIG. 2A shows mTORC1 activity in empty vector (EV)- or constitutively active RHEB (RHEB)-transduced NK-92 cells at indicated extracellular pH ($pH_e$) for 6 hours. mTORC1 activity is indicated by phosphorylation of its targets S6K, S6, and 4EBP1, with total levels of these proteins as controls. Empty vector- or constitutively active RHEB-transduced NK-92 cells were incubated in HEPES/PIPES/$NaHCO_3$-buffered culture media with defined pH for 6 hours. Total proteins were extracted, and phosphorylation of mTORC1 targets S6K, S6, and 4EBP1 were detected by western blot using specific antibodies. FIG. 2B is a set of graphs showing cytotoxicity of empty vector (EV)- or constitutively active RHEB-transduced NK-92 cells to human melanoma cell lines WM3629 (top) and WM4237 (bottom) at indicated extracellular pH ($pH_e$) in a 6-hour in vitro killing assay. N=4, *p<0.001, p<0.01. Human melanoma cell lines WM3629 or WM4237 were labeled with the fluorescent dye CELLTRACE Yellow before seeded into 24-well plates. Empty vector- or constitutively active RHEB-transduced NK-92 cells were added at 3:1 ratio to the melanoma cells. Cells were incubated in HEPES/PIPES/$NaHCO_3$-buffered culture media with defined pH for 6 hours, before being analyzed with a Guava easyCyte flow cytometer. The number of live target cells (CELLTRACE Yellow-positive) was assessed, and percent killing was calculated by comparing the number of live target cells in NK-92-containing wells to that in NK-92-free (control) wells. FIG. 2C is a graph showing K562-induced degranulation of empty vector (EV)- or constitutively active RHEB-transduced NK-92 cells at indicated pH for 6 hours. Phorbol myristate acetate and ionomycin (PMA/iono) induce degranulation and were used as positive controls. N=3, *p<0.001, p<0.01.

FIGS. 3A and 3B show CA9 expression enhanced mTORC1 activity in NK-92 cells at low extracellular pH ($pH_e$). Empty vector (EV) or CA9-transduced NK-92 cells were incubated under $pH_e$-controlled conditions for 6 hours, as described above. Total proteins were extracted from the cells, and phosphorylated mTOR and mTORC1 targets S6K, S6, and 4EBP1 were detected by western blot, with total levels of these proteins as controls. FIG. 3A shows the image of the western blots, and FIG. 3B shows quantification based on the images (using Image Studio software, LI-COR). FIG. 3C shows that CA9 expression enhanced cytotoxicity of NK-92 cells to EM-MESO mesothelioma cells at low extracellular pH ($pH_e$). CELLTRACE Yellow-labeled EM-MESO mesothelioma cells were co-cultured with empty vector (EV) or CA9-transduced NK-92 cells at 1:1 ratio for 12 hours under $pH_e$-controlled conditions. FIG. 3D shows intracellular pH ($pH_i$) of empty vector (EV)- or CA9-transduced NK-92 cells at indicated extracellular pH ($pH_e$). N=3, ***p<0.001, *p<0.05.

FIG. 4A shows ERK phosphorylation in empty vector- or constitutively active NHE1 (with H-to-R mutations of the pH-sensing histidine cluster, based on Webb B A, et al., J Biol Chem. 2016 Nov. 11; 291(46):24096-24104)-transduced NK-92 cells at indicated extracellular pH ($pH_e$) for 6 or 24 hours. Total level of ERK was used as a control. Empty vector (EV) or constitutively active NHE1-transduced NK-92 cells were incubated in HEPES/PIPES/$NaHCO_3$-buffered culture media with defined pH for 6 or 24 hours. Total proteins were extracted, and phosphorylation of ERK was detected by western blot using specific antibodies. FIG. 4B shows intracellular pH ($pH_i$) of empty vector (EV)- or constitutively active NHE1-transduced NK-92 cells at indicated extracellular pH ($pH_e$) in the presence or absence of the specific NHE1 inhibitor cariporide. N=3, multiple comparison with EV, ***p<0.001, *p<0.05. Empty vector- or constitutively active NHE1-transduced NK-92 cells were loaded with the fluorescent pH indicator dye 5-(and-6)-Carboxy SNARF-1 and analyzed for $pH_i$ by flow cytometry. To inhibit NHE1 activity, the NHE1 inhibitor cariporide was added at 20 μM to the pH-defined culture media and the live-cell imaging buffers. FIG. 4C shows K562-induced degranulation of empty vector (EV)- or constitutively active NHE1-transduced NK-92 cells at indicated pH for 6 hours. Phorbol myristate acetate and ionomycin (PMA/iono) induce degranulation and were used as positive controls. N=3, ***p<0.001, *p<0.05. Degranulation of empty vector- or constitutively active NHE1-transduced NK-92 cells was analyzed as described above in FIG. 2C.

FIG. 5A shows expression of LAMP1-RHEB (bottom) and mTORC1 activity after 6-hour incubation at indicated extracellular pH ($pH_e$) (top) in empty vector (EV)-, LAMP1-RFP-, constitutively active RHEB-, or LAMP1-RHEB-transduced WM3629 cells. LAMP1-RHEB is indicated by the high-molecular weight band detected by anti-RHEB antibody. mTORC1 activity is indicated by phosphorylation of its targets S6K, S6, and 4EBP1, with total levels of these proteins as controls. FIG. 5B shows scatter plots of fluorescence intensity of RHEB (X axis) and LAMP2 (lysosome marker, Y axis) in RHEB- or LAMP1-RHEB-transduced WM3629 cells. Plots for two representative cells are shown for each cell type. Dots correspond to pixels in the microscopic images, with Pearson's R below each plot. A higher correlation indicates more colocalization between RHEB and lysosomes.

DETAILED DESCRIPTION OF THE INVENTION

Figure 1A:
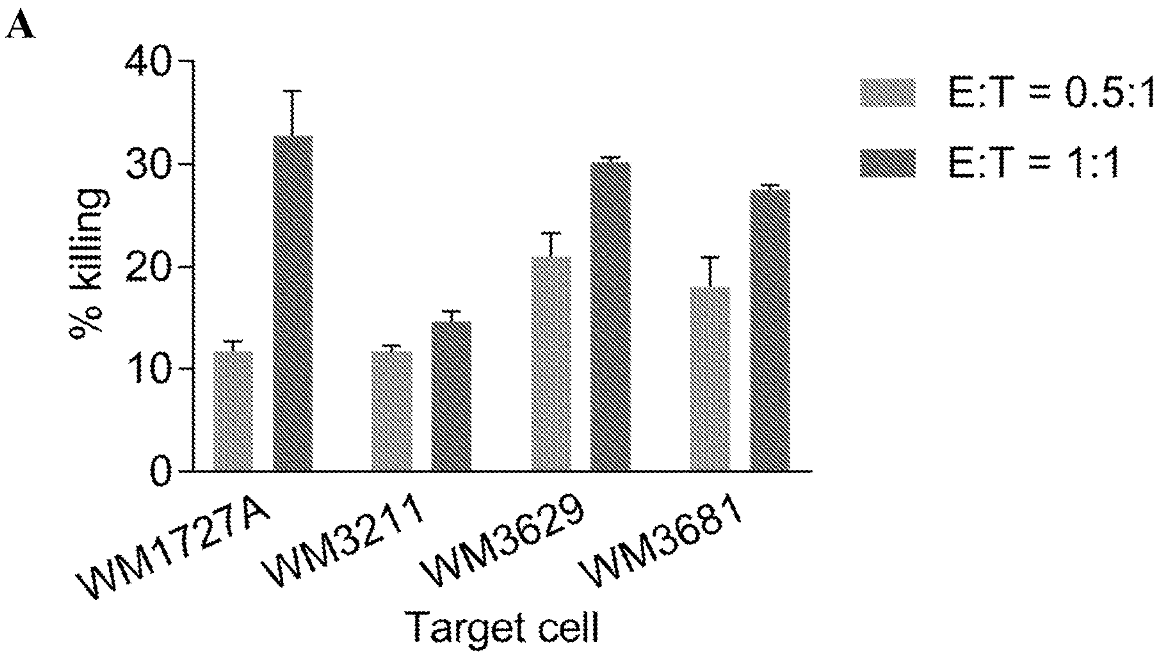
FIGS. 1A, 1B, and 1C (collectively "FIG. 1") are a set of diagrams showing NK-92-mediated killing of melanoma cells.

While melanoma can be treated with immunotherapies, only a subset of patients responds due to immune evasion of the tumor by a means such as downregulation of major histocompatibility complex (MHC) class I molecules. To overcome this issue, adoptive transfer immunotherapy with natural killer (NK) cells have been proposed for melanoma, because NK cells do not depend on MHC class I molecules for recognition of melanoma. However, NK cells in clinical trials did not achieve sustainable response in patients, implying additional mechanisms in melanoma that suppress immune cell functions. One such mechanism is that the acidic tumor microenvironment (TME) may suppress viability and cytotoxicity of primary NK cells, yet the mechanism is not fully understood.

This disclosure provides a method for enhancing antitumor cytotoxicity of immune cells, for example, by introducing a genetic modification to the immune cells to increase the level or activity of mTORC1. As demonstrated herein, cytotoxicity of NK cells under acidic conditions was unexpectedly rescued/enhanced through direct activation of mTORC1 by overexpressing RHEB, including a constitutively active mutant of RHEB (RHEB-CA) and a LAMP1-RHEB fusion protein. This disclosure further demonstrates cytotoxicity of NK cells under acidic conditions could be rescued/enhanced by increasing intracellular pH, for example, through overexpressing pH regulatory protein CA9 in NK cells.

This disclosure thus presents an effective strategy for engineering immune cells in immunotherapy towards acid resistance to increase their efficacy in treating tumors such as melanoma.

I. METHODS FOR ENHANCING ANTITUMOR CYTOTOXICITY OF IMMUNE CELLS

In some embodiments, this disclosure provides a method for enhancing antitumor cytotoxicity of immune cells by introducing to the immune cells a genetic modification that comprises overexpression of RHEB or a functional fragment thereof, overexpression of LAMP1-RHEB or a functional fragment thereof, overexpression of CA9 or a functional fragment thereof, overexpression of NHE1 or a functional fragment thereof, or a combination thereof. In some embodiments, the immune cells are natural killer cells or T-cells.

Also within the scope of this disclosure are the variants, mutants, and homologs with significant identity to RHEB, LAMP1-RHEB, CA9, or NHE1. For example, such variants and homologs may have sequences with at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the sequences of RHEB, LAMP1-RHEB, CA9, and NHE1 described herein.

A peptide or polypeptide "fragment" as used herein refers to a less than full-length peptide, polypeptide or protein. For example, a peptide or polypeptide fragment can have at least about 3, at least about 4, at least about 5, at least about 10, at least about 20, at least about 30, at least about 40 amino acids in length, or single unit lengths thereof. For example, fragment may be 6, 7, 8, 9, 10, 11, 12, 13, 14, 15, 16, 17, or more amino acids in length. There is no upper limit to the size of a peptide fragment. However, in some embodiments, peptide fragments can be less than about 500 amino acids, less than about 400 amino acids, less than about 300 amino acids or less than about 250 amino acids in length.

In some embodiments, RHEB has an amino acid sequence at least 75% (e.g., 80%, 85%, 90%, 95%, 99%) identical to SEQ ID NO: 1 (TABLE 1), LAMP1-RHEB has an amino acid sequence at least 75% (e.g., 80%, 85%, 90%, 95%, 99%) identical to SEQ ID NO: 3, CA9 has an amino acid sequence at least 75% (e.g., identical to SEQ ID NO: 4, and NHE1 has an amino acid sequence at least 75% (e.g., 80%, 85%, 90%, 95%, 99%) identical to SEQ ID NO: 5.

In some embodiments, RHEB has an amino acid sequence at least 75% (e.g., 80%, 85%, 90%, 95%, 99%) identical to SEQ ID NO: 2, LAMP1-RHEB has an amino acid sequence at least 75% (e.g., 80%, 85%, 90%, 95%, 99%) identical to SEQ ID NO: 3, while the substitution(s) (e.g., a substitution at N153, for example, N153T) conferring RHEB constitutive activity are retained. In some embodiments, NHE1 has an amino acid sequence at least 75% (e.g., 80%, 85%, 90%, 95%, 99%) identical to SEQ ID NO: 6, while the substitution(s) (e.g., substitution at H540, H543, H544, and/or H545, for example, H540R, H543R, H544R, and/or H545R) conferring NHE1 constitutive activity are retained.

In some embodiments, RHEB has an amino acid sequence of SEQ ID NO: 1 or 2, LAMP1-RHEB has an amino acid sequence of SEQ ID NO: 3, CA9 has an amino acid sequence of SEQ ID NO: 4, and NHE1 has an amino acid sequence of SEQ ID NO: 5 or 6.

In some embodiments, RHEB has a substitution at N153, such as an N153T substitution. In some embodiments, NHE1 has a substitution at H540, such as an H540R substitution. In some embodiments, NHE1 has a substitution at one or more of H543, H544, and H545, such as an H543R substitution, an H544R substitution, an H545R substitution, or a combination thereof.

LAMP1-RHEB is a fusion protein in which LAMP1 is linked (e.g., covalently linked) to RHEB. LAMP1 is a protein that associates with lysosome membranes. It directs RHEB to the lysosome, where RHEB interacts with mTORC1, presumably independent of intracellular lysosome distribution.

The term "fusion protein" or "fusion polypeptide" means a protein created by joining two or more polypeptide sequences together. The fusion polypeptides encompassed in this invention include translation products of a chimeric gene construct that joins the nucleic acid sequences encoding a first polypeptide with the nucleic acid sequence encoding a second polypeptide to form a single open reading frame. In other words, a "fusion polypeptide" or "fusion protein" is a recombinant protein of two or more proteins which are joined by a peptide bond or via several peptides. The fusion protein may also comprise a peptide linker between the two domains.

In some embodiments, LAMP1-RHEB may include LAMP1 or a fragment/variant thereof linked (e.g, covalently linked) to the N- or C-terminus of RHEB or a fragment/variant thereof, directly or via a linker (e.g., peptide linker). The term "linker" refers to any means, entity, or moiety used to join two or more entities. A linker can be a covalent linker or a non-covalent linker. Examples of covalent linkers include covalent bonds or a linker moiety covalently attached to one or more of the proteins or domains to be linked. The linker can also be a non-covalent bond, e.g., an organometallic bond through a metal center such as a platinum atom. For covalent linkages, various functionalities can be used, such as amide groups, including carbonic acid derivatives, ethers, esters, including organic and inorganic esters, amino, urethane, urea and the like. To provide for linking, the domains can be modified by oxidation, hydroxylation, substitution, reduction etc. to provide a site for coupling. Methods for conjugation are well known by persons skilled in the art and are encompassed for use in the present invention. Linker moieties include, but are not limited to, chemical linker moieties, or for example, a peptide linker moiety (a linker sequence).

In some embodiments, the linker can be a peptide linker and a non-peptide linker. In some embodiments, the linker can be GGGTM (SEQ ID NO: 13). Other examples of the peptide linker may include, without limitation, [S(G)n]m or [S(G)n]mS, where n may be an integer between 1 and 20, and m may be an integer between 1 and 10. For example, the peptide linker can be SG (SEQ ID NO: 14), SGS (SEQ ID NO: 15), SGG (SEQ ID NO: 16), SGGS (SEQ ID NO: 17), SGGG (SEQ ID NO: 18), SGGGS (SEQ ID NO: 19), SGGGG (SEQ ID NO: 20), SGGG GS (SEQ ID NO: 21), SGGGGG (SEQ ID NO: 22), SGGGGGS (SEQ ID NO: 23), SGGGG GG (SEQ ID NO: 24), and SG GSGGGGS (SEQ ID NO: 25).

As used herein, the term "non-peptide linker" refers to a biocompatible polymer composed of two or more repeating units linked to each other, in which the repeating units are linked to each other by any non-peptide covalent bond. This non-peptidyl linker may have two ends or three ends. Examples of the non-peptidyl linker may include, without limitation, polyethylene glycol, polypropylene glycol, a copolymer of ethylene glycol with propylene glycol, polyoxyethylated polyol, polyvinyl alcohol, polysaccharide, dextran, polyvinyl ethyl ether, biodegradable polymers such as polylactic acid (PLA) and polylactic-glycolic acid (PLGA), lipid polymers, chitins, hyaluronic acid, and combinations thereof.

In another aspect, this disclosure provides a method for enhancing antitumor cytotoxicity of immune cells, comprising introducing to the immune cells a genetic modification that increases the level or activity of mTORC1. In some embodiments, the genetic modification increases the mTOR activity by increasing intracellular pH levels.

In some embodiments, the increase in intracellular pH levels is achieved by overexpression of CA9 or a functional fragment thereof. In some embodiments, CA9 has an amino acid sequence at least 75% (e.g., 80%, 85%, 90%, 95%, 99%) identical to SEQ ID NO: 4 or has an amino acid sequence of SEQ ID NO: 4.

TABLE 1

| REPRESENTATIVE SEQUENCES | | |
|---|---|---|
| SEQ ID NO | SEQUENCES | OTHER INFORMATION |
| SEQ ID NO: 1 | MPQSKSRKIAILGYRSVGKSSLTIQFVEGQFVDSYDPTIENTFTKLIT<br>VNGQEYHLQLVDTAGQDEYSIFPQTYSIDINGYILVYSVTSIKSFEVI<br>KVIHGKLLDMVGKVQIPIMLVGNKKDLHMERVISYEEGKALAESW<br>NAAFLESSAKENQTAVDVFRRIILEAEKMDGAASQGKSSCSVM | RHEB<br>Wild-type |
| SEQ ID NO: 2 | MDYKDDDDKPQSKSRKIAILGYRSVGKSSLTIQFVEGQFVDSYDPTI<br>ENTFTKLITVNGQEYHLQLVDTAGQDEYSIFPQTYSIDINGYILVYSV<br>TSIKSFEVIKVIHGKLLDMVGKVQIPIMLVGNKKDLHMERVISYEEG<br>KALAESWNAAFLESSAKETQTAVDVFRRIILEAEKMDGAASQGKSS<br>CSVM | RHEB<br>constitutively<br>active mutant |
| SEQ ID NO: 3 | MAAPGARRPLLLLLLAGLAHSAPALFEVKDNNGTACIMASFSASFL<br>TTYEAGHVSKVSNMTLPASAEVLKNSSSCGEKNASEPTLAITFGEG<br>YLLKLTFTKNTTRYSVQHMYFTYNLSDTQFFPNASSKGPDTVDSTT<br>DIKADINKTYRCVSDIRVYMKNVTIVLWDATIQAYLPSSNFSKEETR<br>CPQDQPSPTTGPPSPSPPLVPTNPSVSKYNVTGDNGTCLLASMALQL<br>NITYMKKDNTTVTRAFNINPSDKYSGTCGAQLVTLKVGNKSRVLEL<br>QFGMNATSSLFFLQGVQLNMTLPDAIEPTFSTSNYSLKALQASVGNS<br>YKCNSEEHIFVSKALALNVFSVQVQAFRVESDRFGSVEECVQDGNN<br>MLIPIAVGGALAGLVLIVLIAYLIGRKRSHAGYQTI***GGGTM*****DYKDD**<br>**DDK**PQSKSRKIAILGYRSVGKSSLTIQFVEGQFVDSYDPTIENTFTKL<br>ITVNGQEYHLQLVDTAGQDEYSIFPQTYSIDINGYILVYSVTSIKSFE<br>VIKVIHGKLLDMVGKVQIPIMLVGNKKDLHMERVISYEEGKALAES<br>WNAAFLESSAKETQTAVDVFRRIILEAEKMDGAASQGKSSCSVM | LAMP1-<br>RHEB<br>Linker:<br>GGGTM<br>FLAG-tag:<br>DYKDD |
| SEQ ID NO: 4 | MAPLCPSPWLPLLIPAPAPGLTVQLLLSLLLLVPVHPQRLPRMQEDS<br>PLGGGSSGEDDPLGEEDLPSEEDSPREEDPPGEEDLPGEEDLPGEEDL<br>PEVKPKSEEEGSLKLEDLPTVEAPGDPQEPQNNAHRDKEGDDQSH<br>WRYGGDPPWPRVSPACAGRFQSPVDIRPQLAAFCPALRPLELLGFQ<br>LPPLPELRLRNNGHSVQLTLPPGLEMALGPGREYRALQLHLHWGA<br>AGRPGSEHTVEGHRFPAEIHVVHLSTAFARVDEALGRPGGLAVLAA<br>FLEEGPEENSAYEQLLSRLEEIAEEGSETQVPGLDISALLPSDFSRYFQ<br>YEGSLTTPPCAQGVIWTVFNQTVMLSAKQLHTLSDTLWGPGDSRL<br>QLNFRATQPLNGRVIEASFPAGVDSSPRAAEPVQLNSCLAAGDILAL<br>VFGLLFAVTSVAFLVQMRRQHRRGTKGGVSYRPAEVAETGA | CA9<br>Wild-type |
| SEQ ID NO: 5 | MVLRSGICGLSPHRIFPSLLVVVALVGLLPVLRSHGLQLSPTASTIRS<br>SEPPRERSIGDVTTAPPEVTPESRPVNHSVTDHGMKPRKAFPVLGID<br>YTHVRTPFEISLWILLACLMKIGFHVIPTISSIVPESCLLIVVGLLVGG<br>LIKGVGETPPFLQSDVFFLFLLPPIILDAGYFLPLRQFTENLGTILIFAV<br>VGTLWNAFFLGGLMYAVCLVGGEQINNIGLLDNLLFGSIISAVDPV<br>AVLAVFEEIHINELLHILVFGESLLNDAVTVVLYHLFEEFANYEHVGI<br>VDIFLGFLSFFVVALGGVLVGVVYGVIAAFTSRFTSHIRVIEPLFVFL<br>YSYMAYLSAELFHLSGIMALIASGVVMRPYVEANISHKSHTTIKYFL<br>KMWSSVSETLIFIFLGVSTVAGSHHWNWTFVISTLLFCLIARVLGVL<br>GLTWFINKFRIVKLTPKDQFHAYGGLRGAIAFSLGYLLDKKHFPMC<br>DLFLTAIITVIFFTVFVQGMTIRPLVDLLAVKKKQETKRSINEEIHTQF<br>LDHLLTGIEDICGHYGHHHWKDKLNRFNKKYVKKCLIAGERSKEP<br>QLIAFYHKMEMKQAIELVESGGMGKIPSAVSTVSMQNIHPKSLPSER<br>ILPALSKDKEEEIRKILRNNLQKTRQRLRSYNRHTLVADPYEEAWN<br>QMLLRRQKARQLEQKINNYLTVPAHKLDSPTMSRARIGSDPLAYEP<br>KEDLPVITIDPASPQSPESVDLVNEELKGKVLGLSRDPAKVAEEDED<br>DDGGIMMRSKETSSPGTDDVFTPAPSDSPSSQRIQRCLSDPGPHPEPG<br>EGEPFFFPKGQ | NHE1<br>Wild-type |
| SEQ ID NO: 6 | MVLRSGICGLSPHRIFPSLLVVVALVGLLPVLRSHGLQLSPTASTIRS<br>SEPPRERSIGDVTTAPPEVTPESRPVNHSVTDHGMKPRKAFPVLGID<br>YTHVRTPFEISLWILLACLMKIGFHVIPTISSIVPESCLLIVVGLLVGG<br>LIKGVGETPPFLQSDVFFLFLLPPIILDAGYFLPLRQFTENLGTILIFAV<br>VGTLWNAFFLGGLMYAVCLVGGEQINNIGLLDNLLFGSIISAVDPV<br>AVLAVFEEIHINELLHILVFGESLLNDAVTVVLYHLFEEFANYEHVGI | NHE1<br>constitutively<br>active mutant |

TABLE 1-continued

REPRESENTATIVE SEQUENCES

| SEQ ID NO | SEQUENCES | OTHER INFORMATION |
|---|---|---|
| | VDIFLGFLSFFVVALGGVLVGVVYGVIAAFTSRFTSHIRVIEPLFVFL<br>YSYMAYLSAELFHLSGIMALIASGVVMRPYVEANISHKSHTTIKYFL<br>KMWSSVSETLIFIFLGVSTVAGSHEIWNWTFVISTLLFCLIARVLGVL<br>GLTWFINKFRIVKLTPKDQFIIAYGGLRGAIAFSLGYLLDKKHFPMC<br>DLFLTAIITVIFFTVFVQGMTIRPLVDLLAVKKKQETKRSINEEIHTQF<br>LDHLLTGIEDICGRYGRRRWKDKLNRFNKKYVKKCLIAGERSKEPQ<br>LIAFYHKMEMKQAIELVESGGMGKIPSAVSTVSMQNIHPKSLPSERI<br>LPALSKDKEEEIRKILRNNLQKTRQRLRSYNRHTLVADPYEEAWNQ<br>MLLRRQKARQLEQKINNYLTVPAFIKLDSPTMSRARIGSDPLAYEPK<br>EDLPVITIDPASPQSPESVDLVNEELKGKVLGLSRDPAKVAEEDEDD<br>DGGIMMRSKETSSPGTDDVFTPAPSDSPSSQRIQRCLSDPGPHPEPGE<br>GEPFFPKGQ | |
| SEQ ID NO: 7 | ATGCCGCAGTCCAAGTCCCGGAAGATCGCGATCCTGGGCTACCG<br>GTCTGTGGGGAAATCCTCATTGACGATTCAATTTGTTGAAGGCCA<br>ATTTGTGGACTCCTACGATCCAACCATAGAAAACACTTTTACAA<br>AGTTGATCACAGTAAATGGACAAGAATATCATCTTCAACTTGTA<br>GACACAGCCGGGCAAGATGAATATTCTATCTTTCCTCAGACATA<br>CTCCATAGATATTAATGGCTATATTCTTGTGTATTCTGTTACATC<br>AATCAAAAGTTTTGAAGTGATTAAAGTTATCCATGGCAAATTGTT<br>GGATATGGTGGGGAAAGTACAAATACCTATTATGTTGGTTGGGA<br>ATAAGAAAGACCTGCATATGGAAAGGGTGATCAGTTATGAAGA<br>AGGGAAAGCTTTGGCAGAATCTTGGAATGCAGCTTTTTTGGAAT<br>CTTCTGCTAAAGAAAATCAGACTGCTGTGGATGTTTTTCGAAGG<br>ATAATTTTGGAGGCAGAAAAAATGGACGGGGCAGCTTCACAAG<br>GCAAGTCTTCATGCTCGGTGATGTGA | RHEB<br>Wild-type |
| SEQ ID NO: 8 | ATGGATTACAAGGATGACGATGACAAGCCGCAGTCCAAGTCCCG<br>GAAGATCGCGATCCTGGGCTACCGGTCTGTGGGGAAATCCTCAT<br>TGACGATTCAATTTGTTGAAGGCCAATTTGTGGACTCCTACGATC<br>CAACCATAGAAAACACTTTTACAAAGTTGATCACAGTAAATGGA<br>CAAGAATATCATCTTCAACTTGTAGACACAGCCGGGCAAGATGA<br>ATATTCTATCTTTCCTCAGACATACTCCATAGATATTAATGGCTA<br>TATTCTTGTGTATTCTGTTACATCAATCAAAAGTTTTGAAGTGAT<br>TAAAGTTATCCATGGCAAATTGTTGGATATGGTGGGGAAAGTAC<br>AAATACCTATTATGTTGGTTGGGAATAAGAAAGACCTGCATATG<br>GAAAGGGTGATCAGTTATGAAGAAGGGAAAGCTTTGGCAGAAT<br>CTTGGAATGCAGCTTTTTTGGAATCTTCTGCTAAAGAAACTCAGA<br>CTGCTGTGGATGTTTTTCGAAGGATAATTTTGGAGGCAGAAAAA<br>ATGGACGGGGCAGCTTCACAAGGCAAGTCTTCATGCTCGGTGAT<br>GTGA | RHEB<br>constitutively<br>active mutant |
| SEQ ID NO: 9 | ATGGCGGCCCCGGGCGCCCGGCGGCCGCTGCTCCTGTTGCTGCT<br>GGCAGGCCTTGCACACAGCGCCCCAGCACTGTTCGAGGTGAAAG<br>ACAACAACGGCACAGCGTGTATAATGGCCAGCTTCTCTGCCTCC<br>TTTCTGACCACCTATGAGGCTGGACATGTTTCTAAGGTCTCGAAT<br>ATGACCCTGCCAGCCTCTGCAGAAGTCCTGAAGAATAGCAGCTC<br>TTGTGGTGAAAAGAATGCTTCTGAGCCCACCCTCGCAATCACCTT<br>TGGAGAAGGATATTTACTGAAACTCACCTTCACAAAAAACACAA<br>CACGTTACAGTGTCCAGCACATGTATTTCACATATAACCTGTCAG<br>ACACACAATTCTTTCCCAATGCCAGCTCCAAAGGGCCCGACACT<br>GTGGATTCCACAACTGACATCAAGGCAGACATCAACAAAACATA<br>CCGATGTGTCAGCGACATCAGGGTCTACATGAAGAATGTGACCA<br>TTGTGCTCTGGGACGCTACTATCCAGGCCTACCTGCCGAGTAGCA<br>ACTTCAGCAAGGAAGAGACACGCTGCCCACAGGATCAACCTTCC<br>CCAACTACTGGGCCACCCAGCCCCTCACCACCACTTGTGCCCAC<br>AAACCCCAGTGTGTCCAAGTACAATGTGACTGGTGACAATGGAA<br>CCTGCCTGCTGGCCTCTATGGCACTGCAACTCAACATCACCTACA<br>TGAAGAAGGACAACACGACTGTGACCAGAGCATTCAACATCAAC<br>CCAAGTGACAAATATAGTGGGACTTGCGGTGCCCAGTTGGTGAC<br>CCTGAAGGTGGGGAACAAGAGCAGAGTCCTGGAGCTGCAGTTTG<br>GGATGAATGCCACTTCTAGCCTGTTTTTCCTGCAAGGAGTTCAGT<br>TGAACATGACTCTTCCTGATGCCATAGAGCCCACGTTCAGCACCT<br>CCAACTATTCCCTGAAAGCTCTTCAGGCCAGTGTCGGCAACTCAT<br>ACAAGTGCAACAGTGAGGAGCACATCTTTGTCAGCAAGGCGCTC<br>GCCCTCAATGTCTTCAGCGTGCAAGTCCAGGCTTTCAGGGTAGA<br>AAGTGACAGGTTTGGGTCTGTGGAAGAGTGTGTACAGGACGGTA<br>ACAACATGCTGATCCCCATTGCTGTGGGCGGGGCCCTGGCAGGG<br>CTGGTCCTCATCGTCCTCATCGCCTACCTCATCGGCAGGAAGAGG<br>AGTCACGCGGGCTATCAGACCATC***GGAGGCGGCACCATG*****GATTA**<br>**CAAGGATGACGATGACAAG**CCGCAGTCCAAGTCCCGGAAGATC<br>GCGATCCTGGGCTACCGGTCTGTGGGGAAATCCTCATTGACGAT<br>TCAATTTGTTGAAGGCCAATTTGTGGACTCCTACGATCCAACCAT<br>AGAAAACACTTTTACAAAGTTGATCACAGTAAATGGACAAGAAT<br>ATCATCTTCAACTTGTAGACACAGCCGGGCAAGATGAATATTCT | LAMP1-<br>RHEB |

TABLE 1-continued

REPRESENTATIVE SEQUENCES

| SEQ ID NO | SEQUENCES | OTHER INFORMATION |
|---|---|---|
| | ATCTTTCCTCAGACATACTCCATAGATATTAATGGCTATATTCTT<br>GTGTATTCTGTTACATCAATCAAAAGTTTTGAAGTGATTAAAGTT<br>ATCCATGGCAAATTGTTGGATATGGTGGGGAAAGTACAAATACC<br>TATTATGTTGGTTGGGAATAAGAAAGACCTGCATATGGAAAGGG<br>TGATCAGTTATGAAGAAGGGAAAGCTTTGGCAGAATCTTGGAAT<br>GCAGCTTTTTTGGAATCTTCTGCTAAAGAAACTCAGACTGCTGTG<br>GATGTTTTTCGAAGGATAATTTTGGAGGCAGAAAAAAATGGACGG<br>GGCAGCTTCACAAGGCAAGTCTTCATGCTCGGTGATGTGA | |
| SEQ ID NO: 10 | ATGGCTCCCCTGTGCCCCAGCCCCTGGCTCCCTCTGTTGATCCCG<br>GCCCCTGCTCCAGGCCTCACTGTGCAACTGCTGCTGTCACTGCTG<br>CTTCTGGTGCCTGTCCATCCCCAGAGGTTGCCCCGGATGCAGGA<br>GGATTCCCCCTTGGGAGGAGGCTCTTCTGGGGAAGATGACCCAC<br>TGGGCGAGGAGGATCTGCCCAGTGAAGAGGATTCACCCAGAGA<br>GGAGGATCCACCCGGAGAGGAGGATCTACCTGGAGAGGAGGAT<br>CTACCTGGAGAGGAGGATCTACCTGAAGTTAAGCCTAAATCAGA<br>AGAAGAGGGCTCCCTGAAGTTAGAGGATCTACCTACTGTTGAGG<br>CTCCTGGAGATCCTCAAGAACCCCAGAATAATGCCCACAGGGAC<br>AAAGAAGGGGATGACCAGAGTCATTGGCGCTATGGAGGCGACC<br>CGCCCTGGCCCCGGGTGTCCCCAGCCTGCGCGGGCCGCTTCCAG<br>TCCCCGGTGGATATCCGCCCCCAGCTCGCCGCCTTCTGCCCGGCC<br>CTGCGCCCCCTGGAACTCCTGGGCTTCCAGCTCCCGCCGCTCCCA<br>GAACTGCGCCTGCGCAACAATGGCCACAGTGTGCAACTGACCCT<br>GCCTCCTGGGCTAGAGATGGCTCTGGGTCCCGGGCGGGAGTACC<br>GGGCTCTGCAGCTGCATCTGCACTGGGGGGCTGCAGGTCGTCCG<br>GGCTCGGAGCACACTGTGGAAGGCCACCGTTTCCCTGCCGAGAT<br>CCACGTGGTTCACCTCAGCACCGCCTTTGCCAGAGTTGACGAGG<br>CCTTGGGGCGCCCGGGAGGCCTGGCCGTGTTGGCCGCCTTTCTG<br>GAGGAGGGCCCGGAAGAAAACAGTGCCTATGAGCAGTTGCTGTC<br>TCGCTTGGAAGAAATCGCTGAGGAAGGCTCAGAGACTCAGGTCC<br>CAGGACTGGACATATCTGCACTCCTGCCCTCTGACTTCAGCCGCT<br>ACTTCCAATATGAGGGGTCTCTGACTACACCGCCCTGTGCCCAG<br>GGTGTCATCTGGACTGTGTTTAACCAGACAGTGATGCTGAGTGCT<br>AAGCAGCTCCACACCCTCTCTGACACCCTGTGGGGACCTGGTGA<br>CTCTCGGCTACAGCTGAACTTCCGAGCGACGCAGCCTTTGAATG<br>GGCGAGTGATTGAGGCCTCCTTCCCTGCTGGAGTGGACAGCAGT<br>CCTCGGGCTGCTGAGCCAGTCCAGCTGAATTCCTGCCTGGCTGCT<br>GGTGACATCCTAGCCCTGGTTTTTGGCCTCCTTTTTGCTGTCACC<br>AGCGTCGCGTTCCTTGTGCAGATGAGAAGGCAGCACAGAAGGGG<br>AACCAAAGGGGGTGTGAGCTACCGCCCAGCAGAGGTAGCCGAG<br>ACTGGAGCCTAG | CA9<br>Wild-type |
| SEQ ID NO: 11 | ATGGTGCTGAGGAGTGGTATCTGCGGCCTGTCCCCCCATAGGAT<br>ATTTCCAAGTTTGCTTGTAGTTGTAGCTCTCGTCGGATTGCTCCCT<br>GTTCTGCGCTCTCACGGACTGCAACTGTCTCCGACTGCTTCCACT<br>ATTCGGTCATCTGAGCCACCGCGCGAGAGGAGCATCGGGGATGT<br>TACTACAGCACCACCAGAGGTCACCCCCGAGTCACGACCAGTGA<br>ACCACTCCGTCACTGATCATGGGATGAAGCCGCGGAAGGCTTTC<br>CCCGTGCTCGGGATTGATTACACGCATGTACGGACACCTTTTGAA<br>ATCTCACTCTGGATCCTGTTGGCGTGTCTCATGAAAATCGGGTTT<br>CATGTAATACCGACGATTTCTTCCATCGTGCCAGAGTCTTGTCTC<br>CTCATTGTGGTCGGTCTCCTCGTTGGCGGTCTCATCAAGGGAGTT<br>GGCGAGACACCGCCGTTTTTGCAATCAGATGTATTCTTTTTGTTT<br>CTTCTGCCCCCAATAATTCTTGATGCAGGGTATTTCTTGCCGCTC<br>AGACAGTTTACTGAGAACCTTGGGACTATACTTATATTCGCGGTA<br>GTAGGAACCCTCTGGAACGCCTTTTTCCTGGGAGGGTTGATGTAC<br>GCTGTATGTCTCGTCGGTGGAGAGCAAATTAACAATATTGGTCT<br>GTTGGACAATCTTTTGTTCGGCTCCATAATCAGCGCTGTCGATCC<br>AGTCGCCGTGCTCGCTGTATTCGAGGAAATCCACATCAACGAAC<br>TTCTTCATATACTCGTTTTCGGTGAAAGTCTTCTCAATGATGCCG<br>TGACTGTAGTTCTTTACCATCTCTTCGAAGAGTTCGCCAACTATG<br>AGCACGTTGGAATAGTCGATATTTTCCTTGGGTTTCTCTCTTTCTT<br>CGTCGTTGCCCTCGGAGGAGTCTTGGTAGGCGTCGTCTACGGCGT<br>CATAGCAGCCTTTACTTCTAGGTTTACGTCTCACATACGCGTGAT<br>TGAGCCGTTGTTTGTTTTTCTGTATTCCTATATGGCCTATTTGAGT<br>GCCGAGCTTTTTCATCTTAGCGGTATAATGGCCCTTATCGCGTCT<br>GGGGTTGTCATGCGCCCATATGTCGAGGCGAATATAAGTCACAA<br>ATCCCATACCACGATTAAATATTTCCTCAAAATGTGGTCAAGCGT<br>TTCAGAAACCCTTATATTCATATTCCTGGGAGTCAGCACAGTAGC<br>GGGCTCCCATCACTGGAACTGGACATTCGTAATATCTACGTTGCT<br>CTTTTGCCTGATAGCCAGAGTTCTGGGCGTGCTCGGACTGACTTG<br>GTTTATTAACAAATTCAGAATTGTTAAACTGACGCCTAAAGACC<br>AGTTCATCATAGCATATGGAGGTTTGCGCGGGGCAATCGCATTC<br>AGTCTGGGGTATCTCCTCGACAAGAAGCACTTCCCCATGTGCGA<br>TCTGTTTTTGACCGCGATCATCACAGTCATATTTTTTACGGTTTTT | NHE1<br>Wild-type |

TABLE 1-continued

REPRESENTATIVE SEQUENCES

| SEQ ID NO | SEQUENCES | OTHER INFORMATION |
|---|---|---|
| | GTACAGGGGATGACCATCAGGCCACTCGTTGATCTTTTGGCGGT | |
| | CAAAAAAAAACAAGAGACGAAACGAAGTATAAATGAAGAGATA | |
| | CATACTCAGTTCTTGGACCACTTGCTGACCGGGATAGAGGACAT | |
| | TTGTGGCCACTATGGTCATCATCACTGGAAGGATAAACTGAATC | |
| | GGTTTAACAAAAAATATGTGAAAAAATGCTTGATCGCCGGGGAA | |
| | CGGTCTAAAGAACCACAGCTTATAGCCTTCTATCATAAAATGGA | |
| | GATGAAGCAGGCGATAGAGCTGGTGGAATCCGGAGGAATGGGA | |
| | AAGATACCCAGCGCTGTCTCAACCGTGTCTATGCAAAATATCCA | |
| | TCCGAAGTCCCTTCCATCTGAGCGAATCCTGCCCGCCCTCAGCAA | |
| | GGACAAAGAGGAGGAGATTCGGAAAATTCTGAGGAATAACTTG | |
| | CAGAAGACTAGACAGCGCCTCAGATCCTATAACCGACACACCCT | |
| | GGTGGCCGACCCCTATGAGGAAGCCTGGAACCAGATGTTGCTTC | |
| | GACGGCAAAAAGCTCGACAATTGGAGCAAAAGATCAATAACTA | |
| | TCTCACCGTCCCTGCTCACAAACTTGACTCTCCCACTATGTCTCG | |
| | AGCCAGGATAGGATCTGACCCCCTGGCGTACGAGCCAAAAGAG | |
| | GATTTGCCTGTCATTACGATAGATCCGGCCTCCCCGCAGTCTCCC | |
| | GAGTCCGTAGACCTGGTTAACGAGGAACTTAAGGGCAAAGTTCT | |
| | GGGCCTTAGTCGGGATCCGGCAAAGGTTGCTGAGGAGGACGAA | |
| | GATGATGATGGGGGTATTATGATGAGGTCAAAAGAAACAAGTTC | |
| | CCCCGGTACGGACGATGTATTCACGCCGGCGCCTTCTGACTCCCC | |
| | AAGCTCTCAACGCATACAGCGGTGCCTGAGTGACCCGGGGCCCC | |
| | ATCCGGAGCCGGGTGAAGGGGAGCCGTTTTTTCCTAAAGGCCAA | |
| | TAG | |
| SEQ ID NO: 12 | ATGGTGCTGAGGAGTGGTATCTGCGGCCTGTCCCCCCATAGGAT | NHE1 constitutively active mutant |
| | ATTTCCAAGTTTGCTTGTAGTTGTAGCTCTCGTCGGATTGCTCCCT | |
| | GTTCTGCGCTCTCACGGACTGCAACTGTCTCCGACTGCTTCCACT | |
| | ATTCGGTCATCTGAGCCACCGCGCGAGAGGAGCATCGGGGATGT | |
| | TACTACAGCACCACCAGAGGTCACCCCCGAGTCACGACCAGTGA | |
| | ACCACTCCGTCACTGATCATGGGATGAAGCCGCGGAAGGCTTTC | |
| | CCCGTGCTCGGGATTGATTACACGCATGTACGGACACCTTTTGAA | |
| | ATCTCACTCTGGATCCTGTTGGCGTGTCTCATGAAAATCGGGTTT | |
| | CATGTAATACCGACGATTTCTTCCATCGTGCCAGAGTCTTGTCTC | |
| | CTCATTGTGGTCGGTCTCCTCGTTGGCGGTCTCATCAAGGGAGTT | |
| | GGCGAGACACCGCCGTTTTTGCAATCAGATGTATTCTTTTTGTTT | |
| | CTTCTGCCCCCAATAATTCTTGATGCAGGGTATTTCTTGCCGCTC | |
| | AGACAGTTTACTGAGAACCTTGGGACTATACTTATATTCGCGGTA | |
| | GTAGGAACCCTCTGGAACGCCTTTTTCCTGGGAGGGTTGATGTAC | |
| | GCTGTATGTCTCGTCGGTGGAGAGCAAATTAACAATATTGGTCT | |
| | GTTGGACAATCTTTTGTTCGGCTCCATAATCAGCGCTGTCGATCC | |
| | AGTCGCCGTGCTCGCTGTATTCGAGGAAATCCACATCAACGAAC | |
| | TTCTTCATATACTCGTTTTCGGTGAAAGTCTTCTCAATGATGCCG | |
| | TGACTGTAGTTCTTTACCATCTCTTCGAAGAGTTCGCCAACTATG | |
| | AGCACGTTGGAATAGTCGATATTTTCCTTGGGTTTCTCTCTTTCTT | |
| | CGTCGTTGCCCTCGGAGGAGTCTTGGTAGGCGTCGTCTACGGCGT | |
| | CATAGCAGCCTTTACTTCTAGGTTTACGTCTCACATACGCGTGAT | |
| | TGAGCCGTTGTTTGTTTTTCTGTATTCCTATATGGCCTATTTGAGT | |
| | GCCGAGCTTTTTCATCTTAGCGGTATAATGGCCCTTATCGCGTCT | |
| | GGGGTTGTCATGCGCCCATATGTCGAGGCGAATATAAGTCACAA | |
| | ATCCCATACCACGATTAAATATTTCCTCAAAATGTGGTCAAGCGT | |
| | TTCAGAAACCCTTATATTCATATTCCTGGGAGTCAGCACAGTAGC | |
| | GGGCTCCCATCACTGGAACTGGACATTCGTAATATCTACGTTGCT | |
| | CTTTTGCCTGATAGCCAGAGTTCTGGGCGTGCTCGGACTGACTTG | |
| | GTTTATTAACAAATTCAGAATTGTTAAACTGACGCCTAAAGACC | |
| | AGTTCATCATAGCATATGGAGGTTTGCGCGGGGCAATCGCATTC | |
| | AGTCTGGGGTATCTCCTCGACAAGAAGCACTTCCCCATGTGCGA | |
| | TCTGTTTTTGACCGCGATCATCACAGTCATATTTTTTACGGTTTTT | |
| | GTACAGGGGATGACCATCAGGCCACTCGTTGATCTTTTGGCGGT | |
| | CAAAAAAAAACAAGAGACGAAACGAAGTATAAATGAAGAGATA | |
| | CATACTCAGTTCTTGGACCACTTGCTGACCGGGATAGAGGACAT | |
| | TTGTGGCCGCTATGGCAGGCGACGATGGAAGGATAAACTGAATC | |
| | GGTTTAACAAAAAATATGTGAAAAAATGCTTGATCGCCGGGGAA | |
| | CGGTCTAAAGAACCACAGCTTATAGCCTTCTATCATAAAATGGA | |
| | GATGAAGCAGGCGATAGAGCTGGTGGAATCCGGAGGAATGGGA | |
| | AAGATACCCAGCGCTGTCTCAACCGTGTCTATGCAAAATATCCA | |
| | TCCGAAGTCCCTTCCATCTGAGCGAATCCTGCCCGCCCTCAGCAA | |
| | GGACAAAGAGGAGGAGATTCGGAAAATTCTGAGGAATAACTTG | |
| | CAGAAGACTAGACAGCGCCTCAGATCCTATAACCGACACACCCT | |
| | GGTGGCCGACCCCTATGAGGAAGCCTGGAACCAGATGTTGCTTC | |
| | GACGGCAAAAAGCTCGACAATTGGAGCAAAAGATCAATAACTA | |
| | TCTCACCGTCCCTGCTCACAAACTTGACTCTCCCACTATGTCTCG | |
| | AGCCAGGATAGGATCTGACCCCCTGGCGTACGAGCCAAAAGAG | |
| | GATTTGCCTGTCATTACGATAGATCCGGCCTCCCCGCAGTCTCCC | |
| | GAGTCCGTAGACCTGGTTAACGAGGAACTTAAGGGCAAAGTTCT | |
| | GGGCCTTAGTCGGGATCCGGCAAAGGTTGCTGAGGAGGACGAA | |

TABLE 1-continued

REPRESENTATIVE SEQUENCES

| SEQ ID NO | SEQUENCES | OTHER INFORMATION |
|---|---|---|
| | GATGATGATGGGGGTATTATGATGAGGTCAAAAGAAACAAGTTC<br>CCCCGGTACGGACGATGTATTCACGCCGGCGCCTTCTGACTCCCC<br>AAGCTCTCAACGCATACAGCGGTGCCTGAGTGACCCGGGGCCCC<br>ATCCGGAGCCGGGTGAAGGGGAGCCGTTTTTTCCTAAAGGCCAA<br>TAG | |

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (i.e., additions), or both. Guidance in determining which and how many amino acid residues may be substituted, inserted or deleted without abolishing biological activity may be found using computer programs well known in the art, for example, DNASTAR software. Variants can be tested in functional assays. Preferred variants have less than 10%, and preferably less than 5%, and still more preferably less than 2% changes (whether substitutions, deletions, and so on).

The term "homolog" or "homologous," when used in reference to a polypeptide, refers to a high degree of sequence identity between two polypeptides, or to a high degree of similarity between the three-dimensional structure or to a high degree of similarity between the active site and the mechanism of action. In a preferred embodiment, a homolog has a greater than 60% sequence identity, and more preferably greater than 75% sequence identity, and still more preferably greater than 90% sequence identity, with a reference sequence. The term "substantial identity," as applied to polypeptides, means that two peptide sequences, when optimally aligned, such as by the programs GAP or BESTFIT using default gap weights, share at least 75% sequence identity.

As used herein, to express a gene means that the cell produces either the full-length polypeptide encoded by the gene or a functional fragment of the full-length polypeptide. The term "functional," when used in conjunction with "fragment," refers to a polypeptide which possesses a biological activity that is substantially similar to a biological activity of the entity or molecule of which it is a fragment thereof. By "substantially similar" in this context is meant that at least 25%, at least 35%, at least 50% of the relevant or desired biological activity of a corresponding wild-type peptide is retained. For example, a functional fragment of polypeptide retains enzymatic activity that is substantially similar to the enzymatic activity of the full-length polypeptide encoded by a gene expressed in the cell.

"Overexpression" refers to the production of a gene product in cells/organisms that exceeds levels of production in normal or non-transformed cells/organisms. For example, it may refer to an elevated level (e.g., aberrant level) of mRNAs encoding for a protein(s) (e.g., a RHEB, LAMP1-RHEB, CA9, or NHE1 protein or homolog thereof), and/or to elevated levels of protein(s) (e.g., RHEB, LAMP1-RHEB, CA9, and/or NHE1) in cells as compared to similar corresponding unmodified cells/organisms expressing basal levels of mRNAs (e.g., those encoding RHEB, CA9, or NHE1 protein) or having basal levels of proteins. In particular embodiments, RHEB, CA9, and/or NHE1, or homologs thereof, may be overexpressed by at least 1.5-fold, 2-fold, 3-fold, 4-fold, 5-fold, 6-fold, 8-fold, 10-fold, 12-fold, 15-fold or more in cells/organisms engineered to exhibit increased mRNA, protein, and/or activity of RHEB, LAMP1-RHEB, CA9, and/or NHE1.

The terms "cytotoxic" and "cytolytic" are used to describe the activity of effector cells such as NK cells. In general, cytotoxic activity relates to killing of target cells by any of a variety of biological, biochemical, or biophysical mechanisms. Cytolysis refers more specifically to activity in which the effector lyses the plasma membrane of the target cell, thereby destroying its physical integrity, thereby resulting in the killing of the target cell. Without wishing to be bound by theory, it is believed that the cytotoxic effect of NK cells is due to cytolysis.

The expression of RHEB, LAMP1-RHEB, CA9, and/or NHE1 can be induced by introducing one or more expression vectors carrying nucleic acids encoding one or more of RHEB, LAMP1-RHEB, CA9, and NHE1 polypeptides or fragments thereof. The polypeptide or fragment thereof can be inserted into the proper site of the vector (e.g., operably linked to a promoter). The expression vector is introduced into a selected host cell (e.g., immune cell) for amplification and/or polypeptide expression, by well-known methods such as transfection, transduction, infection, electroporation, microinjection, lipofection or the DEAE-dextran method or other known techniques. These methods and other suitable methods are well known to the skilled artisan.

A wide variety of vectors can be used for the expression of the RHEB, LAMP1-RHEB, CA9, or NHE1 protein. The ability of certain viruses to infect cells or enter cells via receptor-mediated endocytosis, and to integrate into host cell genome and express viral genes stably and efficiently have made them attractive candidates for the transfer of foreign nucleic acids into cells (e.g., immune cells). Accordingly, in certain embodiments, a viral vector is used to introduce a nucleotide sequence encoding an RHEB, LAMP1-RHEB, CA9, or NHE1 protein or fragment thereof into a host cell for expression. The viral vector may comprise a nucleotide sequence encoding an RHEB, LAMP1-RHEB, CA9, or NHE1 protein or fragment thereof operably linked to one or more control sequences, for example, a promoter. Alternatively, the viral vector may not contain a control sequence and will instead rely on a control sequence within the host cell to drive expression of the RHEB, LAMP1-RHEB, CA9, or NHE1 protein or fragment thereof. Non-limiting examples of viral vectors that may be used to deliver a nucleic acid include adenoviral vectors, AAV vectors, and retroviral vectors.

For example, an adeno-associated virus (AAV) can be used to introduce a nucleotide sequence encoding an RHEB, LAMP1-RHEB, CA9, or NHE1 protein or fragment thereof into a host cell for expression. AAV systems have been described previously and are generally well known in the art (Kelleher and Vos, Biotechniques, 17(6):1110-7, 1994; Cotten et al., Proc Natl Acad Sci USA, 89(13):6094-6098, 1992; Curiel, Nat Immun, 13(2-3):141-64, 1994; Muzyczka, Curr Top Microbiol Immunol, 158:97-129, 1992). Details concerning the generation and use of rAAV vectors are described, for example, in U.S. Pat. Nos. 5,139,941 and 4,797,368, each incorporated herein by reference in its entirety for all purposes.

In some embodiments, a retroviral expression vector can be used to introduce a nucleotide sequence encoding an RHEB, LAMP1-RHEB, CA9, or NHE1 protein or fragment thereof into a host cell for expression. These systems have been described previously and are generally well known in the art (Nicolas and Rubinstein, In: Vectors: A survey of molecular cloning vectors and their uses, Rodriguez and Denhardt, eds., Stoneham: Butterworth, pp. 494-513, 1988; Temin, In: Gene Transfer, Kucherlapati (ed.), New York: Plenum Press, pp. 149-188, 1986). Examples of vectors for eukaryotic expression in mammalian cells include AD5, pSVL, pCMV, pRc/RSV, pcDNA3, pBPV, etc., and vectors derived from viral systems such as vaccinia virus, adeno-associated viruses, herpes viruses, retroviruses, etc., using promoters such as CMV, SV40, EF-1, UbC, RSV, ADV, BPV, and β-actin.

Combinations of retroviruses and an appropriate packaging line may also find use, where the capsid proteins will be functional for infecting the target cells. Usually, the cells and virus(es) will be incubated for at least about 24 hours in the culture medium. The cells are then allowed to grow in the culture medium for short intervals in some applications, e.g., 24-73 hours, or for at least two weeks, and may be allowed to grow for five weeks or more, before analysis. Commonly used retroviral vectors are "defective," i.e., unable to produce viral proteins required for productive infection. Replication of the vector requires growth in the packaging cell line. The host cell specificity of the retrovirus is determined by the envelope protein, env (p120). The envelope protein is provided by the packaging cell line. Envelope proteins are of at least three types, ecotropic, amphotropic and xenotropic. Retroviruses packaged with ecotropic envelope protein, e.g., MMLV, are capable of infecting most murine and rat cell types. Ecotropic packaging cell lines include BOSC23. Retroviruses bearing amphotropic envelope protein, e.g., 4070A, are capable of infecting most mammalian cell types, including human, dog, and mouse. Amphotropic packaging cell lines include PA12 and PA317. Retroviruses packaged with xenotropic envelope protein, e.g., AKR env, are capable of infecting most mammalian cell types, except murine cells. The vectors may include genes that must later be removed, e.g., using a recombinase system such as Cre/Lox, or the cells that express them destroyed, e.g., by including genes that allow selective toxicity such as herpesvirus TK, bcl-xs, etc. Suitable inducible promoters are activated in a desired target cell type, either the transfected cell or progeny thereof.

In some embodiments, genome-editing techniques, such as CRISPR/Cas9 systems, designer zinc fingers, transcription activator-like effectors (TALEs), or homing meganucleases are available to induce expression of the described RHEB, LAMP1-RHEB, CA9, or NHE1 protein in an immune cell. In general, "CRISPR/Cas9 system" refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. One or more elements of a CRISPR system may be derived from a type I, type II, or type III CRISPR system. Alternatively, one or more elements of a CRISPR system may be derived from a particular organism comprising an endogenous CRISPR system, such as *Streptococcus pyogenes*. In general, a CRISPR system is characterized by elements that promote the formation of a CRISPR complex at the site of a target sequence (also referred to as a protospacer in the context of an endogenous CRISPR system).

In some embodiments, the genetic modification is introduced by transfecting the immune cell with a vector (e.g., lentiviral vector) encoding one or more of RHEB or a functional fragment thereof, LAMP1-RHEB or a functional fragment thereof, CA9 or a functional fragment thereof, and NHE1 or a functional fragment thereof. In some embodiments, RHEB or a functional fragment thereof, LAMP1-RHEB or a functional fragment thereof, CA9 or a functional fragment thereof, and/or NHE1 or a functional fragment thereof can be introduced into the immune cell using one, two, or more vectors.

In some embodiments, the immune cells may include additional genetic modification to express a tumor-targeting moiety, such as a chimeric antigen receptor or a T-cell receptor. The tumor-targeting moiety can be introduced into the immune cells by the same or different vector from the vector(s) used to introduce RHEB or a functional fragment thereof, LAMP1-RHEB or a functional fragment thereof, CA9 or a functional fragment thereof, and/or NHE1 or a functional fragment thereof.

II. MODIFIED IMMUNE CELLS AND COMPOSITIONS

In another aspect, this disclosure additionally provides a modified immune cell comprising a genetic modification that comprises overexpression of RHEB or a functional fragment thereof, LAMP1-RHEB or a functional fragment thereof, overexpression of CA9 or a functional fragment thereof, overexpression of NHE1 or a functional fragment thereof, or combination thereof.

In some embodiments, RHEB has an amino acid sequence at least 75% (e.g., 80%, 85%, 90%, 95%, 99%) identical to SEQ ID NO: 1, LAMP1-RHEB has an amino acid sequence at least 75% identical to SEQ ID NO: 3, CA9 has an amino acid sequence at least 75% (e.g., 80%, 85%, 90%, 95%, 99%) identical to SEQ ID NO: 4, and NHE1 has an amino acid sequence at least 75% (e.g., 80%, 85%, 90%, 95%, 99%) identical to SEQ ID NO: 5.

In some embodiments, RHEB has an amino acid sequence at least 75% (e.g., 80%, 85%, 90%, 95%, 99%) identical to SEQ ID NO: 2, LAMP1-RHEB has an amino acid sequence at least 75% (e.g., 80%, 85%, 90%, 95%, 99%) identical to SEQ ID NO: 3, while the substitution(s) (e.g., a substitution at N153, for example, N153T) conferring RHEB constitutive activity are retained. In some embodiments, NHE1 has an amino acid sequence at least 75% (e.g., 80%, 85%, 90%, 95%, 99%) identical to SEQ ID NO: 6, while the substitution (s) (e.g., substitution at H540, H543, H544, and/or H545, for example, H540R, H543R, H544R, and/or H545R) conferring NHE1 constitutive activity are retained.

In some embodiments, RHEB has an amino acid sequence of SEQ ID NO: 1 or 2, LAMP1-RHEB has an amino acid sequence of SEQ ID NO: 3, CA9 has an amino acid sequence of SEQ ID NO: 4, and NHE1 has an amino acid sequence of SEQ ID NO: 5 or 6.

In some embodiments, the immune cells may include an additional genetic modification to express a tumor-targeting moiety, such as a chimeric antigen receptor or a T-cell receptor. The tumor-targeting moiety can be carried by the same or different vector from the vector(s) harboring RHEB or a functional fragment thereof, LAMP1-RHEB or a functional fragment thereof, CA9 or a functional fragment thereof, and/or NHE1 or a functional fragment thereof.

The modified immune cells (e.g., NK cells, T-cells) can be incorporated into pharmaceutical compositions suitable for administration. The pharmaceutical compositions generally comprise substantially purified modified immune cells and a pharmaceutically acceptable carrier in a form suitable for administration to a subject. Pharmaceutically-acceptable carriers are determined in part by the particular composition being administered, as well as by the particular method used to administer the composition. The pharmaceutical compositions are generally formulated as sterile, substantially isotonic and in full compliance with all Good Manufacturing Practice (GMP) regulations of the U.S. Food and Drug Administration.

The terms "pharmaceutically acceptable," "physiologically tolerable," as referred to compositions, carriers, diluents, and reagents, are used interchangeably and include materials that are capable of administration to or upon a subject without the production of undesirable physiological effects to the degree that would prohibit administration of the composition. For example, "pharmaceutically-acceptable excipient" includes an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

Examples of such carriers or diluents include, but are not limited to, water, saline, Ringer's solutions, dextrose solution, and 5% human serum albumin. The use of such media and compounds for pharmaceutically active substances is well known in the art. Except insofar as any conventional media or compound is incompatible with the modified immune cells, use thereof in the compositions is contemplated. Supplementary active compounds can also be incorporated into the compositions.

A pharmaceutical composition is formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water-soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate-buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. In many cases, it will be preferable to include isotonic compounds, e.g., sugars, polyalcohols such as mannitol, sorbitol, sodium chloride in the composition. Prolonged absorption of the injectable compositions can be brought about by including in the composition a compound which delays absorption, e.g., aluminum monostearate and gelatin.

Sterile injectable solutions can be prepared by incorporating the modified immune cells in the required amount in an appropriate solvent with one or a combination of ingredients enumerated above, as required. Generally, dispersions are prepared by incorporating the modified immune cells into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof. The modified immune cells can be administered in the form of a depot injection or implant preparation, which can be formulated in such a manner as to permit a sustained or pulsatile release of the active ingredient.

Systemic administration can also be by transmucosal or transdermal means. For transmucosal or transdermal administration, penetrants appropriate to the barrier to be permeated are used in the formulation. Such penetrants are generally known in the art, and include, e.g., for transmucosal administration, detergents, bile salts, and fusidic acid derivatives. For transdermal administration, the modified immune cells are formulated into ointments, salves, gels, or creams as generally known in the art.

In some embodiments, the modified immune cells are prepared with carriers that will protect the modified immune cells against rapid elimination from the body, such as a controlled release formulation, including implants and microencapsulated delivery systems. Biodegradable, biocompatible polymers can be used, such as ethylene-vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically-acceptable carriers.

In some embodiments, the composition includes the immune cells as described above and optionally a cryoprotectant (e.g., glycerol, DMSO, PEG).

Also within the scope of this disclosure is a kit comprising the modified immune cells or the composition described above. The kit may further include instructions for administrating the modified immune cells or the composition and optionally an adjuvant. The kit optionally includes a device suitable for administration of the composition, e.g., a syringe or other suitable delivery device. The device can be provided pre-loaded with one or both of the agents or can be empty, but suitable for loading.

III. METHODS OF TREATMENT

This disclosure further provides a method of treating cancer or tumor. The method comprises administering a therapeutically effective amount of the modified immune cells or the composition as described above to a subject in need thereof.

As used herein, the terms "subject" and "patient" are used interchangeably irrespective of whether the subject has undergone or is currently undergoing any form of treatment. As used herein, the terms "subject" and "subjects" may refer to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgus monkey, chimpanzee, etc) and a human). The subject may be a human or a non-human. In more exemplary aspects, the mammal is a human.

The immune cells for use in generating the modified immune cells may be isolated using various methods such as, for example, a cell washer, a continuous flow cell separator, density gradient separation, fluorescence-activated cell sorting (FACS), MILTENYI immunomagnetic depletion (MACS), or a combination of these methods.

In some embodiments, the immune cell is autologous and/or allogeneic to the subject. The method may further comprise, before the step of administrating the modified immune cell, obtaining from the subject a sample comprising the immune cell and transfecting the immune cell with a vector encoding one or more of RHEB or a functional fragment thereof, LAMP1-RHEB or a functional fragment thereof, CA9 or a functional fragment thereof, and NHE1 or a functional fragment thereof.

In some embodiments, the method may further comprise, before or after the step of transfecting the immune cell, culturing the immune cell in a medium. In some embodiments, the medium comprises a cytokine (e.g., interleukin-2, interleukin-7, interleukin-12) to promote the growth of the immune cell.

The term "culturing" or "expanding" refers to maintaining or cultivating cells under conditions in which they can proliferate and avoid senescence. For example, cells may be cultured in media optionally containing one or more growth factors, i.e., a growth factor cocktail. Stable cell lines may be established to allow for continued propagation of cells.

As used to describe the present invention, "cancer," "tumor," and "malignancy" all relate equivalently to hyperplasia of a tissue or organ. If the tissue is a part of the lymphatic or immune system, malignant cells may include non-solid tumors of circulating cells. Malignancies of other tissues or organs may produce solid tumors. The methods of the present invention may be used in the treatment of lymphatic cells, circulating immune cells, and solid tumors In some embodiments, the cancer or tumor is a solid tumor. In some embodiments, the cancer or tumor is a hematologic tumor. In some embodiments, the cancer is selected from the group consisting of melanoma, leukemia, lymphoma, multiple myeloma, prostate cancer, neuroblastoma, small cell lung cancer, and breast cancer.

The immune cells can be administered by infusion. In some embodiments, the method may include producing the immune cells in vitro before administrating to the subject. The modified immune cells can be autologous and/or allogeneic to the subject.

The immune cells may be administered in a pharmaceutical formulation, as described above. The dose of the modified immune cells for an optimal therapeutic benefit can be determined clinically. A certain length of time is allowed to pass for the circulating or locally delivered modified immune cells. The waiting period will be determined clinically and may vary depending on the composition of the composition.

The cells can be administered to individuals through infusion or injection (for example, intravenous, intrathecal, intramuscular, intraluminal, intratracheal, intraperitoneal, or subcutaneous), transdermally, or other methods known in the art. Administration may be once every two weeks, once a week, or more often, but the frequency may be decreased during a maintenance phase of the disease or disorder.

Both heterologous and autologous cells can be used. In the former case, HLA-matching should be conducted to avoid or minimize host reactions. In the latter case, autologous cells are enriched and purified from a subject and stored for later use. The cells may be cultured in the presence of host or graft T cells ex vivo and reintroduced into the host. This may have the advantage of the host recognizing the cells as self and better providing reduction in T cell activity.

The dose and the administration frequency will depend on the clinical signs, which confirm maintenance of the remission phase, with the reduction or absence of at least one or more preferably more than one clinical signs of the acute phase known to the person skilled in the art. More generally, dose and frequency will depend in part on the recession of pathological signs and clinical and subclinical symptoms of a disease condition or disorder contemplated for treatment with the above-described composition. Dosages and administration regimens can be adjusted depending on the age, sex, physical condition of the subject as well as the benefit of the treatment and side effects in the patient or mammalian subject to be treated and the judgment of the physician, as is appreciated by those skilled in the art. In all of the above-described methods, the cells can be administered to a subject at $1\times10^{4}$ to $1\times10^{10}$/time.

As used herein, the term "effective amount" or "therapeutically effective amount" refers to an amount which results in measurable amelioration of at least one symptom or parameter of a specific disorder. A therapeutically effective amount of the above-described cells can be determined by methods known in the art. An effective amount for treating a disorder can be determined by empirical methods known to those of ordinary skill in the art. The exact amount to be administered to a patient will vary depending on the state and severity of the disorder and the physical condition of the patient. A measurable amelioration of any symptom or parameter can be determined by a person skilled in the art or reported by the patient to the physician. It will be understood that any clinically or statistically significant attenuation or amelioration of any symptom or parameter of the above-described disorders is within the scope of the invention. Clinically significant attenuation or amelioration means perceptible to the patient and/or to the physician.

In some embodiments, the method further comprises administering to the subject one or more additional therapeutic agents, such as antitumor/anticancer agents, including chemotherapeutic agents and immunotherapeutic agents.

A "chemotherapeutic agent" is a chemical compound useful in the treatment of cancer. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, methyldopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, see, e.g., Agnew Chem. Intl. Ed. Engl. 33:183-186 (1994); dynemicin, including dynemicin A; an esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; podophyllinic acid; 2-ethylhydrazide; procarbazine; PSK®.; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; XELODA; ibandronate; CPT-11; topoisomerase inhibitor RFS 2000; difluoromethylornithine (DMFO); retinoic acid; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

An "immunotherapeutic agent" is a biological agent useful in the treatment of cancer. Examples of immunotherapeutic agents include atezolizumab, avelumab, blinatumomab, daratumumab, cemiplimab, durvalumab, elotuzumab, laherparepvec, ipilimumab, nivolumab, obinutuzumab, ofatumumab, pembrolizumab, and talimogene.

IV. POLYPEPTIDES AND COMPOSITIONS

In another aspect, this disclosure additional provides a polypeptide comprising a RHEB polypeptide linked (e.g., covalently linked) to a LAMP1 polypeptide, wherein the RHEB polypeptide is directly linked to the LAMP1 polypeptide or through a linker. In some embodiments, the polypeptide comprises an amino acid sequence at least 75% (e.g., 80%, 85%, 90%, 95%, 99%) identical to SEQ ID NO: 3 or an amino acid sequence of SEQ ID NO: 3.

The terms "polypeptide," "peptide," and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified, for example, disulfide bond formation, glycosylation, lipidation, acetylation, phosphorylation, pegylation, or any other manipulation, such as conjugation with a labeling component. As used herein, the term "amino acid" includes natural and/or unnatural or synthetic amino acids, including glycine and both the D or L optical isomers, and amino acid analogs and peptidomimetics.

Also provided is a polynucleotide comprising a polynucleotide sequence that encodes the polypeptide described above. In some embodiments, the polynucleotide comprises a polynucleotide sequence having at least 75% (e.g., 80%, 85%, 90%, 95%, 99%) sequence identity to the polynucleotide sequence of SEQ ID NO: 9 or a polynucleotide sequence of SEQ ID NO: 9.

A "nucleic acid" or "polynucleotide" refers to a DNA molecule (for example, but not limited to, a cDNA or genomic DNA) or an RNA molecule (for example, but not limited to, an mRNA), and includes DNA or RNA analogs. A DNA or RNA analog can be synthesized from nucleotide analogs. The DNA or RNA molecules may include portions that are not naturally occurring, such as modified bases, modified backbone, deoxyribonucleotides in an RNA, etc. The nucleic acid molecule can be single-stranded or double-stranded.

In some embodiments, the disclosed polypeptide can be encoded by a codon-optimized sequence. For example, the nucleotide sequence encoding the polypeptide may be codon-optimized for expression in a eukaryote or eukaryotic cell. In some embodiments, the codon-optimized polypeptide is codon-optimized for operability in a eukaryotic cell or organism, e.g., a yeast cell, or a mammalian cell or organism, including a mouse cell, a rat cell, and a human cell or non-human eukaryote organism.

Also within the scope of this disclosure is (a) a vector comprising the polynucleotide as described above; (b) a host cell comprising the vector; and (c) a composition comprising the polypeptide, the polynucleotide, the vector or the host cell, as described above.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector of the invention comprises an expression cassette that comprises polynucleotide sequences that encode mutant polypeptides or immunoconjugates of the invention or fragments thereof.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

V. DEFINITIONS

To aid in understanding the detailed description of the compositions and methods according to the disclosure, a few express definitions are provided to facilitate an unambiguous disclosure of the various aspects of the disclosure. Unless otherwise defined, all technical and scientific terms used herein have the same meaning as commonly understood by one of ordinary skill in the art to which this disclosure belongs.

As used herein, "expression" refers to the process by which a polynucleotide is transcribed from a DNA template (such as into an mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The term "amino acid sequence" refers to an amino acid sequence of a protein molecule. "Amino acid sequence" and like terms, such as "polypeptide" or "protein" are not meant to limit the amino acid sequence to the complete, native amino acid sequence associated with the recited protein molecule. Furthermore, an "amino acid sequence" can be deduced from the nucleic acid sequence encoding the protein.

The term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full-length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns, therefore, are absent in the messenger RNA (mRNA) transcript. The mRNA functions during translation to specify the sequence or order of amino acids in a nascent polypeptide.

The term "recombinant" when made in reference to a nucleic acid molecule refers to a nucleic acid molecule which is comprised of segments of nucleic acid joined together by means of molecular biological techniques. The term "recombinant," when made in reference to a protein or a polypeptide, refers to a protein molecule which is expressed using a recombinant nucleic acid molecule.

The term "operably linked" refers to a functional linkage between a nucleic acid expression control sequence (such as a promoter or array of transcription factor binding sites) and a second nucleic acid sequence, wherein the expression control sequence directs transcription of the nucleic acid corresponding to the second sequence.

As used herein, the term "in vitro" refers to events that occur in an artificial environment, e.g., in a test tube or reaction vessel, in cell culture, etc., rather than within a multi-cellular organism.

As used herein, the term "in vivo" refers to events that occur within a multi-cellular organism, such as a non-human animal.

As used herein, "treatment" or "treating," or "palliating" or "ameliorating" are used interchangeably. These terms refer to an approach for obtaining beneficial or desired results, including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

The terms "prevent," "preventing," "prevention," "prophylactic treatment" and the like refer to reducing the probability of developing a disorder or condition in a subject, who does not have, but is at risk of or susceptible to developing a disorder or condition.

The term "disease" as used herein is intended to be generally synonymous and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The terms "decrease," "reduced," "reduction," "decrease," or "inhibit" are all used herein generally to mean a decrease by a statistically significant amount. However, for avoidance of doubt, "reduced," "reduction" or "decrease" or "inhibit" means a decrease by at least 10% as compared to a reference level, for example, a decrease by at least about 20%, or at least about 30%, or at least about 40%, or at least about 50%, or at least about 60%, or at least about 70%, or at least about 80%, or at least about 90% or up to and including a 100% decrease (e.g., absent level as compared to a reference sample), or any decrease between 10-100% as compared to a reference level.

The terms "increased," "increase" or "enhance" or "activate" are all used herein to generally mean an increase by a statically significant amount; for the avoidance of any doubt, the terms "increased," "increase" or "enhance" or "activate" means an increase of at least 10% as compared to a reference level, for example, an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "effective amount," "effective dose," or "effective dosage" is defined as an amount sufficient to achieve or at least partially achieve a desired effect. A "therapeutically effective amount" or "therapeutically effective dosage" of a drug or therapeutic agent is any amount of the drug that, when used alone or in combination with another therapeutic agent, promotes disease regression evidenced by a decrease in severity of disease symptoms, an increase in frequency and duration of disease symptom-free periods, or a prevention of impairment or disability due to the disease affliction. A "prophylactically effective amount" or a "prophylactically effective dosage" of a drug is an amount of the drug that, when administered alone or in combination with another therapeutic agent to a subject at risk of developing a disease or of suffering a recurrence of disease, inhibits the development or recurrence of the disease. The ability of a therapeutic or prophylactic agent to promote disease regression or inhibit the development or recurrence of the disease can be evaluated using a variety of methods known to the skilled practitioner, such as in human subjects during clinical trials, in animal model systems predictive of efficacy in humans, or by assaying the activity of the agent in in vitro assays.

Doses are often expressed in relation to bodyweight. Thus, a dose which is expressed as [g, mg, or other unit]/kg (or g, mg etc.) usually refers to [g, mg, or other unit] "per kg (or g, mg etc.) bodyweight," even if the term "bodyweight" is not explicitly mentioned.

By way of example, an anticancer or antitumor agent is a drug that slows cancer progression or promotes cancer regression in a subject. In preferred embodiments, a therapeutically effective amount of the drug promotes cancer regression to the point of eliminating the cancer. "Promoting cancer regression" means that administering an effective amount of the drug, alone or in combination with an anti-neoplastic agent, results in a reduction in tumor growth or size, necrosis of the tumor, a decrease in severity of at least one disease symptom, an increase in frequency and duration of disease symptom-free periods, a prevention of impairment or disability due to the disease affliction, or otherwise amelioration of disease symptoms in the patient. Pharmacological effectiveness refers to the ability of the drug to promote cancer regression in the patient. Physiological safety refers to an acceptably low level of toxicity, or other adverse physiological effects at the cellular, organ and/or organism level (adverse effects) resulting from administration of the drug.

By way of example for the treatment of tumors, a therapeutically effective amount or dosage of the drug preferably inhibits cell growth or tumor growth by at least about 20%, more preferably by at least about 40%, even more preferably by at least about 60%, and still more preferably by at least about 80% relative to untreated subjects. In the most preferred embodiments, a therapeutically effective amount or dosage of the drug completely inhibits cell growth or tumor growth, i.e., preferably inhibits cell growth or tumor growth by 100%. The ability of a compound to inhibit tumor growth can be evaluated using the assays described infra. Inhibition of tumor growth may not be immediate after treatment, and may only occur after a period of time or after repeated administration. Alternatively, this property of a composition can be evaluated by examining the ability of the compound to inhibit cell growth. Such inhibition can be measured in vitro by assays known to the skilled practitioner. In other preferred embodiments described herein, tumor regression may be observed and may continue for a period of at least about 20 days, more preferably at least about 40 days, or even more preferably at least about 60 days.

As used herein, "administering" refers to the physical introduction of a composition comprising a therapeutic agent to a subject, using any of the various methods and delivery systems known to those skilled in the art. Routes of administration described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, a composition described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

The term "agent" is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues. The activity of such agents may render it suitable as a "therapeutic agent," which is a biologically, physiologically, or pharmacologically active substance (or substances) that acts locally or systemically in a subject.

The terms "therapeutic agent," "therapeutic capable agent," or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As used herein, the term "pharmaceutical grade" means that certain specified biologically active and/or inactive components in the drug must be within certain specified absolute and/or relative concentration, purity and/or toxicity limits and/or that the components must exhibit certain activity levels, as measured by a given bioactivity assay. Further, a "pharmaceutical grade compound" includes any active or inactive drug, biologic or reagent, for which a chemical purity standard has been established by a recognized national or regional pharmacopeia (e.g., the U.S. Pharmacopeia (USP), British Pharmacopeia (BP), National Formulary (NF), European Pharmacopoeia (EP), Japanese Pharmacopeia (JP), etc.). Pharmaceutical grade further incorporates suitability for administration by means including topical, ocular, parenteral, nasal, pulmonary tract, mucosal, vaginal, rectal, intravenous, and the like.

"Combination" therapy, as used herein, unless otherwise clear from the context, is meant to encompass administration of two or more therapeutic agents in a coordinated fashion, and includes, but is not limited to, concurrent dosing. Specifically, combination therapy encompasses both co-administration (e.g., administration of a co-formulation or simultaneous administration of separate therapeutic compositions) and serial or sequential administration, provided that administration of one therapeutic agent is conditioned in some way on administration of another therapeutic agent. For example, one therapeutic agent may be administered only after a different therapeutic agent has been administered and allowed to act for a prescribed period of time. See, e.g., Kohrt et al. (2011) *Blood* 117:2423.

"Sample," "test sample," and "patient sample" may be used interchangeably herein. The sample can be a sample of, serum, urine plasma, amniotic fluid, cerebrospinal fluid, cells (e.g., antibody-producing cells) or tissue. Such a sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art. The terms "sample" and "biological sample" as used herein generally refer to a biological material being tested for and/or suspected of containing an analyte of interest such as antibodies. The sample may be any tissue sample from the subject. The sample may comprise protein from the subject.

Any cell type, tissue, or bodily fluid may be utilized to obtain a sample. Such cell types, tissues, and fluid may include sections of tissues such as biopsy and autopsy samples, frozen sections taken for histologic purposes, blood (such as whole blood), plasma, serum, sputum, stool, tears, mucus, saliva, hair, skin, red blood cells, platelets, interstitial fluid, ocular lens fluid, cerebral spinal fluid, sweat, nasal fluid, synovial fluid, menses, amniotic fluid, semen, etc. Cell types and tissues may also include lymph fluid, ascetic fluid, gynecological fluid, urine, peritoneal fluid, cerebrospinal fluid, a fluid collected by vaginal rinsing, or a fluid collected by vaginal flushing. A tissue or cell type may be provided by removing a sample of cells from an animal, but can also be accomplished by using previously isolated cells (e.g., isolated by another person, at another time, and/or for another purpose). Archival tissues, such as those having treatment or outcome history, may also be used. Protein purification may not be necessary.

Methods well known in the art for collecting, handling, and processing urine, blood, serum, and plasma, and other body fluids, can be used in the practice of the present disclosure, for instance. The test sample can comprise further moieties in addition to the analyte of interest, such as antibodies, antigens, haptens, hormones, drugs, enzymes, receptors, proteins, peptides, polypeptides, oligonucleotides or polynucleotides. For example, the sample can be a whole blood sample obtained from a subject. It can be necessary or desired that a test sample, particularly whole blood, be treated prior to immunoassay as described herein, e.g., with a pretreatment reagent. Even in cases where pretreatment is not necessary, pretreatment optionally can be done for mere convenience (e.g., as part of a regimen on a commercial platform). The sample may be used directly as obtained from the subject or following a pretreatment to modify a characteristic of the sample. Pretreatment may include extraction, concentration, inactivation of interfering components, and/or the addition of reagents.

It is noted here that, as used in this specification and the appended claims, the singular forms "a," "an," and "the" include plural reference unless the context clearly dictates otherwise.

The terms "including," "comprising," "containing," or "having" and variations thereof are meant to encompass the items listed thereafter and equivalents thereof as well as additional subject matter unless otherwise noted.

The phrases "in one embodiment," "in various embodiments," "in some embodiments," and the like are used repeatedly. Such phrases do not necessarily refer to the same embodiment, but they may unless the context dictates otherwise.

The terms "and/or" or "/" means any one of the items, any combination of the items, or all of the items with which this term is associated.

The word "substantially" does not exclude "completely," e.g., a composition which is "substantially free" from Y may be completely free from Y. Where necessary, the word "substantially" may be omitted from the definition of the invention.

As used herein, the term "approximately" or "about," as applied to one or more values of interest, refers to a value that is similar to a stated reference value. In some embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Unless indicated otherwise herein, the term "about" is intended to include values, e.g., weight percents, proximate to the recited range that are equivalent in terms of the functionality of the individual ingredient, the composition, or the embodiment.

As used herein, the term "each," when used in reference to a collection of items, is intended to identify an individual item in the collection but does not necessarily refer to every item in the collection. Exceptions can occur if explicit disclosure or context clearly dictates otherwise.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All methods described herein are performed in any suitable order unless otherwise indicated herein or otherwise clearly contradicted by context. In regard to any of the methods provided, the steps of the method may occur simultaneously or sequentially. When the steps of the method occur sequentially, the steps may occur in any order, unless noted otherwise.

In cases in which a method comprises a combination of steps, each and every combination or sub-combination of the steps is encompassed within the scope of the disclosure, unless otherwise noted herein.

Each publication, patent application, patent, and other reference cited herein is incorporated by reference in its entirety to the extent that it is not inconsistent with the present disclosure. Publications disclosed herein are provided solely for their disclosure prior to the filing date of the present invention. Nothing herein is to be construed as an admission that the present invention is not entitled to antedate such publication by virtue of prior invention. Further, the dates of publication provided may be different from the actual publication dates, which may need to be independently confirmed.

It is understood that the examples and embodiments described herein are for illustrative purposes only and that various modifications or changes in light thereof will be suggested to persons skilled in the art and are to be included within the spirit and purview of this application and scope of the appended claims.

VI. EXAMPLES

Example 1

This example describes the materials and methods to be used in the subsequent examples.

Lentivirus Constructs

The RHEB-CA lentivirus was constructed using $RHEB_{N153T}$ cDNA from the plasmid pcDNA3-FLAG-Rheb-N153T (ADDGENE 19997), a gift from Dr. Fuyuhiko Tamanoi (Urano, J., et al. Mol Microbiol, 2005. 58(4): p. 1074-86). The CA9 lentivirus was constructed using a verified cDNA clone of human CA9 purchased from GENSCRIPT (GENSCRIPT OHu27943). The NHE1-CA virus was constructed using a codon-optimized cDNA of human NHE1 (gene symbol SLC9A1) with H-to-R mutations at the pH-sensitive histidine cluster synthesized by GENECOPOEIA (GENECOPOEIA CS-T8340-04) (Webb, B. A., et al., J Biol Chem, 2016. 291(46): p. 24096-24104). SERPINB9 lentivirus was constructed using a verified human SERPINB9 cDNA clone purchased from GENSCRIPT (GENSCRIPT OHu01596). LAMP1-RHEB lentivirus was constructed by overlapping extension PCR with using the RHEBN153T from pcDNA3-FLAG-Rheb-N153T (ADDGENE 19997) and the FLAG-LAMP from LAMP1-mRFP-FLAG (ADDGENE 34611). A linker sequence (GGAGGCGGCACCATG (SEQ ID NO: 26)) was added in between using synthesized DNA oligos. All custom lentiviral plasmids have been verified by sequencing at the University of Pennsylvania Cell Center.

Cell Lines

NK-92 cells and EM-MESO cells were gifts from Dr. Steven Albelda at the University of Pennsylvania, and human melanoma cell lines (WM1727A, WM3211, WM3629, and WM3681) were obtained as gifts from Dr. Meenhard Herlyn at the Wistar Institute (Krepler, C., et al., Cell Rep, 2017. 21(7): p. 1953-1967). The identity of the cells in use was verified by short tandem repeat (STR) profiling and submitted samples to the University of Pennsylvania Cell Center for mycoplasma testing monthly.

Characterization

For western blot analysis of overexpressed proteins, antibodies against RHEB (CELL SIGNALING TECHNOLOGY 13879), CA9 (NOVUS BIOLOGICALS NB100-417), and NHE1 (SANTA CRUZ sc-136239) were used. For flow cytometry, PE-conjugated antibody against granzyme B (INVITROGEN MHGB04) and APC-conjugated antibody against IFN-γ (INVITROGEN 17-7311) were used. The specificity of the antibodies was verified by western blot analysis using lysates of cells transfected with siRNA against the target. For cell labeling in flow cytometry, CELLTRACE CFSE (INVITROGEN C34554) and CELLTRACE Yellow (INVITROGEN C34567) at 5 μM, and ethidium homodimer-1 (INVITROGEN E1169) at 4 μM were used.

For $pH_i$ measurement, the cells were stained with 5-(and-6)-carboxy SNARF-1, acetoxymethyl ester, acetate (INVITROGEN C1272) at 5 μM. To equilibrate $pH_i$ with $pH_e$ during $pH_i$ measurement, the cells were incubated in a high $K^+$ buffer containing 10 μM of nigericin (SIGMA N7143) and 10 μM of valinomycin (SIGMA V0627) as previously described (Owen, C. S., Anal Biochem, 1992. 204(1): p. 65-71).

Example 2: NK-92-Mediated Killing

Figure 1B:
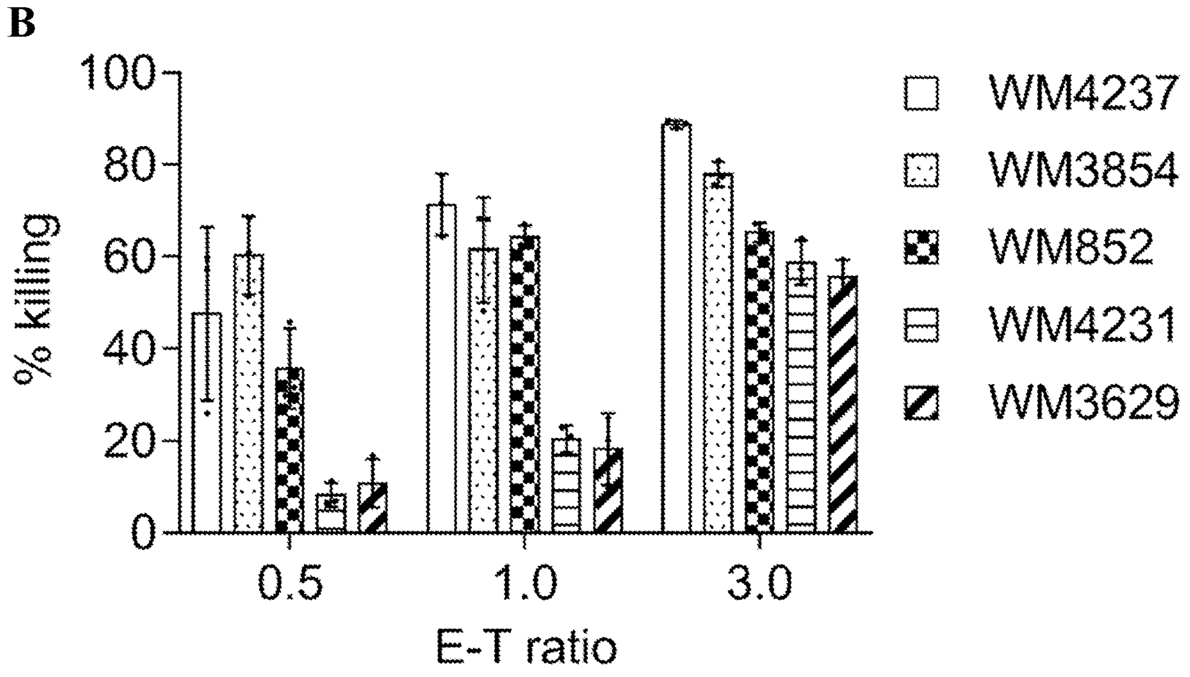

Human Melanoma Cell Lines Showed Different Sensitivity to NK-92-Mediated Killing To model NK cell-mediated killing, the human NK cell line NK-92 was used. NK-92 is an NK cell line established from peripheral blood mononuclear cells of a patient diagnosed with progressive non-Hodgkin's lymphoma. NK-92 cells resemble activated NK cells and are cytotoxic to multiple hematologic and solid tumor cell lines in vitro (Klingemann, H., L. et al. Front Immunol, 2016. 7: p. 91). Although there are differences between NK-92 cells and primary NK cells, simple culture condition, and ability to perform lentiviral transduction makes NK-92 a suitable model for studying basic cellular and molecular biology pathways in NK cells. To assess the cytotoxicity of NK-92 cells, human melanoma cell lines were used as targets because of the described metabolic relevance of the melanoma microenvironment. Human melanoma cell lines WM1727A, WM3211, WM3629, WM3681, WM4237, WM3854, WM852, WM4231, and WM3629 were labeled with CELLTRACE Yellow (INVITROGEN) and seeded onto 24-well plates at $6\times10^4$ cells/well. Cells were allowed to attach for 8 hours in before NK-92 cells were added at effector-target (E:T) ratios of 0.5:1 and 1:1 (for WM1727A, WM3211, WM3629, and WM3681, as in FIG. 1A) and of 0.5:1, 1:1, and 1:3 (for WM4237, WM3854, WM852, WM4231, and WM3629, as in FIG. 1B). All cells were collected by trypsinization after 24 hours of incubation, and dead cells were stained with ethidium homodimer-1 (EthD-1). Cell samples were then analyzed with Guava easyCyte flow cytometer (MILLIPORE SIGMA). Remaining live melanoma cells (defined as $\text{Yellow}^+$ $\text{EthD-1}^-$) in each well were quantified, and percentage killing was calculated by comparing the number of live melanoma cells in NK-92-containing groups with that in control groups without NK-92. As shown in FIGS. 1A and 1B, NK-92 cells exerted natural cytotoxicity on the nine example human melanoma cell lines (WM1727A, WM3211, WM3629, WM3681, WM4237, WM3854, WM852, WM4231, and WM3629) at indicated effector-target (E-T) ratio in a 24-hour in vitro killing assay (N=3). These melanoma cells showed different sensitivity to NK-92-mediated killing.

NK-92-Mediated Killing of WM3629 Melanoma Cells was Extracellular pH ($pH_e$)-Sensitive.

Figure 1C:
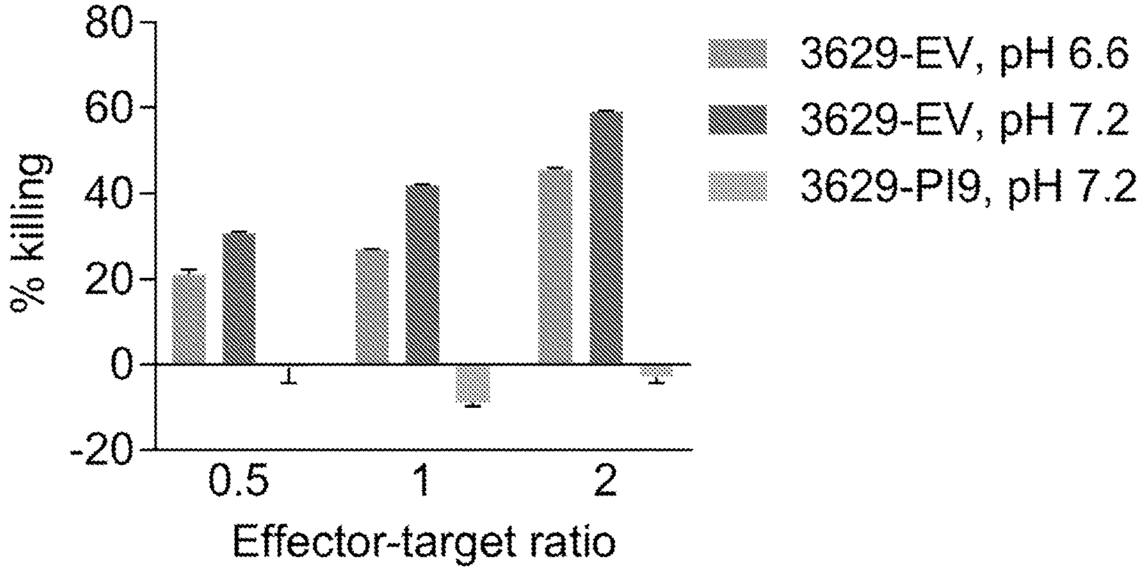

Empty vector (EV) or SERPINB9 (PI9) lentivirus-transduced WM3629 melanoma cells (both express EGFP) were seeded at $6\times10^4$ cells/well in 24-well plates and co-cultured with NK-92 cells at effector-target ratios of 0.5:1, 1:1, and 2:1 for 24 hours. To control $pH_e$, cells were incubated under atmospheric gas conditions in modified NK-92 media without sodium bicarbonate but containing 20 mM of chemical buffers HEPES and PIPES. To study the effect of acidic $pH_e$ on NK-92 cells, a $pH_e$ range of 6.3-7.4 was used, which overlaps with the observed $pH_e$ range in metastatic melanomas. The pH of the media was adjusted to desired values using hydrochloric acid (HCl) or sodium hydroxide (NaOH). Remaining live melanoma cells (defined as $\text{EGFP}^+$ $\text{EthD-1}^-$) were quantified by flow cytometry as described. As shown in FIG. 1C, low $pH_e$ blunted in vitro cytotoxicity of NK-92 cells against WM3629 melanoma cells. NK-92-mediated killing of WM3629 cells is granzyme B-dependent, as SERPINB9, an inhibitor of granzyme B, blocked NK-92-mediated killing.

Example 3: Effects of RHEB Expression on mTORC1 Activity

Figure 2A:
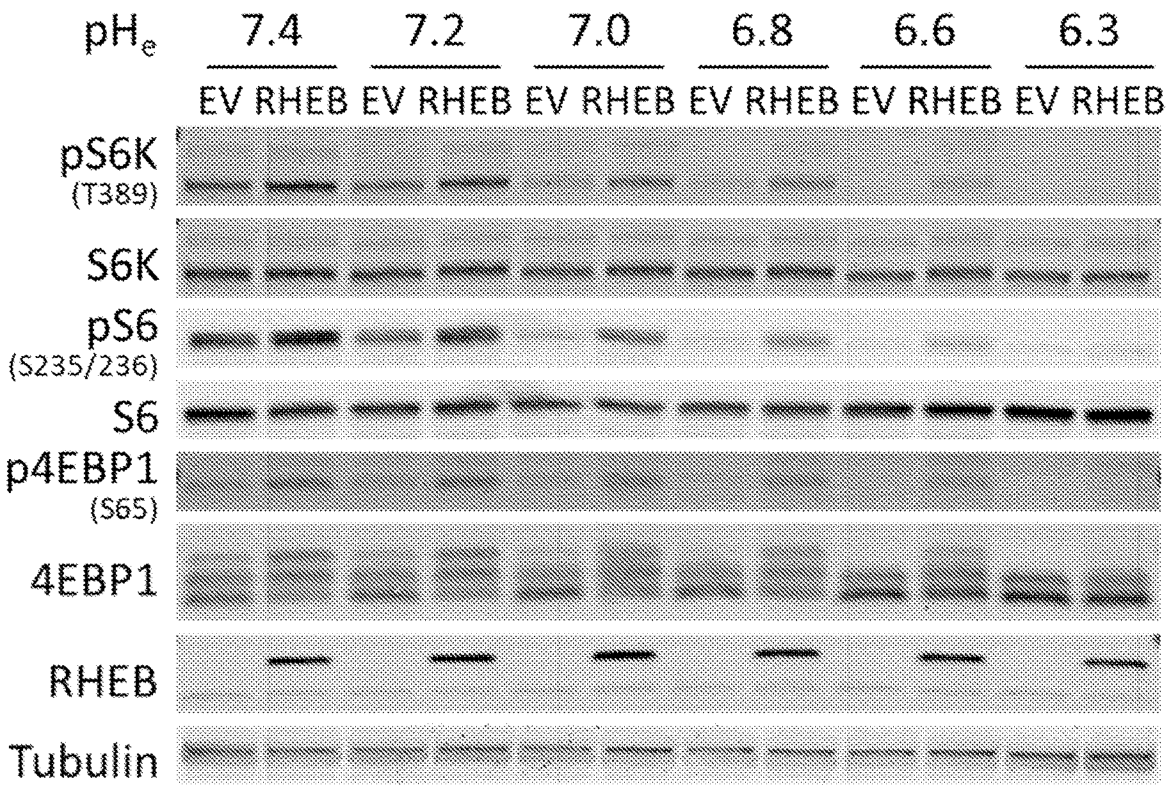
FIGS. 2A, 2B, and 2C (collectively "FIG. 2") show the effects of expression of constitutively active RHEB on mTORC1 activity in NK-92 cells.

Constitutively active RHEB enhanced mTORC1 activity in NK-92 cells at near-neutral extracellular pH ($pH_e$).

mTORC1 is important for maturation, metabolism, and effector function of NK cells, but whether mTORC1 is involved in acid-mediated suppression of the antitumor activity of NK cells is not fully understood. To test if inhibited mTORC1 underlies the suppressed antitumor activity of NK cells in acidic culture conditions, a constitutively active mutant of the mTORC1 activator RHEB (RHEB-CA) was overexpressed in NK-92 cells. RHEB is a specific activator of mTORC1 but not mTORC2. To study the effect of acidic $pH_e$ on NK-92 cells, a $pH_e$ range of 6.3-7.4 was used, which overlaps with the observed $pH_e$ range in metastatic melanomas. As shown in FIG. 2A, empty vector (EV) or constitutively active RHEB ($\text{RHEB}^{N153T}$)-transduced NK-92 cells were incubated under $pH_e$-controlled conditions for 6 hours. Total proteins were extracted from the cells, and phosphorylated mTOR and mTORC1 targets S6K, S6, and 4EBP1 were detected by western blot, with total levels of these proteins as controls. The results show that $\text{RHEB}^{N153T}$ enhanced mTORC1 activity in NK-92 cells at $pH_e$ 7.4 and partially rescues it at $pH_e$ 7.0.

Modified NK-92 Cells

Lentiviral constructs expressing RHEB-CA (human $\text{RHEB}^{N153T}$) with constitutive GTPase activity were generated (Urano, J., et al. Mol Microbiol, 2005. 58(4): p. 1074-86). Expression of the mutant RHEB is driven by human EF1α promoter, and bicistronic expression of EGFP was achieved by joining cDNAs of RHEB-CA and EGFP with an internal ribosome entry site (IRES). NK-92 cells were transduced with RHEB-CA lentivirus (NK-92-RHEB) and confirmed expression of RHEB-CA by western blot. As a control, NK-92 cells were also transduced with the empty lentiviral vector containing IRES-EGFP (NK-92-EV).

Proliferation and Viability

To assess the impact of mTORC1 activation by RHEB-CA on proliferation and viability of NK-92 cells in acidic media, NK-92-EV and NK-92-RHEB cells were cultured in media with pH of 6.6, 6.8, 7.0, and 7.2 for three days and determine cell number daily by flow cytometry using a modified flow rate-based method (Storie, I., et al., Cytometry B Clin Cytom, 2003. 55(1): p. 1-7). Both NK-92-EV and NK-92-RHEB cells express EGFP driven by the lentiviral vector. Dead cells were stained with the membrane-impermeable DNA binding dye ethidium homodimer-1 (EthD-1) prior to each flow analysis. After staining, each sample of cells was resuspended in a defined volume of buffer and analyze a fraction of each sample using the Guava easyCyte flow cytometer, which measures flow rate while analyzing the samples. Proliferation of cells by calculating total live cell number was assessed by:

$$\text{Total live cells} = \text{Total volume of cells } (\mu l) \times \text{Flow rate (events}/\mu l) \times \frac{EGFP^{+} EthD\text{-}1^{-} \text{ events (live cells)}}{\text{Total recorded events (set value)}}$$

In addition, viability of the cells was determined by calculating the percentage of viable cells based on EthD-1 staining. To maintain $pH_e$ in these and all subsequent experiments, NK-92-EV and NK-92-RHEB cells were incubated in modified NK-92 media buffered with 20 mM HEPES and PIPES in atmospheric $CO_2$. To avoid pH changes during storage of the media, the pH of the media was recalibrated prior to each experiment.

IFN-γ and Granzyme B Expression

To assess intracellular IFN-γ and granzyme B levels in NK-92 cells in acidic conditions, intracellular staining was performed, and the cells were analyzed by flow cytometry. NK-92-EV and NK-92-RHEB cells were harvested and treated in media with varied $pH_e$ for 12 or 24 hours. After fixation and permeabilization of harvested cells, non-specific binding was blocked using human Fc blocking reagents. Next, the cells were stained using fluorophore-conjugated antibodies against human IFN-γ and granzyme B. To control for non-specific binding, additional samples were stained with fluorophore-conjugated isotype control antibodies.

Constitutively Active RHEB Enhanced Cytotoxicity of NK-92 Cells to WM3629 Melanoma Cells at Low Extracellular pH ($pH_e$).

Figure 2B:
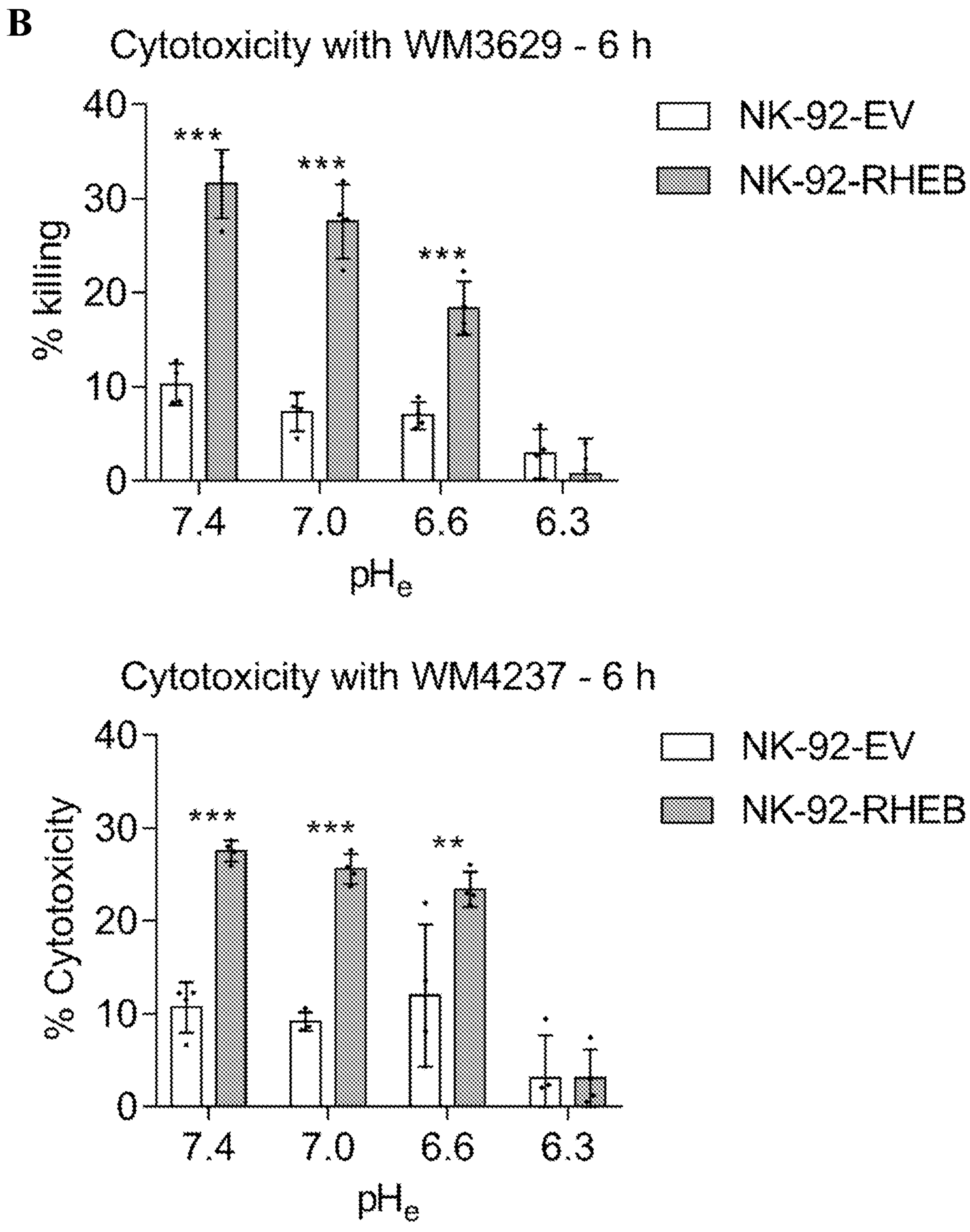

FIG. 2B is a set of graphs showing cytotoxicity of empty vector (EV)- or constitutively active RHEB-transduced NK-92 cells to human melanoma cell lines WM3629 (top) and WM4237 (bottom) at indicated extracellular pH ($pH_e$) in a 6-hour in vitro killing assay. N=4, *p<0.001, p<0.01. CELLTRACE Yellow-labeled WM3629 melanoma cells were co-cultured with empty vector (EV) or constitutively active RHEB (RHEBN153T)-transduced NK-92 cells at 1:1 ratio for 12 hours under $pH_e$-controlled culture media that contains $NaHCO_3$ and 20 mM of HEPES and PIPES. Live melanoma cells were quantified by flow cytometry, as described in Proliferation and viability section above. As shown in FIG. 2B, $RHEB^{N153T}$ enhanced NK-92-mediated killing of WM3629 cells at $pH_e$ of 6.6.

Constitutively Active RHEB Enhanced Tumor Cell-Induced Degranulation of NK-92 Cells.

Figure 2C:
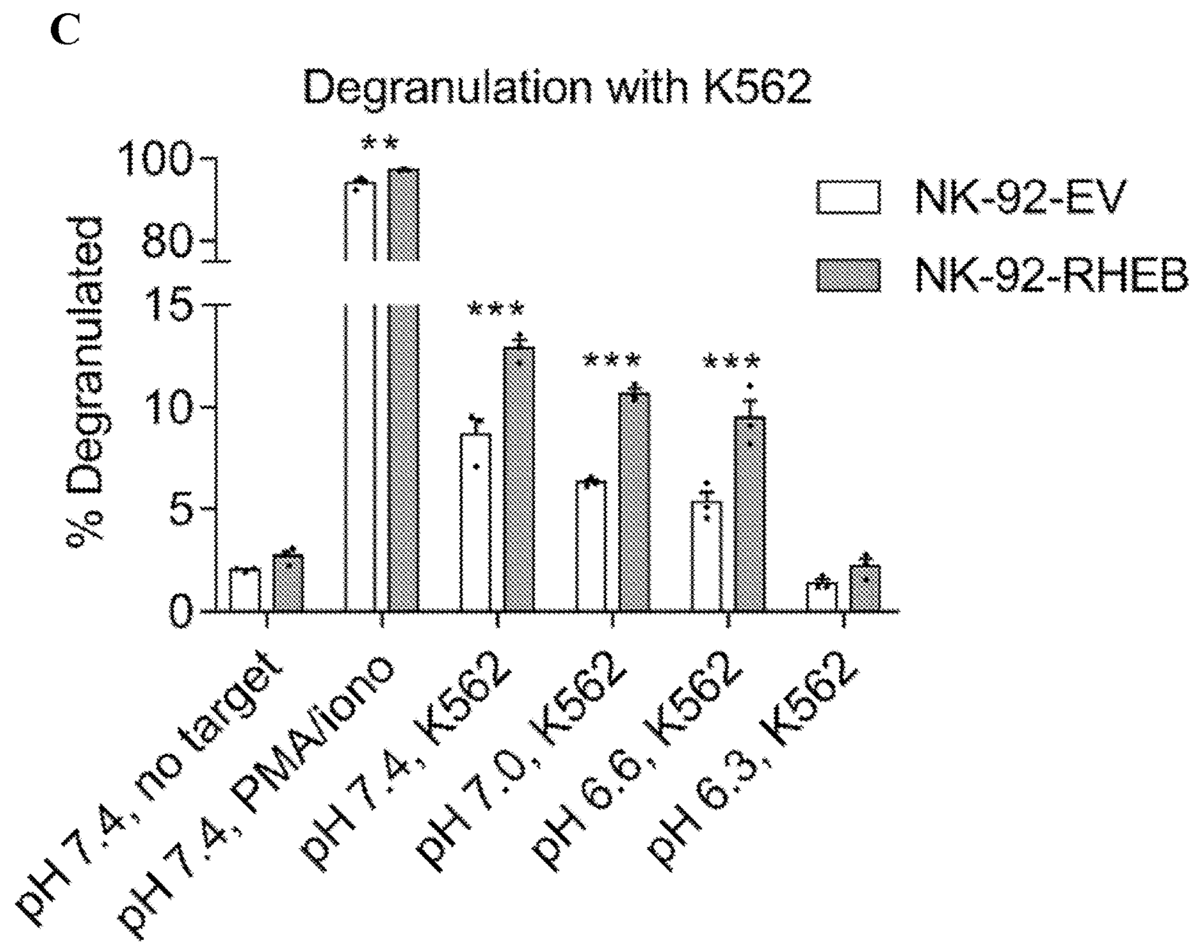

Degranulation is the release of cytotoxic granules by NK cells upon engaging target cells, which is a crucial step in NK-mediated killing. Increased degranulation corroborates with increased cytotoxicity. As shown in FIG. 2C, empty vector- or constitutively active RHEB-transduced NK-92 cells were mixed with K562 (human leukemia) cells at 1:2 ratio in HEPES/PIPES/$NaHCO_3$-buffered culture media with defined pH for 6 hours, in the presence of vesicular trafficking inhibitors monensin and brefeldin A. Externalization of CD107a, a lysosomal marker, is associated with degranulation, and was detected by flow cytometry using PE-Cy7-conjugated anti-CD107a antibody. Phorbol myristate acetate (PMA) and ionomycin were used as positive controls to induce degranulation. Percent degranulation was calculated as the percent of CD107a-positive NK-92 cells relative to PE-Cy7-conjugated isotype control antibody-stained NK-92 cells. The results show that constitutively active RHEB enhanced tumor cell-induced degranulation of NK-92 cells.

Example 4: Effects of CA9 and NHE1 Expression on NK-Mediated Killing

In addition to increased glycolysis as described previously, melanoma further acidifies its TME by upregulating pH regulatory proteins such as CA9 and NHE1. These proteins extrude intracellular acids, which decreases $pH_e$ while increasing $pH_i$, protecting melanoma cells from acidosis. However, infiltrating immune cells such as NK cells often lack these pH regulatory proteins and are susceptible to the acidic TME. Acidic $pH_e$ can inhibit mTORC1 activity by decreasing pH; and disrupting colocalization between mTORC1 and its activator RHEB (Walton, Z. E., et al., Cell, 2018. 174(1): p. 72-87 e32). While direct rescue of mTORC1 activity in NK-92 cells may help them resist acid-mediated suppression of antitumor activity, hyperactivation of mTORC1 in immune cells may also promote autoimmunity due to aberrant expansion of immune cells. Therefore, indirect rescue of NK cell function by increasing their $pH_i$ in acidic conditions may be a good alternative.

To modulate $pH_i$ of NK-92 cells, the pH regulatory protein CA9 was overexpressed. CA9 catalyzes reversible hydration of $CO_2$ generated by oxidative phosphorylation or neutralization of intracellular acids by bicarbonate, a reaction catalyzed by the intracellular carbonic anhydrase CA2 (Ditte, P., et al. Cancer Res, 2011. 71(24): p. 7558-67). The bicarbonate produced by CA9 can be recycled back to cells by transporters such as NBCe1, thereby facilitating net export of intracellular $H^+$. It was found that overexpression of CA9 in WM3629 melanoma cells resulted in increased pH; when cells were incubated in $pH_e$ of 7.0 and 7.4. Overexpression of CA9 in NK-92 cells also resulted in increased mTORC1 activity in acidic media compared to empty vector-transduced cells (FIG. 4). As an alternative approach to CA9, a constitutively active mutant of the pH regulatory protein NHE1 was overexpressed in NK-92 cells. NHE1 facilitates export of $H^+$ in exchange for import of $Na^+$. The reaction is driven by the inwardly directed $Na^+$ gradient, which is established by active export of $Na^+$ by pumps such as $Na^+/K^+$ ATPase.

Modified NK-92 Cells

Lentiviral constructs expressing human CA9 or a constitutively active mutant of NHE1 (NHE1-CA) with mutations at pH-sensitive histidine clusters were generated. The lentiviral vectors used are the same as the one in EXAMPLE 3. NK-92 cells were transduced with CA9 or NHE1-CA lentivirus (NK-92-CA9 and NK-92-NHE1, respectively), and expression of CA9 or the mutant NHE1 was confirmed by western blot. The following experiments were first performed using NK-92-CA9, and NK-92-NHE1 was used as an alternative.

$pH_i$ Measurement

To measure $pH_i$ of NK-92 cells, cells were stained using a cell-permeable (acetoxymethyl ester) variant of the pH-indicator dye 5-(and-6)-carboxy SNARF-1 as previously described (Owen, C. S., Anal Biochem, 1992. 204(1): p. 65-71). With a single-wavelength excitation of 488 nm or 514 nm, the dye has two emission peaks at around 580 nm and 640 nm. Decreasing pH causes a shift in the emission spectrum of the dye, leading to decreased emission at 640 nm but increased emission at 580 nm. Therefore, the ratio between emissions at 580 nm and 640 nm reflects pH. Such ratiometric measurement eliminates errors caused by non-uniform dye loading and photobleaching. Stained NK-92 cells were incubated in live-cell imaging buffers with controlled pH for 30 min before analyzing them by flow cytometry. The cells were excited at a single wavelength of 488 nm, and dual emission at 580 nm and 640 nm were recorded using two different filter sets. To calibrate the fluorescence response of SNARF-1, a separate group of stained NK-92 cells was incubated in pH-controlled live-cell imaging buffers containing high $K^+$ (140 mM) and 10 μM of ionophores nigericin and valinomycin. These ionophores facilitate an exchange for $K^+$ and $H^+$ to equilibrate $pH_i$ with $pH_e$. A standard curve of 580/640 nm emission ratio versus $pH_i$ was generated following the calibration and $pH_i$ of NK-92-EV, and NK-92-CA9 was estimated in various $pH_e$ by interpolating the standard curve.

Proliferation and Viability

Proliferation and viability of NK-92-CA9 with NK-92-EV were compared at various $pH_e$ using a similar flow cytometry-based method as described in EXAMPLE 3.

IFN-γ and Granzyme B Expression

Intracellular IFN-γ and granzyme B in NK-92-CA9 and NK-92-EV were assessed at various $pH_e$ using intracellular staining flow cytometry as described in EXAMPLE 3.

CA9 Partially Rescued mTORC1 Activity in NK-92 Cells at Low Extracellular pH ($pH_e$).

Figure 3A:
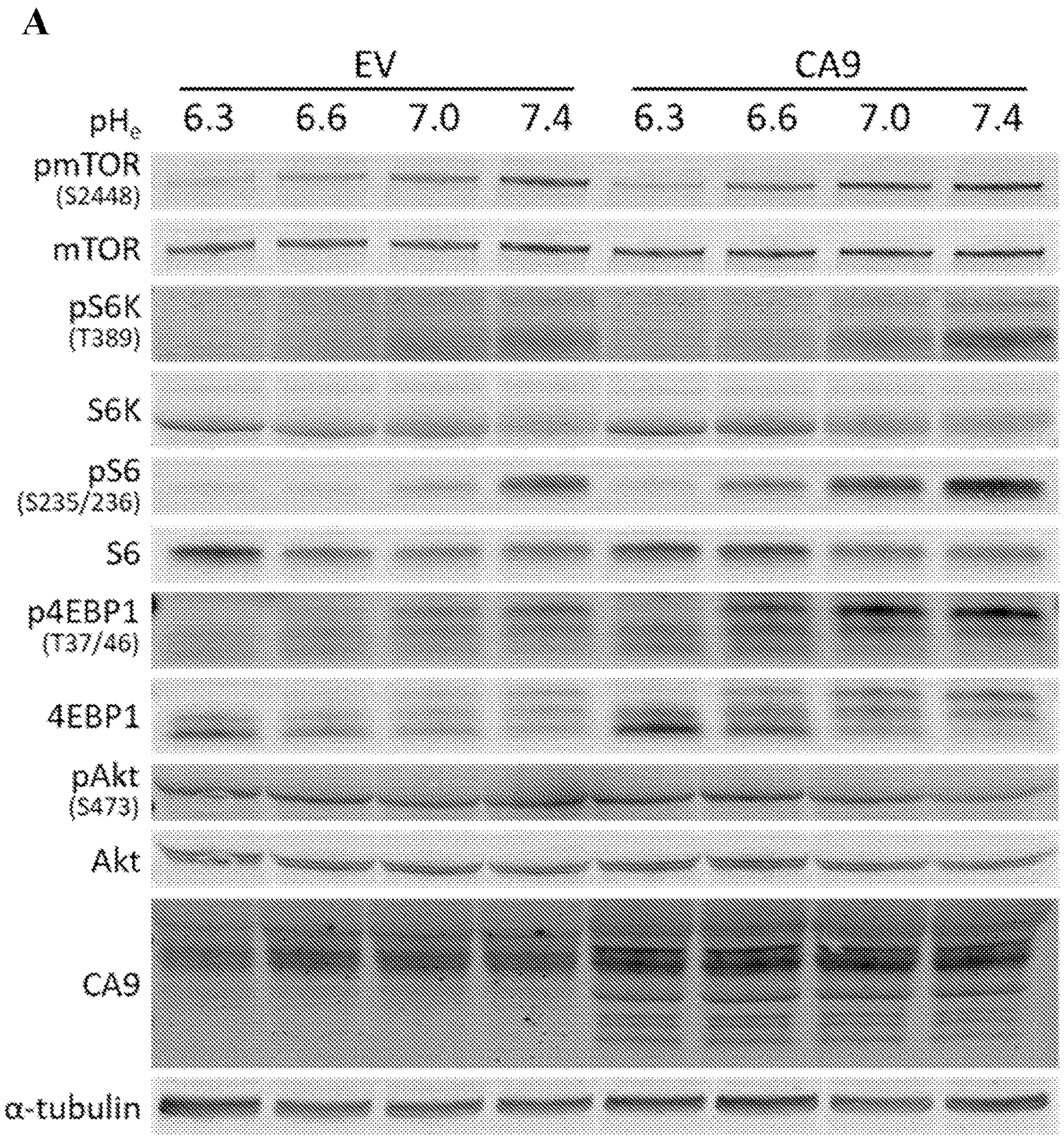
FIGS. 3A, 3B, 3C, and 3D (collectively "FIG. 3") show the effects of expression of CA9 on mTORC1 activity in NK-92 cells.
Figure 3B:
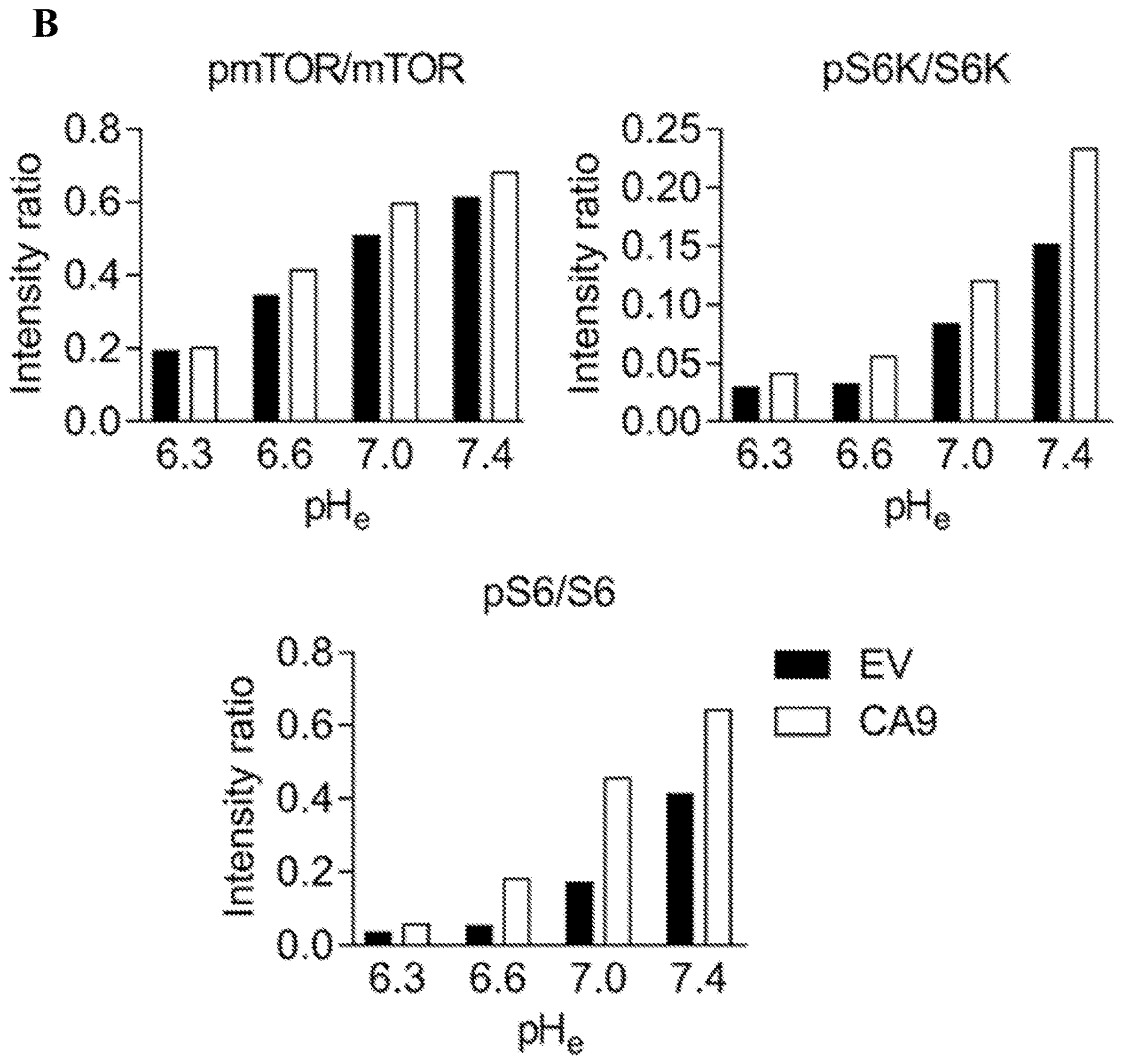

Empty vector (EV) or CA9-transduced NK-92 cells were incubated under $pH_e$-controlled conditions for 6 hours. Total proteins were extracted from the cells, and phosphorylated mTOR and mTORC1 targets S6K, S6, and 4EBP1 were detected by western blot, with total levels of these proteins as controls. FIG. 3A is an image of the blots, and FIG. 3B is a graph showing quantification based on the images (using Image Studio software, LI-COR). As shown in FIGS. 3A and 3B, CA9 expression enhanced mTORC1 activity in NK-92 cells at $pH_e$ 7.4 and partially rescued it at lower $pH_e$.

CA9 Enhanced Cytotoxicity of NK-92 Cells to EM-MESO Mesothelioma Cells at Low Extracellular pH ($pH_e$).

Figure 3C:
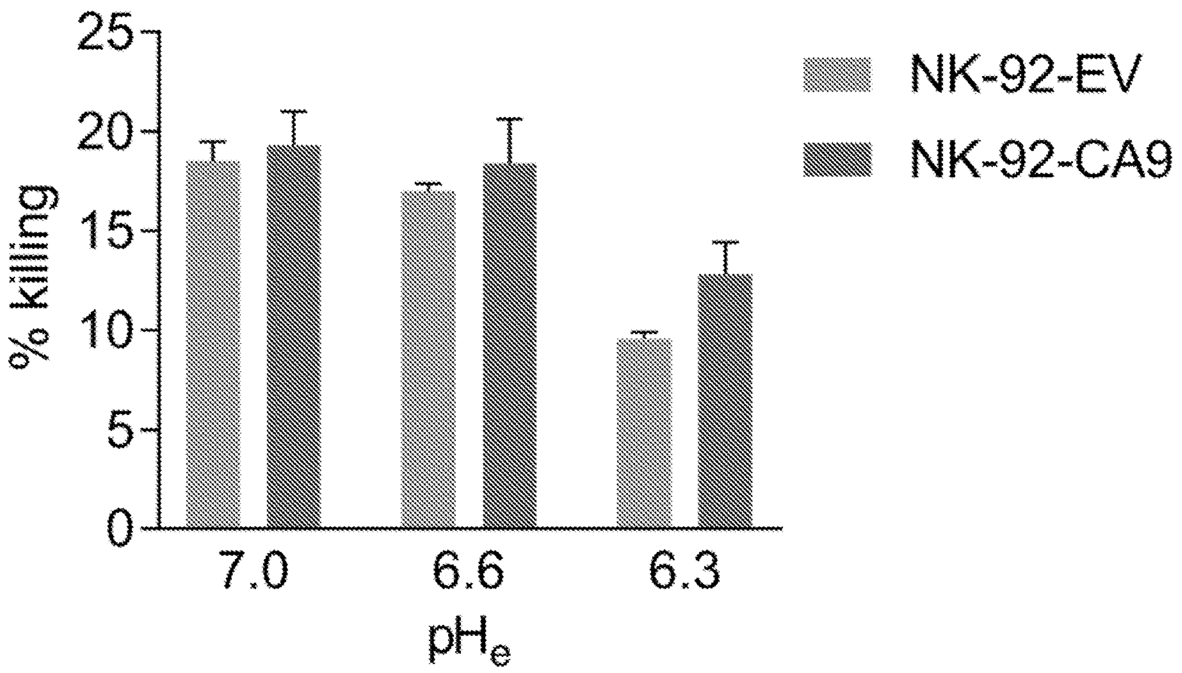

FIG. 3C shows that CA9 expression enhanced cytotoxicity of NK-92 cells to EM-MESO mesothelioma cells at low extracellular pH ($pH_e$). CELLTRACE Yellow-labeled EM-MESO mesothelioma cells were co-cultured with empty vector (EV) or CA9-transduced NK-92 cells at 1:1 ratio for 12 hours under $pH_e$-controlled conditions. CELLTRACE Yellow-labeled EM-MESO mesothelioma cells were co-cultured with empty vector (EV) or CA9-transduced NK-92 cells at 1:1 ratio for 12 hours under $pH_e$-controlled conditions. As shown in FIG. 3C, CA9 expression enhanced NK-92-mediated killing of EM-MESO cells at $pH_e$ of 6.3.

CA9 Increased Intracellular pH of NK-92 Cells.

Figure 3D:
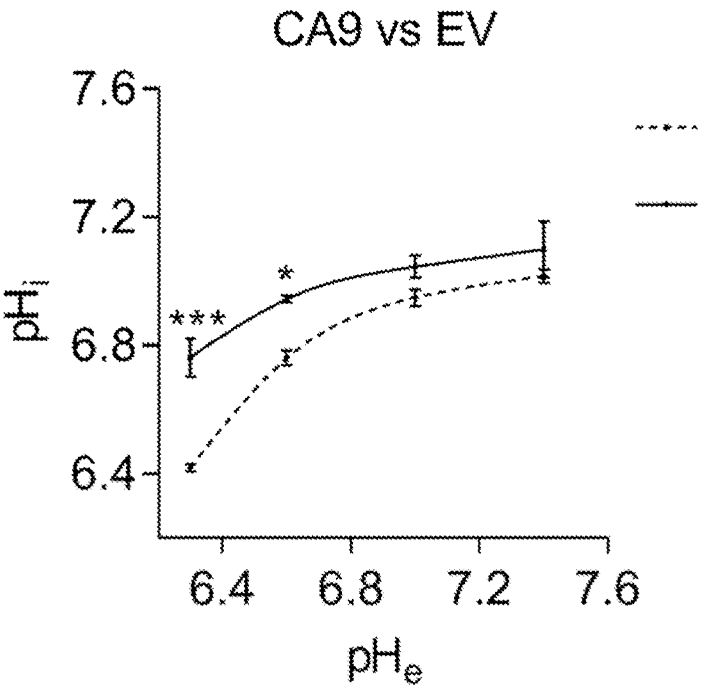

FIG. 3D shows intracellular pH ($pH_i$) of empty vector (EV)- or CA9-transduced NK-92 cells at indicated extracellular pH ($pH_e$). N=3, ***p<0.001, *p<0.05. Empty vector- or CA9-transduced NK-92 cells were loaded with 5 μM of the fluorescent pH indicator dye 5-(and-6)-Carboxy SNARF-1, and incubated in HEPES/PIPES/$NaHCO_3$-buffered culture media with defined pH for 2 hours. Cells were collected and resuspended in $Na^+$-containing live-cell imaging buffers of the same pH for 30 min before analyzed by flow cytometry. With a single excitation at 532 nm, emissions at 580 nm and 640 nm were recorded, with the ratio between the two calculated. Calibration of intracellular pH ($pH_i$) was done by incubating the cells in high-$K^+$ buffers with defined pH in the presence of 10 mM of valinomycin and nigericin, which equilibrate $pH_i$ with buffer pH. The resulting calibration curve was used to convert 580/640 nm emission ratio into $pH_i$. As shown, CA9 was able to increase intracellular pH of NK-92 cells.

Constitutively Active NHE1 Enhanced ERK Activity in NK-92 Cells

Figure 4A:
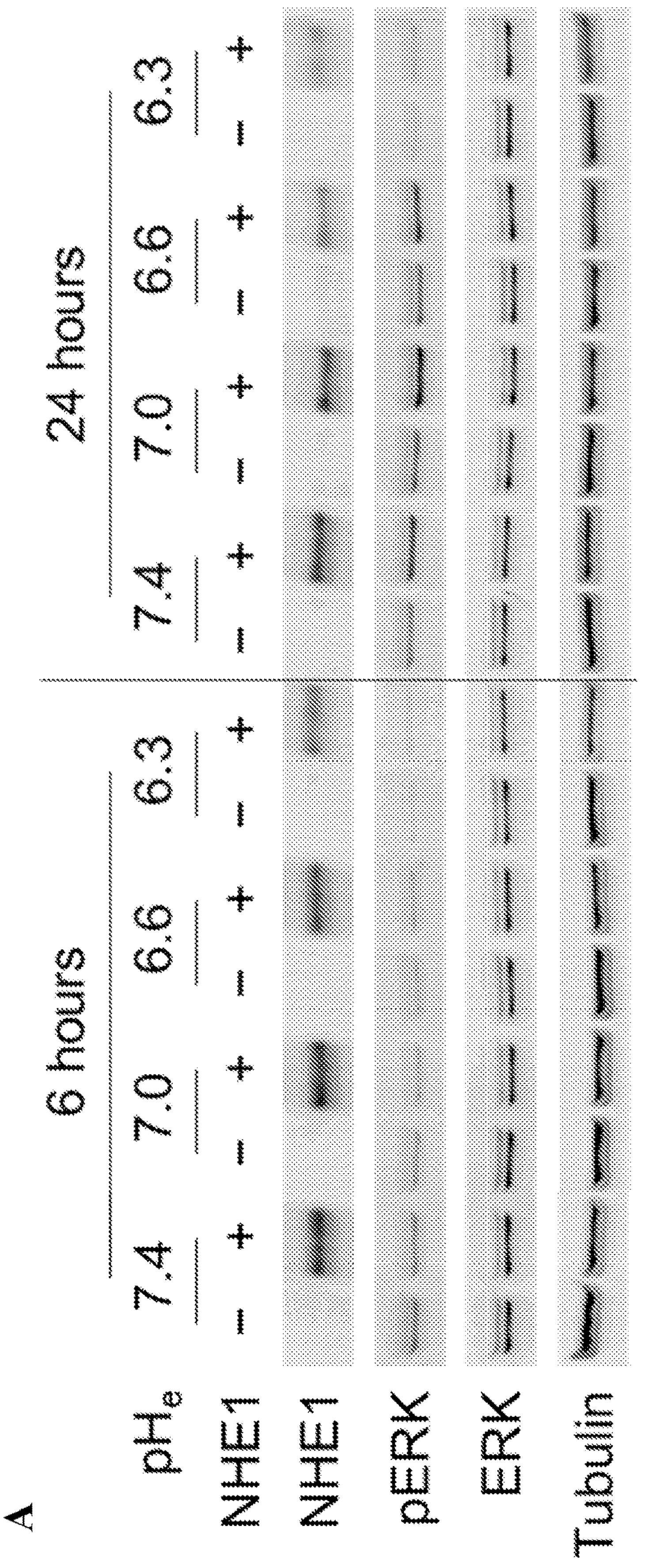
FIGS. 4A, 4B, and 4C (collectively "FIG. 4") show the effects of expression of constitutively active NHE1 on mTORC1 activity in NK-92 cells.

Empty vector- or constitutively active NHE1-transduced NK-92 cells were incubated in HEPES/PIPES/NaHCO3-buffered culture media with defined pH for 6 or 24 hours. Total proteins were extracted, and phosphorylation of ERK was detected by western blot using specific antibodies. As shown in FIG. 4A, constitutively active NHE1 enhanced ERK activity in NK-92 cells after 24 hours of incubation.

Constitutively Active NHE1 Increased Intracellular pH of NK-92 Cells.

Figure 4B:
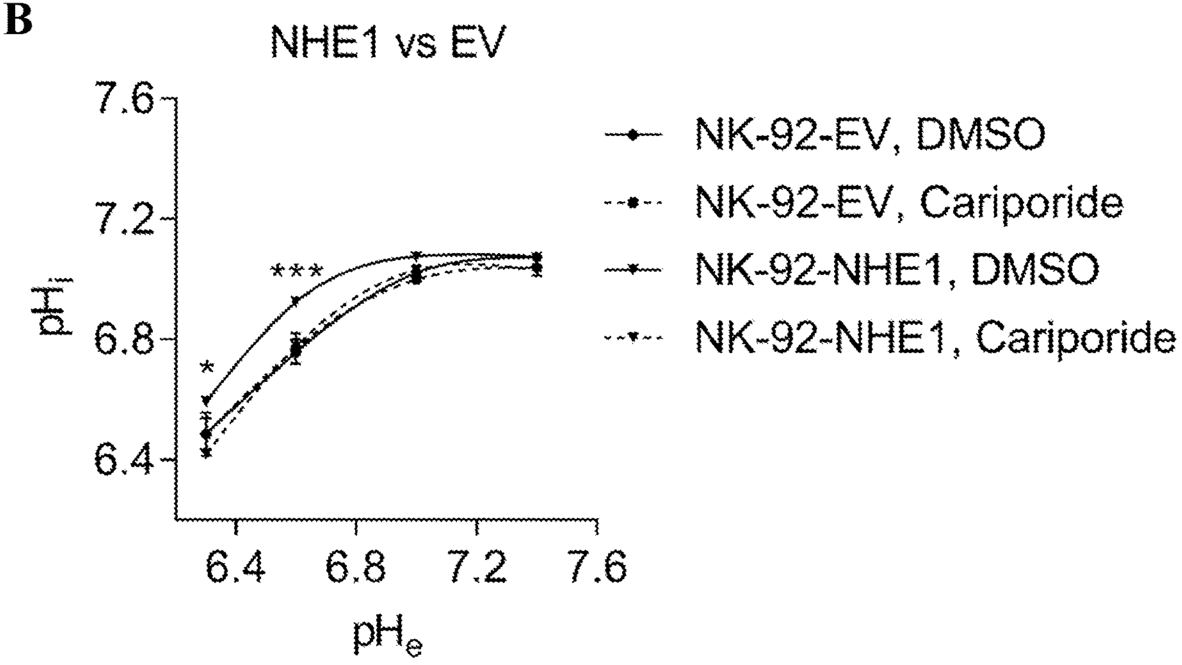

FIG. 4B is a graph showing intracellular pH ($pH_i$) of empty vector (EV)- or constitutively active NHE1-transduced NK-92 cells at indicated extracellular pH ($pH_e$) in the presence or absence of the specific NHE1 inhibitor cariporide. N=3, multiple comparison with EV, ***p<0.001, *p<0.05. Empty vector- or constitutively active NHE1-transduced NK-92 cells were loaded with 5 μM of the fluorescent pH indicator dye 5-(and-6)-Carboxy SNARF-1, and incubated in HEPES/PIPES/$NaHCO_3$-buffered culture media with defined pH for 2 hours. Cells were collected and resuspended in $Na^+$-containing live-cell imaging buffers of the same pH for 30 min before analyzed by flow cytometry. With a single excitation at 532 nm, emissions at 580 nm and 640 nm were recorded, with the ratio between the two calculated. Calibration of intracellular pH ($pH_i$) was done by incubating the cells in high-$K^+$ buffers with defined pH in the presence of 10 mM of valinomycin and nigericin, which equilibrate $pH_i$ with buffer pH. The resulting calibration curve was used to convert 580/640 nm emission ratio into $pH_i$. To inhibit NHE1 activity, the NHE1 inhibitor cariporide was added at 20 μM to the pH-defined culture media and the live-cell imaging buffers.

The results indicate that constitutively active NHE1 increased intracellular pH of NK-92 cells, which is reversed by the specific NHE1 inhibitor cariporide.

Constitutively Active NHE1 Enhanced Tumor Cell-Induced Degranulation of NK-92 Cells. Increased Degranulation Corroborates with Increased Cytotoxicity.

Figure 4C:
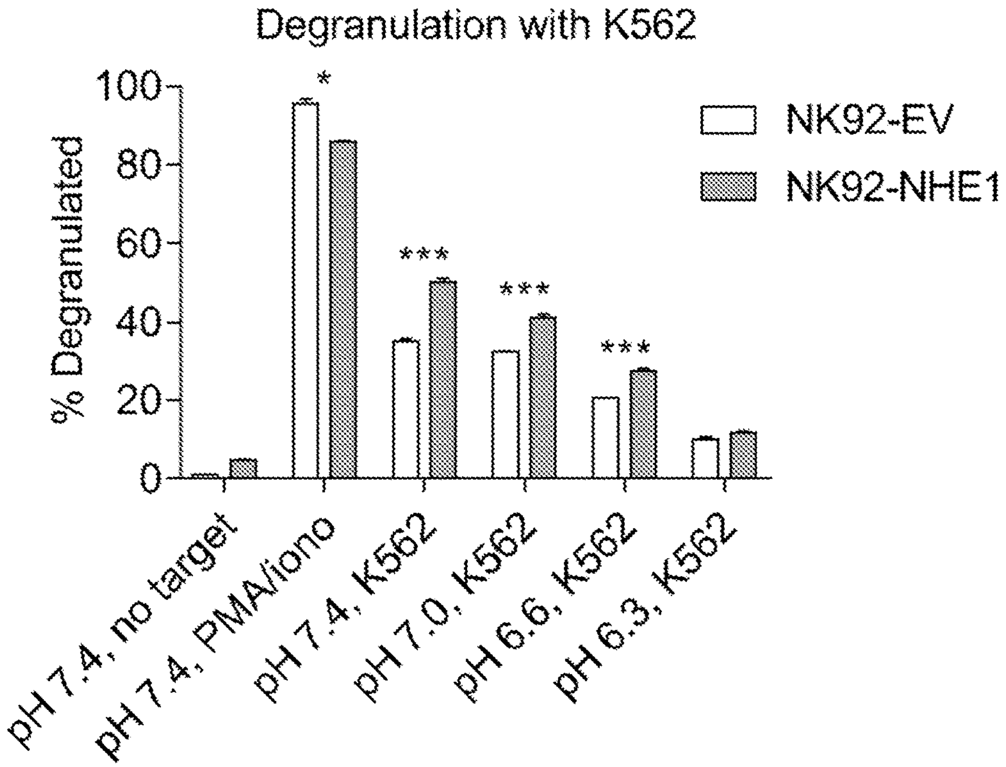

FIG. 4C is a graph showing K562-induced degranulation of empty vector (EV)- or constitutively active NHE1-transduced NK-92 cells at indicated pH for 6 hours. Phorbol myristate acetate and ionomycin (PMA/iono) induce degranulation, and were used as positive controls. N=3, ***p<0.001, *p<0.05. Empty vector- or constitutively active NHE1-transduced NK-92 cells were mixed with K562 (human leukemia) cells at 1:2 ratio in HEPES/PIPES/$NaHCO_3$-buffered culture media with defined pH for 6 hours, in the presence of vesicular trafficking inhibitors monensin and brefeldin A. Externalization of CD107a, a lysosomal marker, is associated with degranulation, and was detected by flow cytometry using PE-Cy7-conjugated anti-CD107a antibody. Phorbol myristate acetate (PMA) and ionomycin were used as positive controls to induce degranulation. Percent degranulation was calculated as the percent of CD107a-positive NK-92 cells relative to PE-Cy7-conjugated isotype control antibody-stained NK-92 cells.

The results indicate constitutively active NHE1 enhances tumor cell-induced degranulation of NK-92 cells. Increased degranulation corroborates with increased cytotoxicity.

Constitutively Active NHE1 Enhanced Cytotoxicity of NK-92 Cells.

Figure 4D:
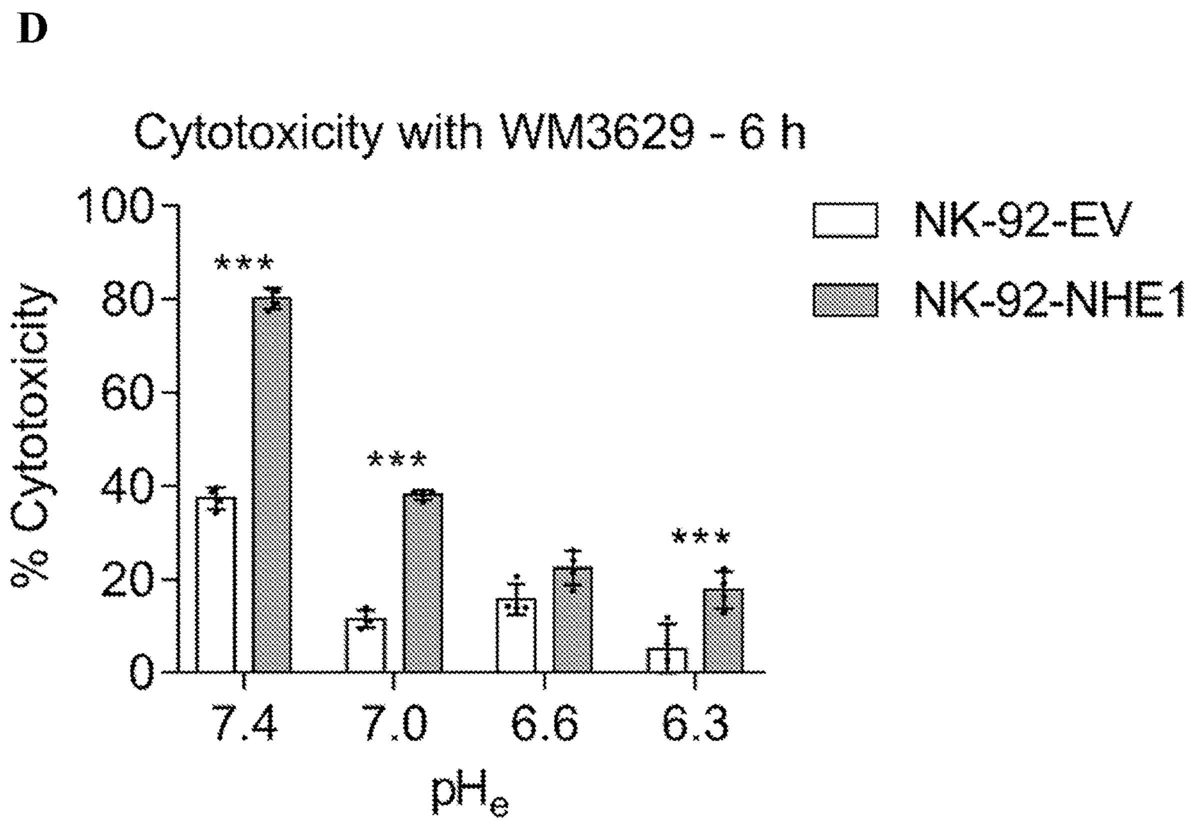
FIG. 4D shows cytotoxicity of empty vector (EV)- or constitutively active NHE1-transduced NK-92 cells to the human melanoma cell line WM3629 at indicated extracellular pH ($pH_e$) in a 6-hour in vitro killing assay. N=4, *p<0.001. In vitro cytotoxicity of empty vector- or constitutively active NHE1-transduced NK-92 cells was assessed as described above in FIG. 2**B.

FIG. 4D is a graph showing cytotoxicity of empty vector (EV)- or constitutively active NHE1-transduced NK-92 cells to the human melanoma cell line WM3629 at indicated extracellular pH ($pH_e$) in a 6-hour in vitro killing assay. N=4, ***p<0.001. Human melanoma cell line WM3629 was labeled with the fluorescent dye CELLTRACE Yellow before seeded into 24-well plates. Empty vector- or constitutively active NHE1-transduced NK-92 cells were added at 3:1 ratio to the melanoma cells. Cells were incubated in HEPES/PIPES/$NaHCO_3$-buffered culture media with defined pH for 6 hours, before being analyzed with a Guava easyCyte flow cytometer. The number of live target cells (CELLTRACE Yellow-positive) was assessed, and percent killing was calculated by comparing the number of live target cells in NK-92-containing wells to that in NK-92-free (control) wells.

As shown in FIG. 4D, NHE1 enhanced cytotoxicity of NK-92 cells to WM3629 melanoma cells at all $pH_e$.

Example 5: Effects of Expression of pH Regulatory Proteins on Antitumor Activity of NK-92 Cells In Vivo To study the exact mechanism by which acidic TME inhibits NK cells, the model NK cell line NK-92 was engineered to express pH regulatory proteins such as CA9 or NHE1 as demonstrated in EXAMPLE 4 to overcome acid-mediated suppression of antitumor activity. To test the hypothesis in vivo, ACT of irradiated NK-92 cells was performed in mice bearing xenografts of human melanoma, as previously established (Tam, Y. K., et al., J Hematother, 1999. 8(3): p. 281-90). NK-92 cells are promising candidates for ACT because they are amenable to modifications and can be mass-produced "off-the-shelf" following a standardized procedure (Suck, G., et al., Cancer Immunol Immunother, 2016. 65(4): p. 485-92). Although NK-92 cells do not form tumors in SCID mice, it is considered safer to irradiate them before introduction into animals or patients because of their tumorous origin (Gong, J. H., G. Maki, and H. G. Klingemann. Leukemia, 1994. 8(4): p. 652-8.). Furthermore, irradiation of NK-92 cells at 1000 cGy does not abolish cytotoxicity, and irradiated NK-92 cells have been tested in Phase I clinical trial in advanced melanoma and were well tolerated by patients (Arai, S., et al., Cytotherapy, 2008. 10(6): p. 625-32; Tam, Y. K., et al., J Hematother, 1999. 8(3): p. 281-90).

To generate melanoma xenografts, human melanoma cell lines were subcutaneously injected into NOD SCID mice. A melanoma cell line that is sensitive to NK-92-mediated killing identified in previous experiments such as MeWo (Tam, Y. K., et al., J Hematother, 1999. 8(3): p. 281-90) or WM3629 may be used. $1\times10^6$ trypsinized human melanoma cells were first injected into 9-12-week-old female NOD SCID mice. NK-92-EV or NK-92-CA9 cells were irradiated at 1000 cGy. 24 hours after tumor inoculation, $5\times10^6$ irradiated NK-92-EV or NK-92-CA9 cells were injected into the lateral tail vein of the mice. Equal volumes of PBS were injected into additional tumor-bearing mice as a control. After injection, tumor size and volume of the mice were monitored every five days for 40 days or until death. As an alternative approach, NK-92-NHE1 cells, as described, were injected into mice following tumor inoculation, and tumor growth with mice receiving NK-92-EV cells was compared.

Animal Use

Melanoma xenograft mouse model was used to more completely recapitulate the complex effect of the acidic TME of melanoma on infiltrating immune cells. Moreover, the in vivo study may reveal additional aspects of NK functions that are suppressed in the acidic TME, such as infiltration into tumors. 4-6 female NOD SCID (NOD.CB17-Prkdc$^{scid}$/J) mice that are 9-12 weeks old in each experimental group will be used. All mice are purchased from the Jackson Laboratory (001303) and housed in pathogen-free conditions at the Animal Facility of the Wistar Institute. Animal use follows the guidelines of the Wistar Institutional Animal Care and Use Committee (IACUC). To establish xenografts, $1\times10^6$ trypsinized human melanoma cells are subcutaneously injected into flanks of the mice. To test the antitumor effect of modified NK-92 cells, $5\times10^6$ irradiated NK-92 cells are intravenously injected into the lateral tail vein of tumor-bearing mice. The mice are euthanized by cervical dislocation before dissecting out the tumors for immunohistochemistry at the endpoint of the study.

Example 6: Expression, MTORC1 Activity, and Localization to Lysosomes of the LAMP1-RHEB Fusion Protein LAMP1-RHEB Fusion Protein could be Expressed by WM3629 Cells, and it Increased mTORC1 Activity.

Figure 5A:
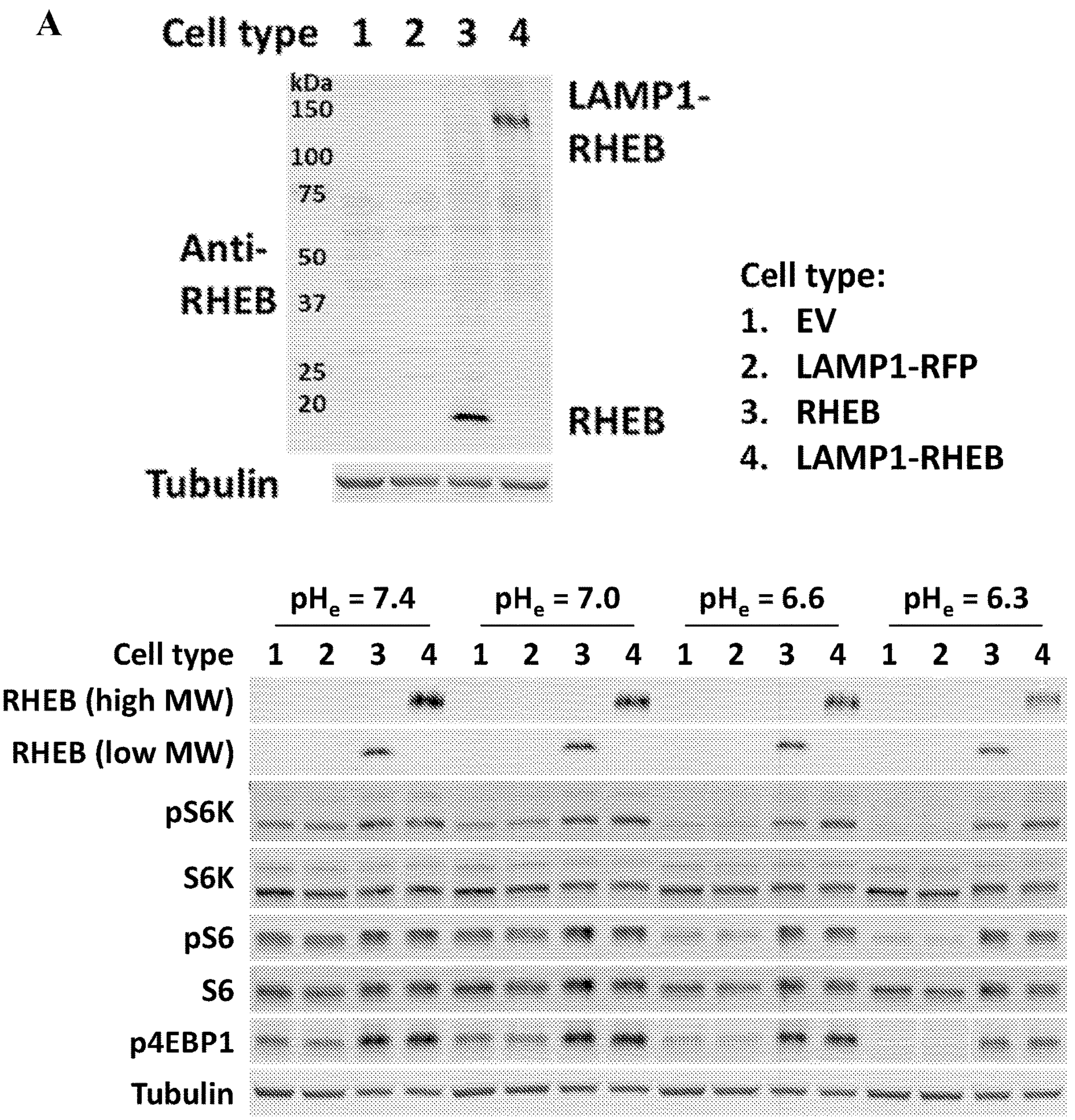
FIGS. 5A and 5B (collectively "FIG. 5") show expression, mTORC1 activity, and localization to lysosomes of the LAMP1-RHEB fusion protein.

FIG. 5A is a set of diagrams showing expression of LAMP1-RHEB (top) and mTORC1 activity after 6-hour incubation at indicated extracellular pH ($pH_e$) (bottom) in empty vector-, LAMP1-RFP-, constitutively active RHEB-, or LAMP1-RHEB-transduced WM3629 cells. LAMP1-RHEB is indicated by the high-molecular weight band detected by anti-RHEB antibody. mTORC1 activity is indicated by phosphorylation of its targets S6K, S6, and 4EBP1, with total levels of these proteins as controls. Empty vector-, LAMP1-RFP-, constitutively active RHEB-, or LAMP1-RHEB-transduced WM3629 cells were incubated in normal culture media or HEPES/PIPES/$NaHCO_3$-buffered culture media with defined pH for 6 hours. Total proteins were extracted; expression of RHEB or LAMP1-RHEB and phosphorylation of mTORC1 targets S6K, S6, and 4EBP1 were detected by western blot using specific antibodies.

As shown in FIG. 5A, LAMP1-RHEB fusion protein could be expressed by WM3629 cells, and it increased mTORC1 activity.

LAMP1-RHEB Fusion Protein was Localized to Lysosomes in WM3629 Cells.

Immunofluorescence for RHEB and LAMP2 in empty vector-, constitutively active RHEB-, or LAMP1-RHEB-transduced WM3629 cells was performed to visualize intracellular localization of LAMP1-RHEB. Contrary to RHEB-transduced WM3629 cells where RHEB signal was dispersed within the cytoplasm, LAMP1-RHEB-transduced cells showed concentrated RHEB signal as perinuclear puncta. Overlaying the RHEB image with LAMP2 image suggested that the two were mostly overlapped in LAMP1-RHEB-transduced cells, suggesting lysosomal localization of LAMP1-RHEB.

Figure 5B:
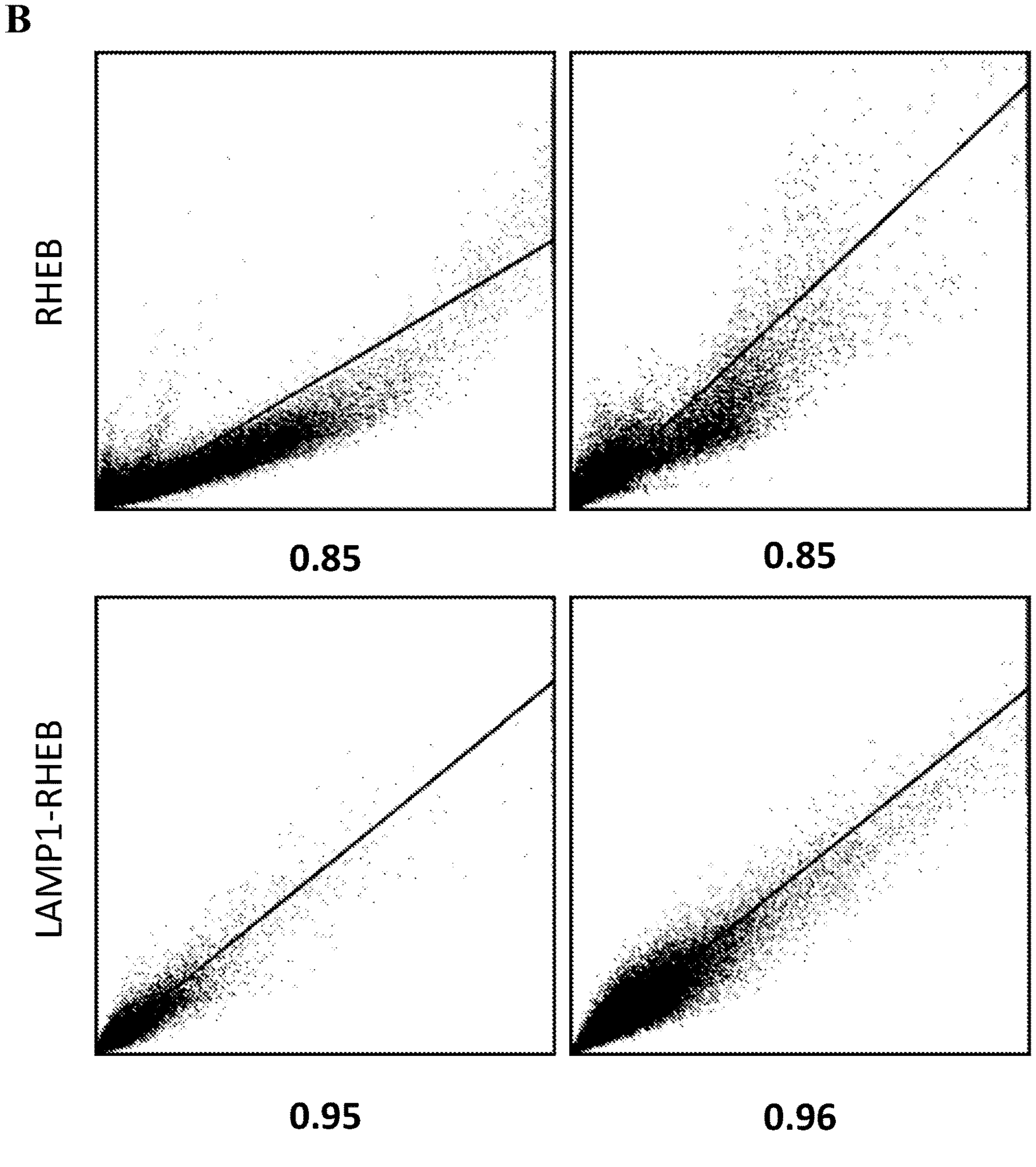

FIG. 5B is a set of diagrams showing scatter plots of fluorescence intensity of RHEB (X axis) and LAMP2 (lysosome marker, Y axis) in RHEB- or LAMP1-RHEB-transduced WM3629 cells. Plots for two representative cells are shown for each cell type. Dots correspond to pixels in the microscopic images, with Pearson's R below each plot. Higher correlation indicates more colocalization between RHEB and lysosomes. Empty vector-, constitutively active RHEB-, or LAMP1-RHEB-transduced WM3629 cells were seeded onto glass coverslips. Cells were fixed with 4% paraformaldehyde, permeabilized by 0.1% saponin, and blocked by 5% goat serum. Cells were then incubated with primary antibodies against RHEB and LAMP2, which were further labeled with fluorophore-conjugated secondary antibodies. Fluorescent images were captured using NIKON 80i microscope.

As shown in FIG. 5B, LAMP1-RHEB fusion protein was localized to lysosomes in WM3629 cells.

Other objects, features, and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

What is claimed is:

1. A method for enhancing antitumor cytotoxicity of immune cells, comprising introducing to the immune cells a genetic modification that comprises overexpression of NHE1 or a functional fragment thereof, wherein overexpression of NHE1 or a functional fragment thereof enhances antitumor cytotoxicity of the modified immune cells against tumor cells in an acidic tumor microenvironment, wherein the immune cells are cytotoxic natural killer cells, and wherein the NHE1 is a constitutively active NHE1 comprising an amino acid sequence of SEQ ID NO: 6.

2. The method of claim 1, wherein the genetic modification is introduced by transfecting the immune cell with a vector encoding NHE1 or a functional fragment thereof.

3. The method of claim 2, wherein the vector is a lentiviral vector.

4. A modified immune cell comprising a genetic modification that comprises overexpression of NHE1 or a functional fragment thereof, wherein the modified immune cell is a cytotoxic natural killer cell, wherein overexpression of NHE1 or a functional fragment thereof enhances antitumor cytotoxicity of the modified immune cell against tumor cells in an acidic tumor microenvironment, and wherein the NHE1 is a constitutively active NHE1 comprising an amino acid sequence of SEQ ID NO: 6.

5. A composition comprising the modified immune cell of claim 4.

6. A method of treating a cancer or tumor, comprising administering to a subject a therapeutically effective amount of the immune cell of claim 4.

7. The method of claim 6, wherein the immune cell is autologous to the subject.

8. The method of claim 6, further comprising, before the step of administering the modified immune cell:

obtaining from the subject a sample comprising the immune cell; and transfecting the immune cell with a vector encoding NHE1 or a functional fragment thereof.

9. The method of claim 8, further comprising, before or after the step of transfecting the immune cell, culturing the immune cell in a medium.

10. The method of claim 9, wherein the medium comprises a cytokine to promote the growth of the immune cell.

11. The method of claim 10, wherein the cytokine is interleukin-2.

12. The method of claim 8, wherein the vector is a lentiviral vector.

13. The method of claim 6, wherein the subject is a mammal.

14. The method of claim 6, wherein the subject is a human.

15. The method of claim 6, wherein the cancer or tumor is a solid tumor.

16. The method of claim 6, wherein the cancer or tumor is a hematologic tumor.

17. The method of claim 6, wherein the cancer is selected from the group consisting of melanoma, leukemia, lymphoma, multiple myeloma, prostate cancer, neuroblastoma, small cell lung cancer, and breast cancer.

18. The method of claim 6, wherein the immune cell is administered by intravenous infusion, intraperitoneal injection, subcutaneous injection or intratumoral injection.

19. The method of claim 6, further comprising administering to the subject a second therapeutic agent.

20. The method of claim 19, wherein the second therapeutic agent is an antitumor agent.

* * * * *

SEQUENCE LISTING

```
<160> NUMBER OF SEQ ID NOS: 26

<210> SEQ ID NO 1
<211> LENGTH: 184
```

<212> TYPE: PRT
<213> ORGANISM: Homo sapiens

<400> SEQUENCE: 1

Met Pro Gln Ser Lys Ser Arg Lys Ile Ala Ile Leu Gly Tyr Arg Ser
1 5 10 15

Val Gly Lys Ser Ser Leu Thr Ile Gln Phe Val Glu Gly Gln Phe Val
20 25 30

Asp Ser Tyr Asp Pro Thr Ile Glu Asn Thr Phe Thr Lys Leu Ile Thr
35 40 45

Val Asn Gly Gln Glu Tyr His Leu Gln Leu Val Asp Thr Ala Gly Gln
50 55 60

Asp Glu Tyr Ser Ile Phe Pro Gln Thr Tyr Ser Ile Asp Ile Asn Gly
65 70 75 80

Tyr Ile Leu Val Tyr Ser Val Thr Ser Ile Lys Ser Phe Glu Val Ile
85 90 95

Lys Val Ile His Gly Lys Leu Leu Asp Met Val Gly Lys Val Gln Ile
100 105 110

Pro Ile Met Leu Val Gly Asn Lys Lys Asp Leu His Met Glu Arg Val
115 120 125

Ile Ser Tyr Glu Glu Gly Lys Ala Leu Ala Glu Ser Trp Asn Ala Ala
130 135 140

Phe Leu Glu Ser Ser Ala Lys Glu Asn Gln Thr Ala Val Asp Val Phe
145 150 155 160

Arg Arg Ile Ile Leu Glu Ala Glu Lys Met Asp Gly Ala Ala Ser Gln
165 170 175

Gly Lys Ser Ser Cys Ser Val Met
180

<210> SEQ ID NO 2
<211> LENGTH: 192
<212> TYPE: PRT
<213> ORGANISM: Artificial sequence
<220> FEATURE:
<223> OTHER INFORMATION: Synthetic

<400> SEQUENCE: 2

Met Asp Tyr Lys Asp Asp Asp Asp Lys Pro Gln Ser Lys Ser Arg Lys
1 5 10 15

Ile Ala Ile Leu Gly Tyr Arg Ser Val Gly Lys Ser Ser Leu Thr Ile
20 25 30

Gln Phe Val Glu Gly Gln Phe Val Asp Ser Tyr Asp Pro Thr Ile Glu
35 40 45

Asn Thr Phe Thr Lys Leu Ile Thr Val Asn Gly Gln Glu Tyr His Leu
50 55 60

Gln Leu Val Asp Thr Ala Gly Gln Asp Glu Tyr Ser Ile Phe Pro Gln
65 70 75 80

Thr Tyr Ser Ile Asp Ile Asn Gly Tyr Ile Leu Val Tyr Ser Val Thr
85 90 95

Ser Ile Lys Ser Phe Glu Val Ile Lys Val Ile His Gly Lys Leu Leu
100 105 110

Asp Met Val Gly Lys Val Gln Ile Pro Ile Met Leu Val Gly Asn Lys
115 120 125

Lys Asp Leu His Met Glu Arg Val Ile Ser Tyr Glu Glu Gly Lys Ala
130 135 140

Leu Ala Glu Ser Trp Asn Ala Ala Phe Leu Glu Ser Ser Ala Lys Glu

```
145                 150                 155                 160

Thr Gln Thr Ala Val Asp Val Phe Arg Arg Ile Ile Leu Glu Ala Glu
                165                 170                 175

Lys Met Asp Gly Ala Ala Ser Gln Gly Lys Ser Ser Cys Ser Val Met
            180                 185                 190


<210> SEQ ID NO 3
<211> LENGTH: 603
<212> TYPE: PRT
<213> ORGANISM: Artificial sequence
<220> FEATURE:
<223> OTHER INFORMATION: Synthetic

<400> SEQUENCE: 3

Met Ala Ala Pro Gly Ala Arg Arg Pro Leu Leu Leu Leu Leu Leu Ala
1               5                   10                  15

Gly Leu Ala His Ser Ala Pro Ala Leu Phe Glu Val Lys Asp Asn Asn
            20                  25                  30

Gly Thr Ala Cys Ile Met Ala Ser Phe Ser Ala Ser Phe Leu Thr Thr
        35                  40                  45

Tyr Glu Ala Gly His Val Ser Lys Val Ser Asn Met Thr Leu Pro Ala
    50                  55                  60

Ser Ala Glu Val Leu Lys Asn Ser Ser Ser Cys Gly Glu Lys Asn Ala
65                  70                  75                  80

Ser Glu Pro Thr Leu Ala Ile Thr Phe Gly Glu Gly Tyr Leu Leu Lys
                85                  90                  95

Leu Thr Phe Thr Lys Asn Thr Thr Arg Tyr Ser Val Gln His Met Tyr
            100                 105                 110

Phe Thr Tyr Asn Leu Ser Asp Thr Gln Phe Phe Pro Asn Ala Ser Ser
        115                 120                 125

Lys Gly Pro Asp Thr Val Asp Ser Thr Thr Asp Ile Lys Ala Asp Ile
    130                 135                 140

Asn Lys Thr Tyr Arg Cys Val Ser Asp Ile Arg Val Tyr Met Lys Asn
145                 150                 155                 160

Val Thr Ile Val Leu Trp Asp Ala Thr Ile Gln Ala Tyr Leu Pro Ser
                165                 170                 175

Ser Asn Phe Ser Lys Glu Glu Thr Arg Cys Pro Gln Asp Gln Pro Ser
            180                 185                 190

Pro Thr Thr Gly Pro Pro Ser Pro Ser Pro Pro Leu Val Pro Thr Asn
        195                 200                 205

Pro Ser Val Ser Lys Tyr Asn Val Thr Gly Asp Asn Gly Thr Cys Leu
    210                 215                 220

Leu Ala Ser Met Ala Leu Gln Leu Asn Ile Thr Tyr Met Lys Lys Asp
225                 230                 235                 240

Asn Thr Thr Val Thr Arg Ala Phe Asn Ile Asn Pro Ser Asp Lys Tyr
                245                 250                 255

Ser Gly Thr Cys Gly Ala Gln Leu Val Thr Leu Lys Val Gly Asn Lys
            260                 265                 270

Ser Arg Val Leu Glu Leu Gln Phe Gly Met Asn Ala Thr Ser Ser Leu
        275                 280                 285

Phe Phe Leu Gln Gly Val Gln Leu Asn Met Thr Leu Pro Asp Ala Ile
    290                 295                 300

Glu Pro Thr Phe Ser Thr Ser Asn Tyr Ser Leu Lys Ala Leu Gln Ala
305                 310                 315                 320

Ser Val Gly Asn Ser Tyr Lys Cys Asn Ser Glu Glu His Ile Phe Val
```

```
                325                 330                 335

Ser Lys Ala Leu Ala Leu Asn Val Phe Ser Val Gln Val Gln Ala Phe
            340                 345                 350

Arg Val Glu Ser Asp Arg Phe Gly Ser Val Glu Glu Cys Val Gln Asp
        355                 360                 365

Gly Asn Asn Met Leu Ile Pro Ile Ala Val Gly Gly Ala Leu Ala Gly
    370                 375                 380

Leu Val Leu Ile Val Leu Ile Ala Tyr Leu Ile Gly Arg Lys Arg Ser
385                 390                 395                 400

His Ala Gly Tyr Gln Thr Ile Gly Gly Gly Thr Met Asp Tyr Lys Asp
                405                 410                 415

Asp Asp Asp Lys Pro Gln Ser Lys Ser Arg Lys Ile Ala Ile Leu Gly
            420                 425                 430

Tyr Arg Ser Val Gly Lys Ser Ser Leu Thr Ile Gln Phe Val Glu Gly
        435                 440                 445

Gln Phe Val Asp Ser Tyr Asp Pro Thr Ile Glu Asn Thr Phe Thr Lys
    450                 455                 460

Leu Ile Thr Val Asn Gly Gln Glu Tyr His Leu Gln Leu Val Asp Thr
465                 470                 475                 480

Ala Gly Gln Asp Glu Tyr Ser Ile Phe Pro Gln Thr Tyr Ser Ile Asp
                485                 490                 495

Ile Asn Gly Tyr Ile Leu Val Tyr Ser Val Thr Ser Ile Lys Ser Phe
            500                 505                 510

Glu Val Ile Lys Val Ile His Gly Lys Leu Leu Asp Met Val Gly Lys
        515                 520                 525

Val Gln Ile Pro Ile Met Leu Val Gly Asn Lys Lys Asp Leu His Met
    530                 535                 540

Glu Arg Val Ile Ser Tyr Glu Glu Gly Lys Ala Leu Ala Glu Ser Trp
545                 550                 555                 560

Asn Ala Ala Phe Leu Glu Ser Ser Ala Lys Glu Thr Gln Thr Ala Val
                565                 570                 575

Asp Val Phe Arg Arg Ile Ile Leu Glu Ala Glu Lys Met Asp Gly Ala
            580                 585                 590

Ala Ser Gln Gly Lys Ser Ser Cys Ser Val Met
        595                 600


<210> SEQ ID NO 4
<211> LENGTH: 459
<212> TYPE: PRT
<213> ORGANISM: Homo sapiens

<400> SEQUENCE: 4

Met Ala Pro Leu Cys Pro Ser Pro Trp Leu Pro Leu Leu Ile Pro Ala
1               5                   10                  15

Pro Ala Pro Gly Leu Thr Val Gln Leu Leu Leu Ser Leu Leu Leu Leu
            20                  25                  30

Val Pro Val His Pro Gln Arg Leu Pro Arg Met Gln Glu Asp Ser Pro
        35                  40                  45

Leu Gly Gly Gly Ser Ser Gly Glu Asp Asp Pro Leu Gly Glu Glu Asp
    50                  55                  60

Leu Pro Ser Glu Glu Asp Ser Pro Arg Glu Glu Asp Pro Pro Gly Glu
65                  70                  75                  80

Glu Asp Leu Pro Gly Glu Glu Asp Leu Pro Gly Glu Glu Asp Leu Pro
                85                  90                  95
```

```
Glu Val Lys Pro Lys Ser Glu Glu Glu Gly Ser Leu Lys Leu Glu Asp
            100                 105                 110

Leu Pro Thr Val Glu Ala Pro Gly Asp Pro Gln Glu Pro Gln Asn Asn
        115                 120                 125

Ala His Arg Asp Lys Glu Gly Asp Asp Gln Ser His Trp Arg Tyr Gly
    130                 135                 140

Gly Asp Pro Pro Trp Pro Arg Val Ser Pro Ala Cys Ala Gly Arg Phe
145                 150                 155                 160

Gln Ser Pro Val Asp Ile Arg Pro Gln Leu Ala Ala Phe Cys Pro Ala
                165                 170                 175

Leu Arg Pro Leu Glu Leu Leu Gly Phe Gln Leu Pro Pro Leu Pro Glu
            180                 185                 190

Leu Arg Leu Arg Asn Asn Gly His Ser Val Gln Leu Thr Leu Pro Pro
        195                 200                 205

Gly Leu Glu Met Ala Leu Gly Pro Gly Arg Glu Tyr Arg Ala Leu Gln
    210                 215                 220

Leu His Leu His Trp Gly Ala Ala Gly Arg Pro Gly Ser Glu His Thr
225                 230                 235                 240

Val Glu Gly His Arg Phe Pro Ala Glu Ile His Val Val His Leu Ser
                245                 250                 255

Thr Ala Phe Ala Arg Val Asp Glu Ala Leu Gly Arg Pro Gly Gly Leu
            260                 265                 270

Ala Val Leu Ala Ala Phe Leu Glu Glu Gly Pro Glu Glu Asn Ser Ala
        275                 280                 285

Tyr Glu Gln Leu Leu Ser Arg Leu Glu Glu Ile Ala Glu Glu Gly Ser
    290                 295                 300

Glu Thr Gln Val Pro Gly Leu Asp Ile Ser Ala Leu Leu Pro Ser Asp
305                 310                 315                 320

Phe Ser Arg Tyr Phe Gln Tyr Glu Gly Ser Leu Thr Thr Pro Pro Cys
                325                 330                 335

Ala Gln Gly Val Ile Trp Thr Val Phe Asn Gln Thr Val Met Leu Ser
            340                 345                 350

Ala Lys Gln Leu His Thr Leu Ser Asp Thr Leu Trp Gly Pro Gly Asp
        355                 360                 365

Ser Arg Leu Gln Leu Asn Phe Arg Ala Thr Gln Pro Leu Asn Gly Arg
    370                 375                 380

Val Ile Glu Ala Ser Phe Pro Ala Gly Val Asp Ser Ser Pro Arg Ala
385                 390                 395                 400

Ala Glu Pro Val Gln Leu Asn Ser Cys Leu Ala Ala Gly Asp Ile Leu
                405                 410                 415

Ala Leu Val Phe Gly Leu Leu Phe Ala Val Thr Ser Val Ala Phe Leu
            420                 425                 430

Val Gln Met Arg Arg Gln His Arg Arg Gly Thr Lys Gly Gly Val Ser
        435                 440                 445

Tyr Arg Pro Ala Glu Val Ala Glu Thr Gly Ala
    450                 455
```

<210> SEQ ID NO 5
<211> LENGTH: 815
<212> TYPE: PRT
<213> ORGANISM: Homo sapiens

<400> SEQUENCE: 5

```
Met Val Leu Arg Ser Gly Ile Cys Gly Leu Ser Pro His Arg Ile Phe
1               5                   10                  15
```

```
Pro Ser Leu Leu Val Val Val Ala Leu Val Gly Leu Leu Pro Val Leu
            20                  25                  30

Arg Ser His Gly Leu Gln Leu Ser Pro Thr Ala Ser Thr Ile Arg Ser
        35                  40                  45

Ser Glu Pro Pro Arg Glu Arg Ser Ile Gly Asp Val Thr Thr Ala Pro
    50                  55                  60

Pro Glu Val Thr Pro Glu Ser Arg Pro Val Asn His Ser Val Thr Asp
65                  70                  75                  80

His Gly Met Lys Pro Arg Lys Ala Phe Pro Val Leu Gly Ile Asp Tyr
                85                  90                  95

Thr His Val Arg Thr Pro Phe Glu Ile Ser Leu Trp Ile Leu Leu Ala
            100                 105                 110

Cys Leu Met Lys Ile Gly Phe His Val Ile Pro Thr Ile Ser Ser Ile
        115                 120                 125

Val Pro Glu Ser Cys Leu Leu Ile Val Val Gly Leu Leu Val Gly Gly
    130                 135                 140

Leu Ile Lys Gly Val Gly Glu Thr Pro Pro Phe Leu Gln Ser Asp Val
145                 150                 155                 160

Phe Phe Leu Phe Leu Leu Pro Pro Ile Ile Leu Asp Ala Gly Tyr Phe
                165                 170                 175

Leu Pro Leu Arg Gln Phe Thr Glu Asn Leu Gly Thr Ile Leu Ile Phe
            180                 185                 190

Ala Val Val Gly Thr Leu Trp Asn Ala Phe Phe Leu Gly Gly Leu Met
        195                 200                 205

Tyr Ala Val Cys Leu Val Gly Gly Glu Gln Ile Asn Asn Ile Gly Leu
    210                 215                 220

Leu Asp Asn Leu Leu Phe Gly Ser Ile Ile Ser Ala Val Asp Pro Val
225                 230                 235                 240

Ala Val Leu Ala Val Phe Glu Glu Ile His Ile Asn Glu Leu Leu His
                245                 250                 255

Ile Leu Val Phe Gly Glu Ser Leu Leu Asn Asp Ala Val Thr Val Val
            260                 265                 270

Leu Tyr His Leu Phe Glu Glu Phe Ala Asn Tyr Glu His Val Gly Ile
        275                 280                 285

Val Asp Ile Phe Leu Gly Phe Leu Ser Phe Phe Val Val Ala Leu Gly
    290                 295                 300

Gly Val Leu Val Gly Val Val Tyr Gly Val Ile Ala Ala Phe Thr Ser
305                 310                 315                 320

Arg Phe Thr Ser His Ile Arg Val Ile Glu Pro Leu Phe Val Phe Leu
                325                 330                 335

Tyr Ser Tyr Met Ala Tyr Leu Ser Ala Glu Leu Phe His Leu Ser Gly
            340                 345                 350

Ile Met Ala Leu Ile Ala Ser Gly Val Val Met Arg Pro Tyr Val Glu
        355                 360                 365

Ala Asn Ile Ser His Lys Ser His Thr Thr Ile Lys Tyr Phe Leu Lys
    370                 375                 380

Met Trp Ser Ser Val Ser Glu Thr Leu Ile Phe Ile Phe Leu Gly Val
385                 390                 395                 400

Ser Thr Val Ala Gly Ser His His Trp Asn Trp Thr Phe Val Ile Ser
                405                 410                 415

Thr Leu Leu Phe Cys Leu Ile Ala Arg Val Leu Gly Val Leu Gly Leu
            420                 425                 430
```

Thr Trp Phe Ile Asn Lys Phe Arg Ile Val Lys Leu Thr Pro Lys Asp
435 440 445

Gln Phe Ile Ile Ala Tyr Gly Gly Leu Arg Gly Ala Ile Ala Phe Ser
450 455 460

Leu Gly Tyr Leu Leu Asp Lys Lys His Phe Pro Met Cys Asp Leu Phe
465 470 475 480

Leu Thr Ala Ile Ile Thr Val Ile Phe Phe Thr Val Phe Val Gln Gly
485 490 495

Met Thr Ile Arg Pro Leu Val Asp Leu Leu Ala Val Lys Lys Lys Gln
500 505 510

Glu Thr Lys Arg Ser Ile Asn Glu Glu Ile His Thr Gln Phe Leu Asp
515 520 525

His Leu Leu Thr Gly Ile Glu Asp Ile Cys Gly His Tyr Gly His His
530 535 540

His Trp Lys Asp Lys Leu Asn Arg Phe Asn Lys Lys Tyr Val Lys Lys
545 550 555 560

Cys Leu Ile Ala Gly Glu Arg Ser Lys Glu Pro Gln Leu Ile Ala Phe
565 570 575

Tyr His Lys Met Glu Met Lys Gln Ala Ile Glu Leu Val Glu Ser Gly
580 585 590

Gly Met Gly Lys Ile Pro Ser Ala Val Ser Thr Val Ser Met Gln Asn
595 600 605

Ile His Pro Lys Ser Leu Pro Ser Glu Arg Ile Leu Pro Ala Leu Ser
610 615 620

Lys Asp Lys Glu Glu Glu Ile Arg Lys Ile Leu Arg Asn Asn Leu Gln
625 630 635 640

Lys Thr Arg Gln Arg Leu Arg Ser Tyr Asn Arg His Thr Leu Val Ala
645 650 655

Asp Pro Tyr Glu Glu Ala Trp Asn Gln Met Leu Leu Arg Arg Gln Lys
660 665 670

Ala Arg Gln Leu Glu Gln Lys Ile Asn Asn Tyr Leu Thr Val Pro Ala
675 680 685

His Lys Leu Asp Ser Pro Thr Met Ser Arg Ala Arg Ile Gly Ser Asp
690 695 700

Pro Leu Ala Tyr Glu Pro Lys Glu Asp Leu Pro Val Ile Thr Ile Asp
705 710 715 720

Pro Ala Ser Pro Gln Ser Pro Glu Ser Val Asp Leu Val Asn Glu Glu
725 730 735

Leu Lys Gly Lys Val Leu Gly Leu Ser Arg Asp Pro Ala Lys Val Ala
740 745 750

Glu Glu Asp Glu Asp Asp Asp Gly Gly Ile Met Met Arg Ser Lys Glu
755 760 765

Thr Ser Ser Pro Gly Thr Asp Asp Val Phe Thr Pro Ala Pro Ser Asp
770 775 780

Ser Pro Ser Ser Gln Arg Ile Gln Arg Cys Leu Ser Asp Pro Gly Pro
785 790 795 800

His Pro Glu Pro Gly Glu Gly Glu Pro Phe Phe Pro Lys Gly Gln
805 810 815

<210> SEQ ID NO 6
<211> LENGTH: 815
<212> TYPE: PRT
<213> ORGANISM: Artificial sequence
<220> FEATURE:
<223> OTHER INFORMATION: Synthetic

<400> SEQUENCE: 6

```
Met Val Leu Arg Ser Gly Ile Cys Gly Leu Ser Pro His Arg Ile Phe
1               5                   10                  15

Pro Ser Leu Leu Val Val Val Ala Leu Val Gly Leu Leu Pro Val Leu
            20                  25                  30

Arg Ser His Gly Leu Gln Leu Ser Pro Thr Ala Ser Thr Ile Arg Ser
        35                  40                  45

Ser Glu Pro Pro Arg Glu Arg Ser Ile Gly Asp Val Thr Thr Ala Pro
    50                  55                  60

Pro Glu Val Thr Pro Glu Ser Arg Pro Val Asn His Ser Val Thr Asp
65                  70                  75                  80

His Gly Met Lys Pro Arg Lys Ala Phe Pro Val Leu Gly Ile Asp Tyr
                85                  90                  95

Thr His Val Arg Thr Pro Phe Glu Ile Ser Leu Trp Ile Leu Leu Ala
            100                 105                 110

Cys Leu Met Lys Ile Gly Phe His Val Ile Pro Thr Ile Ser Ser Ile
        115                 120                 125

Val Pro Glu Ser Cys Leu Leu Ile Val Val Gly Leu Leu Val Gly Gly
    130                 135                 140

Leu Ile Lys Gly Val Gly Glu Thr Pro Pro Phe Leu Gln Ser Asp Val
145                 150                 155                 160

Phe Phe Leu Phe Leu Leu Pro Pro Ile Ile Leu Asp Ala Gly Tyr Phe
                165                 170                 175

Leu Pro Leu Arg Gln Phe Thr Glu Asn Leu Gly Thr Ile Leu Ile Phe
            180                 185                 190

Ala Val Val Gly Thr Leu Trp Asn Ala Phe Phe Leu Gly Gly Leu Met
        195                 200                 205

Tyr Ala Val Cys Leu Val Gly Gly Glu Gln Ile Asn Asn Ile Gly Leu
    210                 215                 220

Leu Asp Asn Leu Leu Phe Gly Ser Ile Ile Ser Ala Val Asp Pro Val
225                 230                 235                 240

Ala Val Leu Ala Val Phe Glu Glu Ile His Ile Asn Glu Leu Leu His
                245                 250                 255

Ile Leu Val Phe Gly Glu Ser Leu Leu Asn Asp Ala Val Thr Val Val
            260                 265                 270

Leu Tyr His Leu Phe Glu Glu Phe Ala Asn Tyr Glu His Val Gly Ile
        275                 280                 285

Val Asp Ile Phe Leu Gly Phe Leu Ser Phe Phe Val Val Ala Leu Gly
    290                 295                 300

Gly Val Leu Val Gly Val Val Tyr Gly Val Ile Ala Ala Phe Thr Ser
305                 310                 315                 320

Arg Phe Thr Ser His Ile Arg Val Ile Glu Pro Leu Phe Val Phe Leu
                325                 330                 335

Tyr Ser Tyr Met Ala Tyr Leu Ser Ala Glu Leu Phe His Leu Ser Gly
            340                 345                 350

Ile Met Ala Leu Ile Ala Ser Gly Val Val Met Arg Pro Tyr Val Glu
        355                 360                 365

Ala Asn Ile Ser His Lys Ser His Thr Thr Ile Lys Tyr Phe Leu Lys
    370                 375                 380

Met Trp Ser Ser Val Ser Glu Thr Leu Ile Phe Ile Phe Leu Gly Val
385                 390                 395                 400

Ser Thr Val Ala Gly Ser His His Trp Asn Trp Thr Phe Val Ile Ser
```

```
                405                 410                 415

Thr Leu Leu Phe Cys Leu Ile Ala Arg Val Leu Gly Val Leu Gly Leu
            420                 425                 430

Thr Trp Phe Ile Asn Lys Phe Arg Ile Val Lys Leu Thr Pro Lys Asp
        435                 440                 445

Gln Phe Ile Ile Ala Tyr Gly Gly Leu Arg Gly Ala Ile Ala Phe Ser
    450                 455                 460

Leu Gly Tyr Leu Leu Asp Lys Lys His Phe Pro Met Cys Asp Leu Phe
465                 470                 475                 480

Leu Thr Ala Ile Ile Thr Val Ile Phe Phe Thr Val Phe Val Gln Gly
                485                 490                 495

Met Thr Ile Arg Pro Leu Val Asp Leu Leu Ala Val Lys Lys Lys Gln
            500                 505                 510

Glu Thr Lys Arg Ser Ile Asn Glu Glu Ile His Thr Gln Phe Leu Asp
        515                 520                 525

His Leu Leu Thr Gly Ile Glu Asp Ile Cys Gly Arg Tyr Gly Arg Arg
    530                 535                 540

Arg Trp Lys Asp Lys Leu Asn Arg Phe Asn Lys Lys Tyr Val Lys Lys
545                 550                 555                 560

Cys Leu Ile Ala Gly Glu Arg Ser Lys Glu Pro Gln Leu Ile Ala Phe
                565                 570                 575

Tyr His Lys Met Glu Met Lys Gln Ala Ile Glu Leu Val Glu Ser Gly
            580                 585                 590

Gly Met Gly Lys Ile Pro Ser Ala Val Ser Thr Val Ser Met Gln Asn
        595                 600                 605

Ile His Pro Lys Ser Leu Pro Ser Glu Arg Ile Leu Pro Ala Leu Ser
    610                 615                 620

Lys Asp Lys Glu Glu Glu Ile Arg Lys Ile Leu Arg Asn Asn Leu Gln
625                 630                 635                 640

Lys Thr Arg Gln Arg Leu Arg Ser Tyr Asn Arg His Thr Leu Val Ala
                645                 650                 655

Asp Pro Tyr Glu Glu Ala Trp Asn Gln Met Leu Leu Arg Arg Gln Lys
            660                 665                 670

Ala Arg Gln Leu Glu Gln Lys Ile Asn Asn Tyr Leu Thr Val Pro Ala
        675                 680                 685

His Lys Leu Asp Ser Pro Thr Met Ser Arg Ala Arg Ile Gly Ser Asp
    690                 695                 700

Pro Leu Ala Tyr Glu Pro Lys Glu Asp Leu Pro Val Ile Thr Ile Asp
705                 710                 715                 720

Pro Ala Ser Pro Gln Ser Pro Glu Ser Val Asp Leu Val Asn Glu Glu
                725                 730                 735

Leu Lys Gly Lys Val Leu Gly Leu Ser Arg Asp Pro Ala Lys Val Ala
            740                 745                 750

Glu Glu Asp Glu Asp Asp Asp Gly Gly Ile Met Met Arg Ser Lys Glu
        755                 760                 765

Thr Ser Ser Pro Gly Thr Asp Asp Val Phe Thr Pro Ala Pro Ser Asp
    770                 775                 780

Ser Pro Ser Ser Gln Arg Ile Gln Arg Cys Leu Ser Asp Pro Gly Pro
785                 790                 795                 800

His Pro Glu Pro Gly Glu Gly Glu Pro Phe Phe Pro Lys Gly Gln
                805                 810                 815

<210> SEQ ID NO 7
```

<211> LENGTH: 555
<212> TYPE: DNA
<213> ORGANISM: Homo sapiens

<400> SEQUENCE: 7
atgccgcagt ccaagtcccg gaagatcgcg atcctgggct accggtctgt ggggaaatcc 60
tcattgacga ttcaatttgt tgaaggccaa tttgtggact cctacgatcc aaccatagaa 120
aacactttta caaagttgat cacagtaaat ggacaagaat atcatcttca acttgtagac 180
acagccgggc aagatgaata ttctatcttt cctcagacat actccataga tattaatggc 240
tatattcttg tgtattctgt tacatcaatc aaaagttttg aagtgattaa agttatccat 300
ggcaaattgt tggatatggt ggggaaagta caaataccta ttatgttggt tgggaataag 360
aaagacctgc atatggaaag ggtgatcagt tatgaagaag ggaaagcttt ggcagaatct 420
tggaatgcag ctttttttgga atcttctgct aaagaaaatc agactgctgt ggatgttttt 480
cgaaggataa ttttggaggc agaaaaaatg gacggggcag cttcacaagg caagtcttca 540
tgctcggtga tgtga 555

<210> SEQ ID NO 8
<211> LENGTH: 579
<212> TYPE: DNA
<213> ORGANISM: Artificial sequence
<220> FEATURE:
<223> OTHER INFORMATION: Synthetic

<400> SEQUENCE: 8
atggattaca aggatgacga tgacaagccg cagtccaagt cccggaagat cgcgatcctg 60
ggctaccggt ctgtggggaa atcctcattg acgattcaat ttgttgaagg ccaatttgtg 120
gactcctacg atccaaccat agaaaacact tttacaaagt tgatcacagt aaatggacaa 180
gaatatcatc ttcaacttgt agacacagcc gggcaagatg aatattctat ctttcctcag 240
acatactcca tagatattaa tggctatatt cttgtgtatt ctgttacatc aatcaaaagt 300
tttgaagtga ttaaagttat ccatggcaaa ttgttggata tggtggggaa agtacaaata 360
cctattatgt tggttgggaa taagaaagac ctgcatatgg aaagggtgat cagttatgaa 420
gaagggaaag ctttggcaga atcttggaat gcagcttttt tggaatcttc tgctaaagaa 480
aatcagactg ctgtggatgt ttttcgaagg ataattttgg aggcagaaaa aatggacggg 540
gcagcttcac aaggcaagtc ttcatgctcg gtgatgtga 579

<210> SEQ ID NO 9
<211> LENGTH: 1812
<212> TYPE: DNA
<213> ORGANISM: Artificial sequence
<220> FEATURE:
<223> OTHER INFORMATION: Synthetic

<400> SEQUENCE: 9
atggcggccc cgggcgcccg gcggccgctg ctcctgttgc tgctggcagg ccttgcacac 60
agcgccccag cactgttcga ggtgaaagac aacaacggca cagcgtgtat aatggccagc 120
ttctctgcct cctttctgac cacctatgag gctggacatg tttctaaggt ctcgaatatg 180
accctgccag cctctgcaga agtcctgaag aatagcagct cttgtggtga aaagaatgct 240
tctgagccca ccctcgcaat cacctttgga gaaggatatt tactgaaact caccttcaca 300
aaaaacacaa cacgttacag tgtccagcac atgtatttca catataacct gtcagacaca 360
caattctttc ccaatgccag ctccaaaggg cccgacactg tggattccac aactgacatc 420

```
aaggcagaca tcaacaaaac ataccgatgt gtcagcgaca tcagggtcta catgaagaat    480
gtgaccattg tgctctggga cgctactatc caggcctacc tgccgagtag caacttcagc    540
aaggaagaga cacgctgccc acaggatcaa ccttccccaa ctactgggcc acccagcccc    600
tcaccaccac ttgtgcccac aaaccccagt gtgtccaagt acaatgtgac tggtgacaat    660
ggaacctgcc tgctggcctc tatggcactg caactcaaca tcacctacat gaagaaggac    720
aacacgactg tgaccagagc attcaacatc aacccaagtg acaaatatag tgggacttgc    780
ggtgcccagt tggtgaccct gaaggtgggg aacaagagca gagtcctgga gctgcagttt    840
gggatgaatg ccacttctag cctgtttttc ctgcaaggag ttcagttgaa catgactctt    900
cctgatgcca tagagcccac gttcagcacc tccaactatt ccctgaaagc tcttcaggcc    960
agtgtcggca actcatacaa gtgcaacagt gaggagcaca tctttgtcag caaggcgctc   1020
gccctcaatg tcttcagcgt gcaagtccag gctttcaggg tagaaagtga caggtttggg   1080
tctgtggaag agtgtgtaca ggacggtaac aacatgctga tccccattgc tgtgggcggg   1140
gccctggcag ggctggtcct catcgtcctc atcgcctacc tcatcggcag gaagaggagt   1200
cacgcgggct atcagaccat cggaggcggc accatggatt acaaggatga cgatgacaag   1260
ccgcagtcca agtcccggaa gatcgcgatc ctgggctacc ggtctgtggg gaaatcctca   1320
ttgacgattc aatttgttga aggccaattt gtggactcct acgatccaac catagaaaac   1380
acttttacaa agttgatcac agtaaatgga caagaatatc atcttcaact tgtagacaca   1440
gccgggcaag atgaatattc tatctttcct cagacatact ccatagatat taatggctat   1500
attcttgtgt attctgttac atcaatcaaa agttttgaag tgattaaagt tatccatggc   1560
aaattgttgg atatggtggg gaaagtacaa atacctatta tgttggttgg gaataagaaa   1620
gacctgcata tggaaagggt gatcagttat gaagaaggga aagctttggc agaatcttgg   1680
aatgcagctt ttttggaatc ttctgctaaa gaaactcaga ctgctgtgga tgtttttcga   1740
aggataattt tggaggcaga aaaaatggac ggggcagctt cacaaggcaa gtcttcatgc   1800
tcggtgatgt ga                                                       1812
```

<210> SEQ ID NO 10
<211> LENGTH: 1380
<212> TYPE: DNA
<213> ORGANISM: Homo sapiens

<400> SEQUENCE: 10

```
atggctcccc tgtgccccag cccctggctc cctctgttga tcccggcccc tgctccaggc     60
ctcactgtgc aactgctgct gtcactgctg cttctggtgc ctgtccatcc ccagaggttg    120
ccccggatgc aggaggattc cccccttggga ggaggctctt ctggggaaga tgacccactg    180
ggcgaggagg atctgcccag tgaagaggat tcacccagag aggaggatcc acccggagag    240
gaggatctac ctggagagga ggatctacct ggagaggagg atctacctga agttaagcct    300
aaatcagaag aagagggctc cctgaagtta gaggatctac ctactgttga ggctcctgga    360
gatcctcaag aaccccagaa taatgcccac agggacaaag aaggggatga ccagagtcat    420
tggcgctatg gaggcgaccc gccctggccc cgggtgtccc cagcctgcgc gggccgcttc    480
cagtccccgg tggatatccg cccccagctc gccgccttct gcccggccct gcgcccccctg    540
gaactcctgg gcttccagct cccgccgctc ccagaactgc gcctgcgcaa caatggccac    600
agtgtgcaac tgaccctgcc tcctgggcta gagatggctc tgggtcccgg gcgggagtac    660
```

```
cgggctctgc agctgcatct gcactggggg gctgcaggtc gtccgggctc ggagcacact    720

gtggaaggcc accgtttccc tgccgagatc cacgtggttc acctcagcac cgcctttgcc    780

agagttgacg aggccttggg gcgcccggga ggcctggccg tgttggccgc ctttctggag    840

gagggcccgg aagaaaacag tgcctatgag cagttgctgt ctcgcttgga agaaatcgct    900

gaggaaggct cagagactca ggtcccagga ctggacatat ctgcactcct gccctctgac    960

ttcagccgct acttccaata tgaggggtct ctgactacac cgccctgtgc ccagggtgtc   1020

atctggactg tgtttaacca gacagtgatg ctgagtgcta agcagctcca caccctctct   1080

gacaccctgt ggggacctgg tgactctcgg ctacagctga acttccgagc gacgcagcct   1140

ttgaatgggc gagtgattga ggcctccttc cctgctggag tggacagcag tcctcgggct   1200

gctgagccag tccagctgaa ttcctgcctg gctgctggtg acatcctagc cctggttttt   1260

ggcctccttt ttgctgtcac cagcgtcgcg ttccttgtgc agatgagaag gcagcacaga   1320

aggggaacca aagggggtgt gagctaccgc ccagcagagg tagccgagac tggagcctag   1380
```

```
<210> SEQ ID NO 11
<211> LENGTH: 2448
<212> TYPE: DNA
<213> ORGANISM: Homo sapiens

<400> SEQUENCE: 11

atggtgctga ggagtggtat ctgcggcctg tccccccata ggatatttcc aagtttgctt     60

gtagttgtag ctctcgtcgg attgctccct gttctgcgct ctcacggact gcaactgtct    120

ccgactgctt ccactattcg gtcatctgag ccaccgcgcg agaggagcat cggggatgtt    180

actacagcac caccagaggt cacccccgag tcacgaccag tgaaccactc cgtcactgat    240

catgggatga agccgcggaa ggctttcccc gtgctcggga ttgattacac gcatgtacgg    300

acaccttttg aaatctcact ctggatcctg ttggcgtgtc tcatgaaaat cgggtttcat    360

gtaataccga cgatttcttc catcgtgcca gagtcttgtc tcctcattgt ggtcggtctc    420

ctcgttggcg gtctcatcaa gggagttggc gagacaccgc cgtttttgca atcagatgta    480

ttctttttgt ttcttctgcc cccaataatt cttgatgcag ggtatttctt gccgctcaga    540

cagtttactg agaaccttgg gactatactt atattcgcgg tagtaggaac cctctggaac    600

gcctttttcc tgggagggtt gatgtacgct gtatgtctcg tcggtggaga gcaaattaac    660

aatattggtc tgttggacaa tcttttgttc ggctccataa tcagcgctgt cgatccagtc    720

gccgtgctcg ctgtattcga ggaaatccac atcaacgaac ttcttcatat actcgttttc    780

ggtgaaagtc ttctcaatga tgccgtgact gtagttcttt accatctctt cgaagagttc    840

gccaactatg agcacgttgg aatagtcgat attttccttg ggtttctctc tttcttcgtc    900

gttgccctcg gaggagtctt ggtaggcgtc gtctacggcg tcatagcagc ctttacttct    960

aggtttacgt ctcacatacg cgtgattgag ccgttgtttg tttttctgta ttcctatatg   1020

gcctatttga gtgccgagct tttcatctt agcggtataa tggcccttat cgcgtctggg   1080

gttgtcatgc gcccatatgt cgaggcgaat ataagtcaca aatcccatac cacgattaaa   1140

tatttcctca aaatgtggtc aagcgtttca gaaaccctta tattcatatt cctgggagtc   1200

agcacagtag cgggctccca tcactggaac tggacattcg taatatctac gttgctcttt   1260

tgcctgatag ccagagttct gggcgtgctc ggactgactt ggtttattaa caaattcaga   1320

attgttaaac tgacgcctaa agaccagttc atcatagcat atggaggttt gcgcggggca   1380

atcgcattca gtctggggta tctcctcgac aagaagcact tccccatgtg cgatctgttt   1440
```

```
ttgaccgcga tcatcacagt catatttttt acggtttttg tacaggggat gaccatcagg   1500

ccactcgttg atcttttggc ggtcaaaaaa aaacaagaga cgaaacgaag tataaatgaa   1560

gagatacata ctcagttctt ggaccacttg ctgaccggga tagaggacat ttgtggccac   1620

tatggtcatc atcactggaa ggataaactg aatcggttta acaaaaaata tgtgaaaaaa   1680

tgcttgatcg ccggggaacg gtctaaagaa ccacagctta tagccttcta tcataaaatg   1740

gagatgaagc aggcgataga gctggtggaa tccggaggaa tgggaaagat acccagcgct   1800

gtctcaaccg tgtctatgca aaatatccat ccgaagtccc ttccatctga gcgaatcctg   1860

cccgccctca gcaaggacaa agaggaggag attcggaaaa ttctgaggaa taacttgcag   1920

aagactagac agcgcctcag atcctataac cgacacaccc tggtggccga cccctatgag   1980

gaagcctgga accagatgtt gcttcgacgg caaaaagctc gacaattgga gcaaaagatc   2040

aataactatc tcaccgtccc tgctcacaaa cttgactctc ccactatgtc tcgagccagg   2100

ataggatctg accccctggc gtacgagcca aaagaggatt tgcctgtcat tacgatagat   2160

ccggcctccc cgcagtctcc cgagtccgta gacctggtta acgaggaact taagggcaaa   2220

gttctgggcc ttagtcggga tccggcaaag gttgctgagg aggacgaaga tgatgatggg   2280

ggtattatga tgaggtcaaa agaaacaagt tcccccggta cggacgatgt attcacgccg   2340

gcgccttctg actccccaag ctctcaacgc atacagcggt gcctgagtga cccggggccc   2400

catccggagc cgggtgaagg ggagccgttt tttcctaaag gccaatag                2448
```

```
<210> SEQ ID NO 12
<211> LENGTH: 2448
<212> TYPE: DNA
<213> ORGANISM: Artificial sequence
<220> FEATURE:
<223> OTHER INFORMATION: Synthetic

<400> SEQUENCE: 12
```

```
atggtgctga ggagtggtat ctgcggcctg tccccccata ggatatttcc aagtttgctt     60

gtagttgtag ctctcgtcgg attgctccct gttctgcgct ctcacggact gcaactgtct    120

ccgactgctt ccactattcg gtcatctgag ccaccgcgcg agaggagcat cggggatgtt    180

actacagcac caccagaggt cacccccgag tcacgaccag tgaaccactc cgtcactgat    240

catgggatga agccgcggaa ggctttcccc gtgctcggga ttgattacac gcatgtacgg    300

acaccttttg aaatctcact ctggatcctg ttggcgtgtc tcatgaaaat cgggtttcat    360

gtaataccga cgatttcttc catcgtgcca gagtcttgtc tcctcattgt ggtcggtctc    420

ctcgttggcg gtctcatcaa gggagttggc gagacaccgc cgtttttgca atcagatgta    480

ttctttttgt ttcttctgcc cccaataatt cttgatgcag ggtatttctt gccgctcaga    540

cagtttactg agaaccttgg gactatactt atattcgcgg tagtaggaac cctctggaac    600

gcctttttcc tgggagggtt gatgtacgct gtatgtctcg tcggtggaga gcaaattaac    660

aatattggtc tgttggacaa tcttttgttc ggctccataa tcagcgctgt cgatccagtc    720

gccgtgctcg ctgtattcga ggaaatccac atcaacgaac ttcttcatat actcgttttc    780

ggtgaaagtc ttctcaatga tgccgtgact gtagttcttt accatctctt cgaagagttc    840

gccaactatg agcacgttgg aatagtcgat attttccttg ggtttctctc tttcttcgtc    900

gttgccctcg gaggagtctt ggtaggcgtc gtctacggcg tcatagcagc ctttacttct    960

aggtttacgt ctcacatacg cgtgattgag ccgttgtttg tttttctgta ttcctatatg   1020
```

```
gcctatttga gtgccgagct ttttcatctt agcggtataa tggcccttat cgcgtctggg   1080

gttgtcatgc gcccatatgt cgaggcgaat ataagtcaca aatcccatac cacgattaaa   1140

tatttcctca aaatgtggtc aagcgtttca gaaaccctta tattcatatt cctgggagtc   1200

agcacagtag cgggctccca tcactggaac tggacattcg taatatctac gttgctcttt   1260

tgcctgatag ccagagttct gggcgtgctc ggactgactt ggtttattaa caaattcaga   1320

attgttaaac tgacgcctaa agaccagttc atcatagcat atggaggttt gcgcggggca   1380

atcgcattca gtctggggta tctcctcgac aagaagcact tccccatgtg cgatctgttt   1440

ttgaccgcga tcatcacagt catatttttt acggtttttg tacaggggat gaccatcagg   1500

ccactcgttg atcttttggc ggtcaaaaaa aaacaagaga cgaaacgaag tataaatgaa   1560

gagatacata ctcagttctt ggaccacttg ctgaccggga tagaggacat ttgtggccgc   1620

tatggcaggc gacgatggaa ggataaactg aatcggttta acaaaaaata tgtgaaaaaa   1680

tgcttgatcg ccggggaacg gtctaaagaa ccacagctta tagccttcta tcataaaatg   1740

gagatgaagc aggcgataga gctggtggaa tccggaggaa tgggaaagat acccagcgct   1800

gtctcaaccg tgtctatgca aaatatccat ccgaagtccc ttccatctga gcgaatcctg   1860

cccgccctca gcaaggacaa agaggaggag attcggaaaa ttctgaggaa taacttgcag   1920

aagactagac agcgcctcag atcctataac cgacacaccc tggtggccga cccctatgag   1980

gaagcctgga accagatgtt gcttcgacgg caaaaagctc gacaattgga gcaaaagatc   2040

aataactatc tcaccgtccc tgctcacaaa cttgactctc ccactatgtc tcgagccagg   2100

ataggatctg acccccctggc gtacgagcca aaagaggatt tgcctgtcat tacgatagat   2160

ccggcctccc cgcagtctcc cgagtccgta gacctggtta acgaggaact taagggcaaa   2220

gttctgggcc ttagtcggga tccggcaaag gttgctgagg aggacgaaga tgatgatggg   2280

ggtattatga tgaggtcaaa agaaacaagt tcccccggta cggacgatgt attcacgccg   2340

gcgccttctg actccccaag ctctcaacgc atacagcggt gcctgagtga cccggggccc   2400

catccggagc cgggtgaagg ggagccgttt tttcctaaag gccaatag                2448
```

<210> SEQ ID NO 13
<211> LENGTH: 5
<212> TYPE: PRT
<213> ORGANISM: Artificial sequence
<220> FEATURE:
<223> OTHER INFORMATION: Synthetic

<400> SEQUENCE: 13

```
Gly Gly Gly Thr Met
1               5
```

<210> SEQ ID NO 14
<211> LENGTH: 2
<212> TYPE: PRT
<213> ORGANISM: Artificial sequence
<220> FEATURE:
<223> OTHER INFORMATION: Synthetic

<400> SEQUENCE: 14

```
Ser Gly
1
```

<210> SEQ ID NO 15
<211> LENGTH: 3
<212> TYPE: PRT
<213> ORGANISM: Artificial sequence
<220> FEATURE:
<223> OTHER INFORMATION: Synthetic

<400> SEQUENCE: 15

Ser Gly Ser
1

<210> SEQ ID NO 16
<211> LENGTH: 3
<212> TYPE: PRT
<213> ORGANISM: Artificial sequence
<220> FEATURE:
<223> OTHER INFORMATION: Synthetic

<400> SEQUENCE: 16

Ser Gly Gly
1

<210> SEQ ID NO 17
<211> LENGTH: 4
<212> TYPE: PRT
<213> ORGANISM: Artificial sequence
<220> FEATURE:
<223> OTHER INFORMATION: Synthetic

<400> SEQUENCE: 17

Ser Gly Gly Ser
1

<210> SEQ ID NO 18
<211> LENGTH: 4
<212> TYPE: PRT
<213> ORGANISM: Artificial sequence
<220> FEATURE:
<223> OTHER INFORMATION: Synthetic

<400> SEQUENCE: 18

Ser Gly Gly Gly
1

<210> SEQ ID NO 19
<211> LENGTH: 5
<212> TYPE: PRT
<213> ORGANISM: Artificial sequence
<220> FEATURE:
<223> OTHER INFORMATION: Synthetic

<400> SEQUENCE: 19

Ser Gly Gly Gly Ser
1               5

<210> SEQ ID NO 20
<211> LENGTH: 5
<212> TYPE: PRT
<213> ORGANISM: Artificial sequence
<220> FEATURE:
<223> OTHER INFORMATION: Synthetic

<400> SEQUENCE: 20

Ser Gly Gly Gly Gly
1               5

<210> SEQ ID NO 21
<211> LENGTH: 6
<212> TYPE: PRT
<213> ORGANISM: Artificial sequence
<220> FEATURE:

<223> OTHER INFORMATION: Synthetic

<400> SEQUENCE: 21

Ser Gly Gly Gly Gly Ser
1 5

<210> SEQ ID NO 22
<211> LENGTH: 6
<212> TYPE: PRT
<213> ORGANISM: Artificial sequence
<220> FEATURE:
<223> OTHER INFORMATION: Synthetic

<400> SEQUENCE: 22

Ser Gly Gly Gly Gly Gly
1 5

<210> SEQ ID NO 23
<211> LENGTH: 7
<212> TYPE: PRT
<213> ORGANISM: Artificial sequence
<220> FEATURE:
<223> OTHER INFORMATION: Synthetic

<400> SEQUENCE: 23

Ser Gly Gly Gly Gly Gly Ser
1 5

<210> SEQ ID NO 24
<211> LENGTH: 7
<212> TYPE: PRT
<213> ORGANISM: Artificial sequence
<220> FEATURE:
<223> OTHER INFORMATION: Synthetic

<400> SEQUENCE: 24

Ser Gly Gly Gly Gly Gly Gly
1 5

<210> SEQ ID NO 25
<211> LENGTH: 9
<212> TYPE: PRT
<213> ORGANISM: Artificial sequence
<220> FEATURE:
<223> OTHER INFORMATION: Synthetic

<400> SEQUENCE: 25

Ser Gly Gly Ser Gly Gly Gly Gly Ser
1 5

<210> SEQ ID NO 26
<211> LENGTH: 15
<212> TYPE: DNA
<213> ORGANISM: Artificial sequence
<220> FEATURE:
<223> OTHER INFORMATION: Synthetic

<400> SEQUENCE: 26
ggaggcggca ccatg 15